US010072040B2

(12) United States Patent
von Geldern et al.

(10) Patent No.: US 10,072,040 B2
(45) Date of Patent: Sep. 11, 2018

(54) TYLOSIN A ANALOGS AND DERIVATIVES

(71) Applicant: AbbVie Inc., North Chicago, IL (US)

(72) Inventors: Thomas W. von Geldern, Richmond, IL (US); Dale J. Kempf, Libertyville, IL (US); Kennan C. Marsh, Lake Forest, IL (US)

(73) Assignee: ABBVIE INC., North Chicago, IL (US)

( * ) Notice: Subject to any disclaimer, the term of this patent is extended or adjusted under 35 U.S.C. 154(b) by 500 days.

(21) Appl. No.: 14/643,858

(22) Filed: Mar. 10, 2015

(65) Prior Publication Data

US 2015/0259374 A1  Sep. 17, 2015

Related U.S. Application Data

(60) Provisional application No. 61/951,179, filed on Mar. 11, 2014, provisional application No. 62/052,626, filed on Sep. 19, 2014.

(51) Int. Cl.
*C07H 17/08* (2006.01)
*A61K 31/7048* (2006.01)

(52) U.S. Cl.
CPC ......... *C07H 17/08* (2013.01); *A61K 31/7048* (2013.01)

(58) Field of Classification Search
CPC .......................... C07H 17/08; A61K 31/7048
See application file for complete search history.

(56) References Cited

U.S. PATENT DOCUMENTS

| | | | |
|---|---|---|---|
| 4,201,843 A | 5/1980 | Fukumoto Tsumoru | |
| 4,205,163 A | 5/1980 | Mori et al. | |
| 4,345,069 A | 8/1982 | Sakakibara et al. | |
| 4,435,388 A | 3/1984 | Ganguly et al. | |
| 4,612,372 A | 9/1986 | Yoshioka et al. | |
| 4,808,575 A | 2/1989 | Mallams et al. | |
| 4,933,439 A | 6/1990 | Yoshioka et al. | |
| 5,240,849 A | 8/1993 | Arisawa et al. | |
| 2016/0200757 A1 | 7/2016 | von Geldern et al. | |

FOREIGN PATENT DOCUMENTS

| | | |
|---|---|---|
| JP | S5813595 A | 1/1983 |
| JP | 62234093 | 10/1987 |
| WO | 2016112317 A1 | 7/2016 |

OTHER PUBLICATIONS

Patani et al., Chem. Rev., 1996, 96, p. 3147-3176.*
Derwent Abstract of JP 5813595 A, published 1983. (Year: 1983).*
Google Translate of JP 5813595 A, https://translate.google.com, accessed online on Feb. 6, 2018. (Year: 2018).*
International Search Report and Written Opinion re: PCT/US2015/019718, dated Mar. 10, 2015.
Takeuchi, et al., "4"-O-(4-methoxyphenyl) acetyltylosin, a New Macrolide Derivative of Therapeutic Importance." The Journal of Antibiotics, vol. 40, No. 9, Sep. 1, 1987, pp. 1358-1360.
Yoshioka, et al., "Synthesis and Structure-Activity Studies of New 4"-O-acyltylosin Derivatives of Therapeutic Interest.", The Journal of Antibiotics, vol. 41, No. 11, Nov. 1, 1988, pp. 1617-1628.
Kiyoshima, K., "Application of the Dibutyltin Oxide Method to Regioselective Acylation and Alkylation of Tylosin at C-4''", Chemical & Pharmaceutical Bulletin, vol. 37, No. 4, Apr. 1, 1989, pp. 861-865.
Tsuchiya, M., et al., "Studies of Tylosin Derivatives Effective Against Macrolide-Resistant Strains: Synthesis and Structure-Activity Relationships", Journal of Antibiotics, Japan Antibiotics Research Association, Tokyo, JP, vol. 35, No. 6, Jan. 1, 1982, pp. 661-671.
Kiyoshima, K., et al., "Structure-Activity Relationship Studies On 4"-O-Acyltylosin Derivatives: Significance of Their 23-O-Mycinosyl and 4"-O-Acyl Moieties in Antimicrobial Activity Against Macrolide-Resistant Microbes", Journal of Antibiotics, Japan Antibiotics Research Association, Tokyo, JP, vol. 42, No. 11, Nov. 1989, pp. 1661-1672.
Cacciapuoti, et al., "Microbiological and Pharmacokinetic Studies of Acyl Demycinosyltylosin and Related Tylosin Derivatives"; The Journal of Antibiotics, vol. 43, No. 9, Sep. 1, 1990, pp. 1131-1136.
Narandja, Amalia, et al., "10, 11, 12, 13-Tetrahydro Derivatives of Tylosin; II. Synthesis, Antibacterial Activity and Tissue Distribution of 4'-Deoxy-10,11,12,13-tetrahydrodesmycosin", The Journal of Antibiotics, vol. 48, No. 3, Mar. 1, 1995, pp. 248-253.
Ose, E. E., "In Vitro Antibacterial Properties of EL-870, A New Semi-Synthetic Macrolide Antibiotic," The Journal of Antibiotics, vol. 40, No. 2, Feb. 1, 1987, pp. 190-194.
Terasawa, Tadashi, et al., "In Vitro Activity of YM133, a New Semisynthesized Macrolide," Antimicrobial Agents and Chemotherapy, vol. 35, No. 7, Jul. 1991, pp. 1370-1375.

* cited by examiner

*Primary Examiner* — Jonathan S Lau
(74) *Attorney, Agent, or Firm* — Neal, Gerber & Eisenberg LLP

(57) ABSTRACT

The present invention pertains to derivatives of tylosin A. In particular, the present invention pertains to compounds having a structure of Formula (I). The present invention also pertains to compositions comprising derivatives of tylosin A and methods of treating or preventing conditions or disorders using such compounds and compositions.

33 Claims, No Drawings

TYLOSIN A ANALOGS AND DERIVATIVES

CROSS-REFERENCE TO RELATED APPLICATIONS

This application claims priority to U.S. Provisional Application No. 61/951,179 filed Mar. 11, 2014 and U.S. Provisional Application No. 62/052,626 filed Sep. 19, 2014, the entire contents of which are incorporated herein by reference.

STATEMENT REGARDING FEDERALLY SPONSORED RESEARCH OR DEVELOPMENT

Not applicable.

TECHNICAL FIELD

The present invention relates to derivatives of tylosin A, compositions comprising such derivatives, and methods of treating or preventing conditions or disorders using such derivatives and compositions.

BACKGROUND

Tylosin A (2-((4R,5S,6S,7R,9R,11E,13E,15R,16R)-6-(((2R,3R,4R,5S,6R)-5-(((2S,4R,5S,6S)-4,5-dihydroxy-4,6-dimethyltetrahydro-2H-pyran-2-yl)oxy)-4-(dimethyl-amino)-3-hydroxy-6-methyltetrahydro-2H-pyran-2-yl)oxy)-16-ethyl-4-hydroxy-15-((((2R,3R,4R,5R,6R)-5-hydroxy-3,4-dimethoxy-6-methyltetrahydro-2H-pyran-2-yl)oxy)methyl)-5,9,13-trimethyl-2,10-dioxooxacyclohexadeca-11,13-dien-7-yl)acetaldehyde) is a macrolide antibiotic that is commonly used to treat veterinary infections. Tylosin A has a broad range of activity against Gram-positive organisms, with activity against a few Gram-negative species. Its high safety margin has led to its non-selective use as a food additive in meat production, and as a growth promoting agent. However, tylosin A and its derivatives have seen only limited use in companion animal health care. Tylvalosin, a derivative of tylosin, is available commercially as Aivlosin®. Aivlosin® is used for treating bacterial infections in farm animals. Neither tylosin A nor its derivatives are approved for use in human disease.

In part, the use of tylosin A and its analogs has been limited by their marginal pharmacokinetic profiles. Tylosin A has a relatively short half-life in vivo, and is poorly absorbed from an oral dose. The oral bioavailability of tylosin A in mammals is low. Thus, a tylosin A analog or derivative with improved pharmacokinetic properties would be a valuable addition to the treatment options for human and veterinary infections.

The mycarosyl group of Tylosin A can be cleaved to form desmycarosyl tylosin or tylosin B. Several groups have reported tylosin B analogs or derivatives with improved pharmacokinetic properties. Narandja et al. (J. Antibiotics 1995, 248) reported a derivative of tylosin B that gives tissue drug levels 2-3 times those of the parent. The commercial antibiotic tilmicosin (EL-870) is a semi-synthetic derivative of tylosin B and has been demonstrated to have a superior drug level profile when compared with the parent compound (Ose, E. E., J. Antibiotics 1987, 190). Tilmicosin is commercially available for prevention and treatment of bovine and ovine respiratory diseases associated with bacterial infection.

One particular challenge for the development of orally-bioavailable tylosin A derivatives is the susceptibility of tylosin esters (especially those derivatized at the 4"-position on the mycarose sugar) to hepatic esterases, as noted by Takeuchi et al. (J. Antibiotics 1987, 1358).

SUMMARY OF THE INVENTION

The present invention pertains to derivatives and analogs of tylosin A. In particular, the present invention pertains to compounds having a structure of Formula (I):

and salts thereof, wherein:

$R_1$ represents hydrogen or —C(O)$R_3$, wherein $R_3$ represents an optionally substituted $C_1$-$C_6$-alkyl or $C_1$-$C_6$-haloalkyl;

$R_2$ represents —C(O)C($R_4$)($R_5$)($R_6$), wherein each of $R_4$, $R_5$, and $R_6$ are independently selected from the group consisting of $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl; or $R_2$ represents —C(O)N($R_7$)($R_8$), wherein each of $R_7$ and $R_8$ are independently selected from the group consisting of hydrogen, $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl, or $R_7$ and $R_8$ together with the nitrogen atom to which they are attached form an optionally substituted saturated or partially saturated heterocyclic ring; or $R_2$ represents —CH$_2$-$A_1$, wherein $A_1$ represents a 6- to 10-membered aryl or a 5- to 10-membered heteroaryl and $A_1$ is unsubstituted or substituted with one or more $R_4$, wherein each $R_4$ is independently selected from the group consisting of halogen, $C_1$-$C_6$-alkyl, and $C_1$-$C_6$-haloalkyl;

$R_9$ represents hydrogen or —C(O)$R_{10}$, wherein $R_{10}$ represents an optionally substituted $C_1$-$C_6$-alkyl or $C_1$-$C_6$-haloalkyl;

each of a and b independently represents either a single bond or a double bond;

with the proviso that when both a and b are a double bond and $R_1$ and $R_9$ are both hydrogen, $A_1$ is not unsubstituted phenyl; and with the proviso that when both a and b are a double bond and $R_1$ and $R_9$ are both hydrogen or both C(O)CH$_3$, neither $R_7$ nor $R_8$ is hydrogen.

The present application discloses a general strategy for the preparation of tylosin A derivatives or analogs. In certain embodiments, the tylosin A derivatives or analogs have antibiotic activity and pharmacokinetic properties suitable for oral dosing. In certain embodiments, the tylosin A derivatives or analogs are modified at the 4"-hydroxyl group with an esterase-resistant substituent. In certain embodiments, such derivatives or analogs retain antibiotic activity, but demonstrate improved absorption and longer in vivo half-lives. In certain embodiments, these 4"-substituted tylosin A derivatives or analogs are, optionally, further modified through acylation of the 2'-hydroxyl. Thus, in certain embodiments, the resultant compounds have significantly improved pharmacokinetic properties, consistent with oral dosing, while retaining potent antibiotic activity against Gram-positive and some Gram-negative organisms.

Another aspect of the present invention pertains to pharmaceutical compositions comprising a therapeutically effective amount of a compound of Formula (I) or a pharmaceutically acceptable salt thereof in combination with one or more pharmaceutically acceptable carriers. In certain embodiments, such pharmaceutical compositions are administered to a subject in need thereof, typically as part of a therapeutic regimen for treatment or prevention of microbial infection. In certain embodiments, the pharmaceutical composition is suitable for human use. In certain embodiments, the pharmaceutical composition is suitable for veterinary use. In certain embodiments, such pharmaceutical compositions are used for the treatment or prevention of bacterial infection in a human. In certain embodiments, such pharmaceutical compositions are used for the treatment or prevention of bacterial infection in domesticated or semi-domesticated animals, such as poultry, honeybees, cows, sheep, goats, pigs, horses, dogs, cats, rabbits, rats, mice and the like.

Another aspect of the present invention pertains to the use of compounds of Formula (I) to treat or prevent a bacterial infection in a mammal. Compounds of Formula (I) exert antibacterial activity against various mammalian pathogens, including Gram-positive bacteria such as Staphylococci, Enterococci and Streptococi. In particular, compounds of Formula (I) exert antibacterial activity against Gram-positive bacteria such as *Staphylococcus aureus, Staphylococcus epidermidis, Enterococcus faecalis,* and *Streptococcus pneumoniae.* Compounds of Formula (I) exert antibacterial activity against Gram-negative bacteria such as *Haemophilus influenzae.*

Another aspect of the present invention pertains to methods for treating or preventing a bacterial infection in a subject in need of treatment or prevention of a bacterial infection. In certain embodiments, the methods comprise administering to the subject a therapeutically effective amount of a compound of Formula (I) or a pharmaceutically acceptable salt thereof.

Another aspect of the present invention pertains to kits that comprise a compound of Formula (I) or a pharmaceutically acceptable salt thereof, and, optionally, one or more additional therapeutic agents.

The compounds, pharmaceutical compositions comprising the compounds, and methods for treating or preventing conditions and disorders by administering the compounds are further described herein.

These and other objects of the invention are described in the following paragraphs. These objects should not be deemed to narrow the scope of the invention.

DETAILED DESCRIPTION OF THE INVENTION

This detailed description is intended only to acquaint others skilled in the art with the present invention, its principles, and its practical application so that others skilled in the art may adapt and apply the invention in its numerous forms, as they may be best suited to the requirements of a particular use. This description and its specific examples are intended for purposes of illustration only. This invention, therefore, is not limited to the embodiments described in this patent application, and may be variously modified.

Provided herein are compounds having the Formula (I):

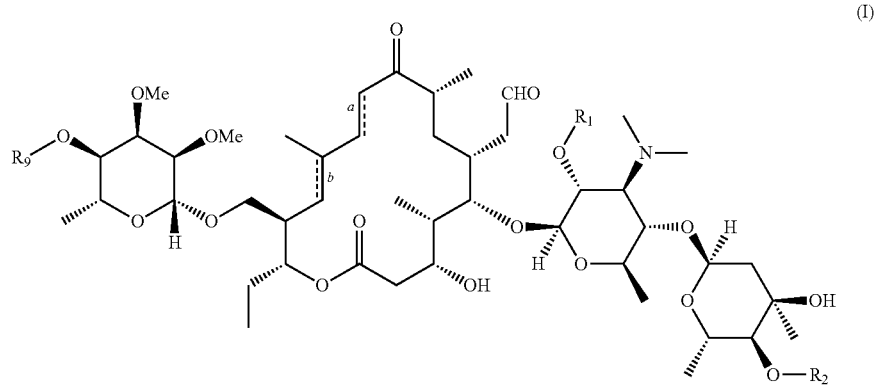

and salts thereof, wherein $R_1$, $R_2$, and $R_9$ are defined above in the Summary and below in the Detailed Description. Compositions comprising such compounds and methods for treating conditions and disorders using such compounds and compositions are also disclosed.

In various embodiments, there can be variables that occur more than one time in any substituent or in the compound or any other formulae herein. Definition of a variable on each occurrence is independent of its definition at another occurrence. Further, combinations of variables or substituents are permissible only if such combinations result in stable compounds. Stable compounds are compounds that can be isolated from a reaction mixture.

A. Definitions

As used in the specification and the appended claims, unless specified to the contrary, the following terms have the meaning indicated:

The term "acyl" means an alkyl group, as defined herein, appended to the parent molecular moiety through a carbonyl group, as defined herein. Representative examples of acyl include, but are not limited to, acetyl, 1-oxopropyl, 2,2-dimethyl-1-oxopropyl, 1-oxobutyl, and 1-oxopentyl.

The term "alkenyl" means a straight or branched hydrocarbon chain containing one or more carbon-carbon double bonds and, typically, from 2 to 10 carbon atoms. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" means a straight or branched saturated hydrocarbon chain, typically containing from 1 to 10 carbon atoms. Representative examples of alkyl include, but are not limited to, methyl, ethyl, n-propyl, isopropyl, n-butyl, isobutyl, sec-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "lower alkyl" or "$C_1$-$C_6$-alkyl" means a straight or branched hydrocarbon chain containing from 1 to 6 carbon atoms. In some instances, the number of carbon atoms in a hydrocarbon substituent (e.g., alkyl, alkenyl, alkynyl, or cycloalkyl) is indicated by the prefix "$C_x$-$C_y$—", wherein x is the minimum and y is the maximum number of carbon atoms in the substituent. Thus, for example, "$C_1$-$C_6$-alkyl" refers to an alkyl substituent containing from 1 to 6 carbon atoms. Likewise, "$C_3$-$C_8$-cycloalkyl" refers to a cycloalkyl substituent containing from 3 to 8 carbon atoms.

The term "alkylene" means a divalent group derived from a straight or branched hydrocarbon chain, typically containing 1 to 10 carbon atoms. Representative examples of alkylene include, but are not limited to, —$CH_2$—, —$CH_2CH_2$—, —$CH_2CH_2CH_2$—, —$CH_2CH_2CH_2CH_2$—, and —$CH_2CH(CH_3)CH_2$—.

The term "alkynyl" means a straight or branched hydrocarbon chain containing one or more carbon-carbon triple bonds and, typically, from 2 to 10 carbon atoms. Representative examples of alkynyl include, but are not limited to, ethynyl, 2-propynyl, 3-propynyl, 2-butynyl, and 3-butynyl and the like.

The term "aryl" means an aromatic carbocyclyl containing from 6 to 14 carbon ring atoms. An aryl may be monocyclic or polycyclic (i.e., may contain more than one ring). In the case of a polycyclic aryl, only one ring of the polycyclic system is required to be aromatic while the remaining ring(s) may be saturated, partially saturated or unsaturated. Representative examples of aryl include, but are not limited to, phenyl, naphthalenyl, indenyl, indanyl, and tetrahydronapthyl. Unless otherwise specified herein, the aryl groups can be substituted or unsubstituted. Thus, the hydrogen atoms of the aryl groups may be optionally substituted by one or more substituents, including, but not limited to, acyl, alkenyl, alkoxy, alkyl, alkynyl, carboxy, haloalkyl, halogen, hydroxy, and hydroxyalkyl.

The term "arylalkyl" means an aryl group, as defined herein, appended to the parent molecular moiety through an alkylene group, as defined herein. Representative examples of arylalkyl include, but are not limited to, benzyl, 2-phenylethyl, 3-phenylpropyl, and 2-naphth-2-ylethyl.

The term "AUC(0-∞)" refers to the area under the plasma concentration time curve (AUC) extrapolated to infinity.

The term "carbocyclyl" means a saturated cyclic, partially saturated cyclic, or completely unsaturated cyclic hydrocarbyl substituent containing from 3 to 14 carbon ring atoms ("ring atoms" are the atoms bound together to form the ring or rings of a cyclic substituent). A carbocyclyl may be a single-ring (monocyclic) or polycyclic ring structure.

The term "carbonyl" means a —C(O)— group.

The term "carboxy" means a —$CO_2H$ group.

The term "cycloalkyl" means a saturated cyclic hydrocarbyl substituent containing from 3 to 14 carbon ring atoms. A cycloalkyl may be a single carbon ring, which typically contains from 3 to 8 carbon ring atoms and more typically from 3 to 6 ring atoms. Examples of single-ring cycloalkyls include, but are not limited to, cyclopropyl, cyclobutyl, cyclopentyl, and cyclohexyl. A cycloalkyl may alternatively be polycyclic or contain more than one ring. Examples of polycyclic cycloalkyls include bridged, fused, and spirocyclic carbocyclyls. Unless otherwise specified herein, the cycloalkyl groups can be substituted or unsubstituted. Thus, the hydrogen atoms of the cycloalkyl groups may be optionally substituted by one or more substituents, including, but not limited to, acyl, alkenyl, alkoxy, alkyl, alkynyl, carboxy, haloalkyl, halogen, hydroxy, and hydroxyalkyl.

The term "cycloalkylalkyl" means a cycloalkyl group, as defined herein, appended to the parent molecular moiety through an alkylene group, as defined herein. Representative examples of cycloalkylalkyl include, but are not limited to, cyclopropylmethyl, 2-cyclobutylethyl, cyclopentylmethyl, cyclohexylmethyl, and 4-cycloheptylbutyl.

The term "halo" or "halogen" means an atom selected from fluorine, chlorine, bromine, and iodine.

The term "haloalkyl" means an alkyl group, as defined herein, in which one or more hydrogen atoms are replaced by halogen. Representative examples of haloalkyl include, but are not limited to, chloromethyl, 2-fluoroethyl, 2,2,2-trifluoroethyl, trifluoromethyl, difluoromethyl, pentafluoroethyl, 2-chloro-3-fluoropentyl, and trifluoropropyl such as 3,3,3-trifluoropropyl.

The term "heteroaryl" means an aromatic heterocyclyl containing from 5 to 14 ring atoms. A heteroaryl may be monocyclic or polycyclic (i.e., may contain more than one ring). In the case of a polycyclic heteroaryl, only one ring of the polycyclic system is required to be aromatic while the remaining ring(s) may be saturated, partially saturated or unsaturated. Representative examples of heteroaryl include, but are not limited to, 6-membered ring substituents such as pyridyl, pyrazyl, pyrimidinyl, pyridazinyl; 5-membered ring substituents such as imidazyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl; fused ring substituents such as benzothiazolyl, benzothiofuranyl, benzisoxazolyl, benzoxazolyl, purinyl; benzopyranyl, quinolinyl, isoquinolinyl, cinnolinyl, quinazolinyl, and benzoxazinyl. Unless otherwise specified herein, the heteroaryl groups can be substituted or unsubstituted. Thus, the hydrogen atoms of the heteroaryl groups may be optionally substituted by one or more substituents, including, but not limited to, acyl, alkenyl, alkoxy, alkyl, alkynyl, carboxy, haloalkyl, halogen, hydroxy, and hydroxyalkyl.

The term "heteroarylalkyl" means a heteroaryl, as defined herein, appended to the parent molecular moiety through an alkylene group, as defined herein. Representative examples of heteroarylalkyl include, but are not limited to, fur-3-ylmethyl, 1H-imidazol-2-ylmethyl, 1H-imidazol-4-ylmethyl, 1-(pyridin-4-yl)ethyl, pyridin-3-ylmethyl, 6-chloro-pyridin-3-ylmethyl, pyridin-4-ylmethyl, (6-(trifluoromethyl)pyridin-3-yl)methyl, (6-(cyano)pyridin-3-yl)methyl, (2-(cyano)pyridin-4-yl)methyl, (5-(cyano)pyridin-2-yl)methyl, (2-(chloro)pyridin-4-yl)methyl, pyrimidin-5-ylmethyl, 2-(pyrimidin-2-yl)propyl, thien-2-ylmethyl, and thien-3-ylmethyl.

The term "heteroatom" means a nitrogen, oxygen, or sulfur atom.

The term "heterocycloalkyl" means a saturated heterocyclyl. Unless otherwise specified herein, the heterocycloalkyl groups can be substituted or unsubstituted. Thus, the hydrogen atoms of the heterocycloalkyl groups may be optionally substituted by one or more substituents, including, but not limited to, acyl, alkenyl, alkoxy, alkyl, alkynyl, carboxy, haloalkyl, halogen, hydroxy, and hydroxyalkyl.

The term "heterocyclyl" or "heterocyclic" means a saturated, partially saturated, or completely unsaturated ring structure containing a total of 3 to 14 ring atoms, where at least one of the ring atoms is a heteroatom (i.e., oxygen, nitrogen, or sulfur), with the remaining ring atoms being independently selected from the group consisting of carbon, oxygen, nitrogen, and sulfur. A heterocyclic ring may be a single-ring (monocyclic) or polycyclic ring structure. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl.

The term "hydroxyl" or "hydroxy" means an —OH group.

The term "hydroxyalkyl" means at least one hydroxy group, as defined herein, is appended to the parent molecular moiety through an alkylene group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

If a particular substituent is described as being "substituted", it means that there are one or more substituents other than hydrogen attached to that particular substituent. Thus, for example, a substituted alkyl is an alkyl in which at least one non-hydrogen substituent is in the place of a hydrogen atom on the alkyl. If a particular substituent is described as being "optionally substituted", that particular substituent may be either (1) not substituted or (2) substituted.

The terms "treat", "treating" and "treatment" refer to a method of alleviating or abrogating a condition, disorder, or disease and/or the attendant symptoms thereof.

The terms "prevent", "preventing" and "prevention" refer to a method of preventing the onset of a condition, disorder, or disease and/or the attendant symptoms thereof or barring a subject from acquiring a condition, disorder, or disease. As used herein, "prevent", "preventing" and "prevention" also include delaying the onset of a condition, disorder, or disease and/or the attendant symptoms thereof and reducing a subject's risk of acquiring a condition, disorder, or disease.

The term "pharmaceutically acceptable" is used adjectivally to mean that the modified noun is appropriate for use as a pharmaceutical product or as a part of a pharmaceutical product.

The term "therapeutically effective amount" means a sufficient amount of the compound to treat a condition, disorder, or disease, at a reasonable benefit/risk ratio applicable to any medical treatment. When used in a medical treatment, a therapeutically effective amount of one of the present compounds can be employed in pure form or, where such forms exist, in pharmaceutically acceptable salt or ester, or amide form. Alternatively, the compound can be administered as a pharmaceutical composition containing the compound of interest in combination with one or more pharmaceutically acceptable carriers.

The term "subject" includes humans and other primates as well as domesticated and semi-domesticated animals including, but not limited to, poultry, honeybees, cows, sheep, goats, pigs, horses, dogs, cats, rabbits, rats, mice and the like. The term "poultry" encompasses all types of domestic fowl, including, but not limited to chickens, turkey, ducks, geese, the ratite group of birds and game birds. In certain embodiments, the subject is a human.

B. Compounds

In one aspect, the present invention includes compounds of Formula (I) and salts thereof as described above in the Summary and throughout the Detailed Description.

In certain embodiments, $R_1$ is hydrogen.

In certain embodiments, $R_1$ is —C(O)$R_3$. In certain embodiments, $R_3$ is $C_1$-$C_6$-alkyl, such as methyl; ethyl; propyl, such as n-propyl or isopropyl; or butyl, such as n-butyl, isobutyl, or tert-butyl. In certain embodiments, $R_3$ is substituted. Substituents of $R_3$ may include, but are not limited to aryl, heteroaryl, cycloalkyl, or heterocycloalkyl.

In certain embodiments, $R_2$ is —C(O)C($R_4$)($R_5$)($R_6$). Each of $R_4$, $R_5$, and $R_6$ are independently selected from the group consisting of $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl. In certain embodiments, $R_4$ is $C_1$-$C_6$ alkyl. In certain embodiments, $R_5$ is $C_1$-$C_6$ alkyl. In certain embodiments, $R_6$ is $C_1$-$C_6$ alkyl. In certain embodiments, each of $R_4$, $R_5$, and $R_6$ are $C_1$-$C_6$ alkyl.

In certain embodiments, $R_4$, $R_5$, and $R_6$ are the same. For example, in certain embodiments, each of $R_4$, $R_5$, and $R_6$ are methyl. In certain embodiments, at least two of $R_4$, $R_5$, and $R_6$ are the same. In certain embodiments, $R_4$, $R_5$, and $R_6$ are different.

In certain embodiments, $R_2$ is —C(O)N($R_7$)($R_8$). In certain embodiments, each of $R_7$ and $R_8$ are independently selected from the group consisting of $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl. In certain embodiments, $R_7$ and $R_8$ together with the nitrogen atom to which they are attached form an optionally substituted saturated or partially saturated heterocyclic ring. For instance $R_7$ and $R_8$, taken together with the atoms to which they are attached, can form, without limitation, an optionally substituted saturated heterocyclic ring such as

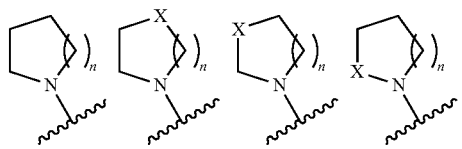

where X is O, S, or N($R_B$). $R_B$ is selected from hydrogen, $C_1$-$C_6$-alkyl, $C_2$-$C_6$-alkenyl, or $C_2$-$C_6$-alkynyl and n is 0, 1, 2, or 3.

In certain embodiments, $R_2$ is —$CH_2$-$A_1$ and $A_1$ is a 6- to 10-membered aryl or a 5- to 10-membered heteroaryl. In certain embodiments, $A_1$ is phenyl, pyrazinyl, pyridinyl, pyrimidinyl, pyridazinyl, oxazolyl, thiazolyl, thienyl, furanyl, imidazolyl, pyrazolyl, triazolyl, benzoxazolyl, benzothienyl, benzimidazolyl, benzofuranyl, benzothiazolyl, indolyl, indenyl, naphthalenyl, quinolinyl, isoquinolinyl, quinoxalinyl, cinnolinyl, quinazolinyl, or phthalazinyl; each of which is optionally substituted. In certain embodiments, $A_1$ is

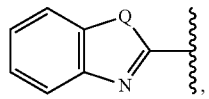

where Q is O, S, or N($R_C$). $R_C$ is selected from hydrogen; $C_1$-$C_6$-alkyl, or $C_1$-$C_6$-haloalkyl.

In certain embodiments, $A_1$ is unsubstituted. In certain embodiments, $A_1$ is substituted with one or more $R_4$. In certain embodiments, $R_A$ is halogen, $C_1$-$C_6$-alkyl, or $C_1$-$C_6$-haloalkyl.

In certain embodiments, $R_1$ is —C(O)$R_3$ and $R_3$ is $C_1$-$C_6$-alkyl. In certain embodiments, $R_3$ is methyl. In certain embodiments, $R_3$ is propyl. In certain embodiments, $R_3$ is n-propyl. In certain embodiments, $R_3$ is isopropyl. In certain embodiments, $R_3$ is butyl. In certain embodiments, $R_3$ is n-butyl. In certain embodiments, $R_3$ is isobutyl. In certain embodiments, $R_3$ is tert-butyl.

In certain embodiments, $R_2$ is —C(O)C($R_4$)($R_5$)($R_6$) and each of $R_4$, $R_5$, and $R_6$ are $C_1$-$C_6$ alkyl. In certain embodiments, $R_4$ is methyl. In certain embodiments, $R_5$ is methyl. In certain embodiments, $R_6$ is methyl. In certain embodiments, each of $R_4$, $R_5$, and $R_6$ are methyl.

In certain embodiments, $R_2$ is —C(O)N($R_7$)($R_8$) and one or both of $R_7$ or $R_8$ are $C_1$-$C_6$ alkyl. In certain embodiments, one or both of $R_7$ or $R_8$ are methyl. In certain embodiments, one or both of $R_7$ or $R_8$ are ethyl. In certain embodiments, one or both of $R_7$ or $R_8$ are propyl, such as n-propyl or isopropyl. In certain embodiments, one or both of $R_7$ or $R_8$ are butyl, such as n-butyl, isobutyl, or sec-butyl.

In certain embodiments, $R_2$ is —C(O)N($R_7$)($R_8$) and each of $R_7$ and $R_8$ are $C_1$-$C_6$ alkyl. In certain embodiments, both of $R_7$ and $R_8$ are methyl. In certain embodiments, both of $R_7$ and $R_8$ are ethyl. In certain embodiments, both of $R_7$ and $R_8$ are propyl, such as n-propyl or isopropyl. In certain embodiments, both of $R_7$ and $R_8$ are butyl, such as n-butyl, isobutyl, or sec-butyl. In certain embodiments, one of $R_7$ or $R_8$ is butyl and the other of $R_7$ or $R_8$ is ethyl.

In certain embodiments, $R_2$ is —C(O)N($R_7$)($R_8$) and one or both of $R_7$ or $R_8$ are $C_3$-$C_8$-cycloalkyl. In certain embodiments, both of $R_7$ and $R_8$ are $C_3$-$C_8$-cycloalkyl. In certain embodiments, both of $R_7$ and $R_8$ are cyclohexyl.

In certain embodiments, $R_2$ is —C(O)N($R_7$)($R_8$) and one or both of $R_7$ or $R_8$ are aryl. In certain embodiments, one or both of $R_7$ or $R_8$ are phenyl. In certain embodiments, one or both of $R_7$ or $R_8$ are unsubstituted phenyl.

In certain embodiments, $R_2$ is —C(O)N($R_7$)($R_8$) and one of $R_7$ or $R_8$ is $C_1$-$C_6$ alkyl and the other of $R_7$ or $R_8$ is aryl. In certain embodiments, one of $R_7$ or $R_8$ is phenyl and the other of $R_7$ or $R_8$ is methyl or ethyl. In certain embodiments, one of $R_7$ or $R_8$ is unsubstituted phenyl and the other of $R_7$ or $R_8$ is methyl.

In certain embodiments, $R_2$ is dialkyl carbamoyl. In certain embodiments, $R_2$ is dimethyl carbamoyl. In certain embodiments, $R_2$ is diethyl carbamoyl. In certain embodiments, $R_2$ is dipropyl carbamoyl. In certain embodiments, $R_2$ is di(propan-2-yl)carbamoyl. In certain embodiments, $R_2$ is dibutyl carbamoyl. In certain embodiments, $R_2$ is bis(2-methylpropyl)carbamoyl. In certain embodiments, $R_2$ is N-butyl-N-ethylcarbamoyl.

In certain embodiments, $R_2$ is N-methyl-N-phenylcarbamoyl.

In certain embodiments, $R_2$ is dicyclohexylcarbamoyl.

In certain embodiments, $R_2$ is —C(O)N($R_7$)($R_8$) and $R_7$ and $R_8$ together with the nitrogen atom to which they are attached form an optionally substituted saturated or partially saturated heterocyclic ring. In certain embodiments, the heterocyclic ring is a non-aromatic ring. In certain embodiments, the heterocyclic ring is a pyrrolidine. In certain embodiments, the heterocyclic ring is a piperidine. In certain embodiments, the heterocyclic ring is a morpholine. In certain embodiments, the heterocyclic ring is an azepane.

In certain embodiments, $R_2$ is —$CH_2$-$A_1$.

In certain embodiments, $A_1$ is an unsubstituted phenyl. In certain embodiments, $R_2$ is unsubstituted benzyl.

In certain embodiments, $A_1$ is a phenyl substituted with one or more $R_A$. In certain embodiments, $R_A$ is haloalkyl. In certain embodiments, $R_A$ is trifluoromethyl. In certain embodiments, $R_A$ is halogen. In certain embodiments, $R_A$ is fluoro. In certain embodiments, $R_A$ is chloro. In certain embodiments, $R_2$ is substituted benzyl. In certain embodiments, $R_2$ is trifluoromethylbenzyl. In certain embodiments, $R_2$ is trifluorobenzyl. In certain embodiments, $R_2$ is fluorobenzyl. In certain embodiments, $R_2$ is difluorobenzyl. In certain embodiments, $R_2$ is chlorobenzyl.

In certain embodiments, $A_1$ is naphthalene. In certain embodiments, $A_1$ is benzothiazole.

In certain embodiments, $R_9$ is —C(O)$R_{10}$. In certain embodiments, $R_{10}$ is $C_1$-$C_6$-alkyl, such as methyl; ethyl; propyl, such as n-propyl or isopropyl; or butyl, such as n-butyl, isobutyl, or tert-butyl.

In certain embodiments, both a and b are a double bond. In certain embodiments, at least one of a and b are a single bond. In certain embodiments, both a and b are a single bond.

In certain embodiments, $R_1$ is —C(O)$CH_3$ and $R_2$ is benzyl.

In certain embodiments, $R_1$ is —C(O)$CH_3$ and $R_2$ is

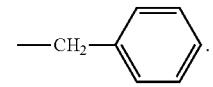

In certain embodiments, $R_1$ is —C(O)$CH_3$ and $R_2$ is trifluoromethylbenzyl.

In certain embodiments, $R_1$ is —C(O)$CH_3$ and $R_2$ is

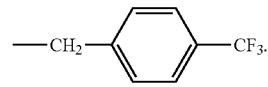

In certain embodiments, $R_1$ is —C(O)$CH_3$ and $R_2$ is fluorobenzyl.

In certain embodiments, $R_1$ is —C(O)CH$_3$ and $R_2$ is

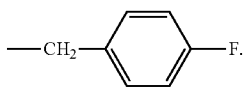

In certain embodiments, $R_1$ is —C(O)CH$_3$ and $R_2$ is chlorobenzyl.

In certain embodiments, $R_1$ is —C(O)CH$_3$ and $R_2$ is

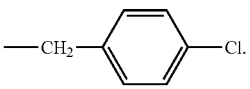

In certain embodiments, $R_1$ is —C(O)CH(CH$_3$)$_2$ and $R_2$ is benzyl.

In certain embodiments, $R_1$ is —C(O)CH(CH$_3$)$_2$ and $R_2$ is

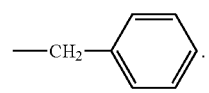

In certain embodiments, $R_1$ is —C(O)CH(CH$_3$)$_2$ and $R_2$ is difluorobenzyl.

In certain embodiments, $R_1$ is —C(O)CH(CH$_3$)$_2$ and $R_2$ is

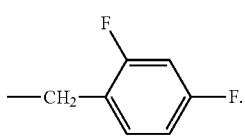

In certain embodiments, $R_1$ is —C(O)CH(CH$_3$)$_2$ and $R_2$ is CH$_2$-benzothiazolyl.

In certain embodiments, $R_1$ is —C(O)CH(CH$_3$)$_2$ and $R_2$ is

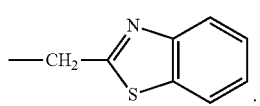

In certain embodiments, $R_1$ is —C(O)CH(CH$_3$)$_2$ and $R_2$ is fluorobenzyl.

In certain embodiments, $R_1$ is —C(O)CH(CH$_3$)$_2$ and $R_2$ is

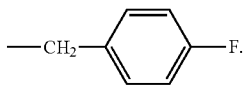

In certain embodiments, $R_1$ is —C(O)CH(CH$_3$)$_2$ and $R_2$ is CH$_2$-naphthalenyl.

In certain embodiments, $R_1$ is —C(O)CH(CH$_3$)$_2$ and $R_2$ is

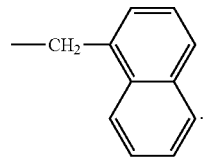

In certain embodiments, $R_1$ is hydrogen and $R_2$ is fluorobenzyl.

In certain embodiments, $R_1$ is hydrogen and $R_2$ is

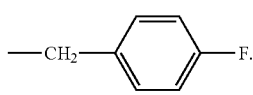

In certain embodiments, $R_1$ is —C(O)(CH$_2$)$_3$CH$_3$ and $R_2$ is fluorobenzyl.

In certain embodiments, $R_1$ is —C(O)(CH$_2$)$_3$CH$_3$ and $R_2$ is

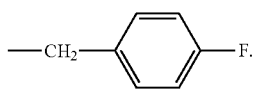

In certain embodiments, $R_1$ is —C(O)CH$_3$ and $R_2$ is —C(O)C(CH$_3$)$_3$.

In certain embodiments, $R_1$ is —C(O)CH(CH$_3$)$_2$ and $R_2$ is —C(O)C(CH$_3$)$_3$.

In certain embodiments, $R_1$ is hydrogen and $R_2$ is —C(O)C(CH$_3$)$_3$.

In certain embodiments, $R_1$ is —C(O)CH$_3$ and $R_2$ is —C(O)N(CH$_2$CH$_3$)$_2$.

In certain embodiments, $R_1$ is —C(O)CH$_3$ and $R_2$ is N-methyl-N-phenylcarbamoyl.

In certain embodiments, $R_1$ is —C(O)CH$_3$ and $R_2$ is —C(O)N(CH$_3$)(C$_6$H$_5$).

In certain embodiments, $R_1$ is —C(O)CH$_3$ and $R_2$ is —C(O)-pyrrolidinyl.

In certain embodiments, $R_1$ is —C(O)CH$_3$ and $R_2$ is

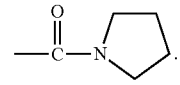

In certain embodiments, $R_1$ is —C(O)CH(CH$_3$)$_2$ and $R_2$ is —C(O)N(CH$_2$CH$_3$)$_2$.

In certain embodiments, $R_1$ is hydrogen and $R_2$ is —C(O)N(CH$_2$CH$_3$)$_2$.

In certain embodiments, $R_1$ is —C(O)CH$_3$ and $R_2$ is —C(O)-piperidinyl.

In certain embodiments, $R_1$ is —C(O)CH$_3$ and $R_2$ is

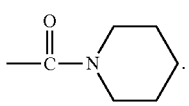

In certain embodiments, $R_1$ is —C(O)CH$_3$ and $R_2$ is —C(O)-morpholinyl.

In certain embodiments, $R_1$ is —C(O)CH$_3$ and $R_2$ is

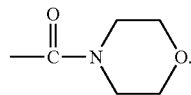

In certain embodiments, $R_1$ is —C(O)CH$_3$ and $R_2$ is —C(O)N(CH(CH$_3$)$_2$)$_2$.
In certain embodiments, $R_1$ is —C(O)CH$_3$ and $R_2$ is —C(O)N((CH$_2$)$_3$CH$_3$)$_2$.
In certain embodiments, $R_1$ is —C(O)CH$_3$ and $R_2$ is —C(O)N(CH$_2$CH(CH$_3$)$_2$)$_2$.
In certain embodiments, $R_1$ is —C(O)CH$_3$ and $R_2$ is —C(O)-azepane.
In certain embodiments, $R_1$ is —C(O)CH$_3$ and $R_2$ is

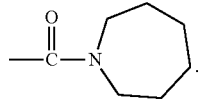

In certain embodiments, $R_1$ is —C(O)CH$_3$ and $R_2$ is dicyclohexylcarbamoyl.
In certain embodiments, $R_1$ is —C(O)CH$_3$ and $R_2$ is

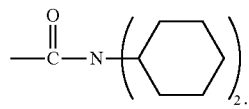

In certain embodiments, $R_1$ is —C(O)CH(CH$_3$)$_2$ and $R_2$ is —C(O)N(CH$_3$)$_2$.
In certain embodiments, $R_1$ is —C(O)CH(CH$_3$)$_2$ and $R_2$ is N-butyl-N-ethylcarbamoyl.
In certain embodiments, $R_1$ is —C(O)CH(CH$_3$)$_2$ and $R_2$ is —C(O)N(CH$_2$CH$_3$)((CH$_2$)$_3$CH$_3$).
In certain embodiments, $R_1$ is hydrogen and $R_2$ is —C(O)N(CH(CH$_3$)$_2$)$_2$.
In certain embodiments, $R_1$ is hydrogen and $R_2$ is —C(O)N((CH$_2$)$_3$CH$_3$)$_2$.
In certain embodiments, $R_1$ is hydrogen and $R_2$ is dicyclohexylcarbamoyl.
In certain embodiments, $R_1$ is H and $R_2$ is

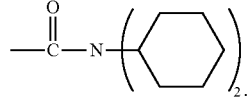

In certain embodiments, $R_1$ is —C(O)CH(CH$_3$)$_2$ and $R_2$ is —C(O)-morpholinyl.
In certain embodiments, $R_1$ is —C(O)CH(CH$_3$)$_2$ and $R_2$ is

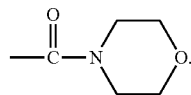

In certain embodiments, $R_1$ is —C(O)CH$_3$ and $R_2$ is difluorobenzyl.

In certain embodiments, $R_1$ is —C(O)CH$_3$ and $R_2$ is

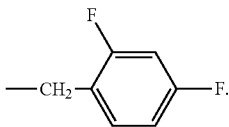

In certain embodiments, $R_1$ is —C(O)(CH$_2$)$_3$(CH$_3$) and $R_2$ is —C(O)-morpholinyl.
In certain embodiments, $R_1$ is —C(O)(CH$_2$)$_3$(CH$_3$) and $R_2$ is

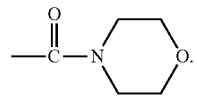

In certain embodiments, $R_1$ is —C(O)(CH$_2$)$_3$(CH$_3$) and $R_2$ is difluorobenzyl.
In certain embodiments, $R_1$ is —C(O)(CH$_2$)$_3$(CH$_3$) and $R_2$ is

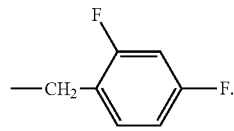

In certain embodiments, $R_1$ is hydrogen and $R_2$ is —C(O)-morpholinyl.
In certain embodiments, $R_1$ is H and $R_2$ is

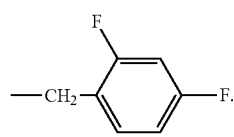

In certain embodiments, $R_1$ is hydrogen and $R_2$ is difluorobenzyl.
In certain embodiments, $R_1$ is H and $R_2$ is

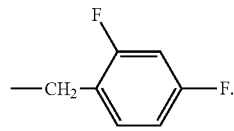

In certain embodiments, $R_1$ is hydrogen and $R_9$ is C(O)CH$_2$CH$_3$.
In certain embodiments, $R_1$ is C(O)CH$_2$CH$_3$ and $R_9$ is C(O)CH$_2$CH$_3$.
In certain embodiments, $R_1$ is C(O)CH$_3$ and $R_9$ is C(O)CH$_2$CH$_3$.
In certain embodiments, $R_2$ is —C(O)N(CH$_2$CH$_3$)$_2$ and $R_9$ is C(O)CH$_2$CH$_3$.
In certain embodiments, $R_2$ is halobenzyl and $R_9$ is C(O)CH$_2$CH$_3$.
In certain embodiments, $R_2$ is fluorobenzyl and $R_9$ is C(O)CH$_2$CH$_3$.

In certain embodiments, $R_2$ is

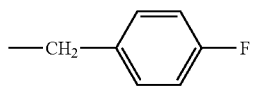

and $R_9$ is $C(O)CH_2CH_3$.

In one aspect, the present invention includes compounds of Formula (II):

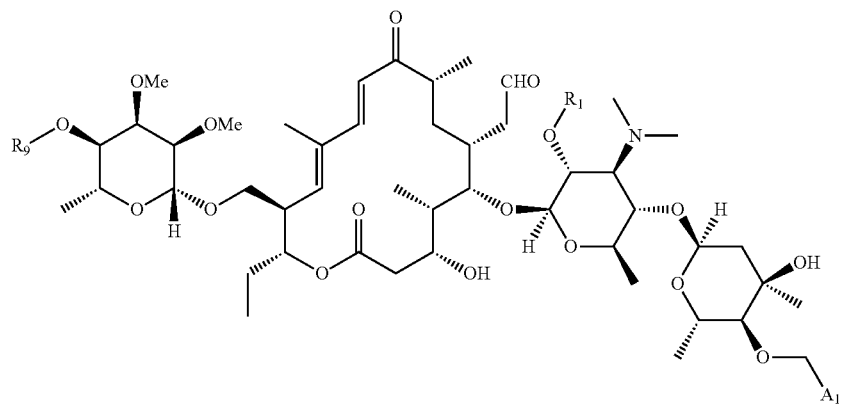

and salts thereof, wherein:

$R_1$ represents hydrogen or —$C(O)R_3$, where $R_3$ represents an optionally substituted $C_1$-$C_6$-alkyl or $C_1$-$C_6$-haloalkyl;

$A_1$ represents a phenyl substituted with one or more $R_4$, a 7- to 10-membered aryl optionally substituted with one or more $R_4$, or a 5- to 10-membered heteroaryl optionally substituted with one or more $R_4$, where each $R_4$ is independently selected from the group consisting of halogen, $C_1$-$C_6$-alkyl, and $C_1$-$C_6$-haloalkyl; and $R_9$ represents hydrogen or —$C(O)R_{10}$, wherein $R_{10}$ represents an optionally substituted $C_1$-$C_6$-alkyl or $C_1$-$C_6$-haloalkyl.

In certain embodiments, $R_1$ is hydrogen.

In certain embodiments, $R_1$ is —$C(O)R_3$. In certain embodiments, $R_3$ is $C_1$-$C_6$-alkyl, such as methyl; ethyl; propyl, such as n-propyl or isopropyl; or butyl, such as n-butyl, isobutyl, or tert-butyl. In certain embodiments, $R_3$ is substituted. Substituents of $R_3$ may include, but are not limited to aryl, heteroaryl, cycloalkyl, or heterocycloalkyl.

In certain embodiments, $A_1$ is a phenyl substituted with one or more $R_4$. In certain embodiments, $R_4$ is halogen. In certain embodiments, $A_1$ is a halophenyl or a dihalophenyl. In certain embodiments, $A_1$ is a 7- to 10-membered aryl optionally substituted with one or more $R_4$. In certain embodiments, $A_1$ is a 5- to 10-membered heteroaryl optionally substituted with one or more $R_4$. Each $R_4$ is independently selected from the group consisting of halogen, $C_1$-$C_6$-alkyl, and $C_1$-$C_6$-haloalkyl. In certain embodiments, $A_1$ is substituted phenyl or an optionally substituted pyrazinyl, pyridinyl, pyrimidinyl, pyridazinyl, oxazolyl, thiazolyl, thienyl, furanyl, imidazolyl, pyrazolyl, triazolyl, benzoxazolyl, benzothienyl, benzimidazolyl, benzofuranyl, benzothiazolyl, indolyl, indenyl, naphthalenyl, quinolinyl, isoquinolinyl, quinoxalinyl, cinnolinyl, quinazolinyl, or phthalazinyl; each of which is optionally substituted. In certain embodiments, $A_1$ is

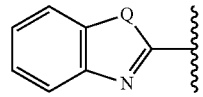

where Q is O, S, or $N(R_C)$. $R_C$ is selected from hydrogen; $C_1$-$C_6$-alkyl, or $C_1$-$C_6$-haloalkyl.

In certain embodiments, $A_1$ is substituted with one or more $R_4$. $R_4$ is independently selected at each occurrence (II)

from halogen, $C_1$-$C_6$-alkyl, and $C_1$-$C_6$-haloalkyl. In certain embodiments, $R_4$ is halogen. In certain embodiments, $R_4$ is fluoro. In certain embodiments, $R_4$ is chloro.

In certain embodiments, $A_1$ is a phenyl substituted with one or more $R_4$. In certain embodiments, $R_4$ is haloalkyl. In certain embodiments, $R_4$ is trifluoromethyl. In certain embodiments, $R_4$ is halogen. In certain embodiments, $R_4$ is fluoro. In certain embodiments, $R_4$ is chloro. In certain embodiments, $A_1$ is fluorophenyl. In certain embodiments, $A_1$ is chlorophenyl.

In certain embodiments, $A_1$ is a phenyl substituted with two or more $R_4$. In certain embodiments, each of the two or more $R_4$ is halogen. In certain embodiments, each of the two or more $R_4$ is fluoro. In certain embodiments, each of the two or more $R_4$ is chloro. In certain embodiments, $A_1$ is dihalophenyl. In certain embodiments, $A_1$ is difluorophenyl. In certain embodiments, $A_1$ is dichlorophenyl.

In certain embodiments, $A_1$ is a 7- to 10-membered aryl optionally substituted with one or more $R_4$. In certain embodiments, $A_1$ is naphthalene.

In certain embodiments, $A_1$ is a 5- to 10-membered heteroaryl optionally substituted with one or more $R_4$. In certain embodiments, $A_1$ is benzothiazole.

In certain embodiments, $R_9$ is —$C(O)R_{10}$. In certain embodiments, $R_{10}$ is $C_1$-$C_6$-alkyl, such as methyl; ethyl; propyl, such as n-propyl or isopropyl; or butyl, such as n-butyl, isobutyl, or tert-butyl. In certain embodiments, $R_9$ is substituted. Substituents of $R_9$ may include, but are not limited to aryl, heteroaryl, cycloalkyl, or heterocycloalkyl.

In one aspect, the present invention includes compounds of Formula (III):

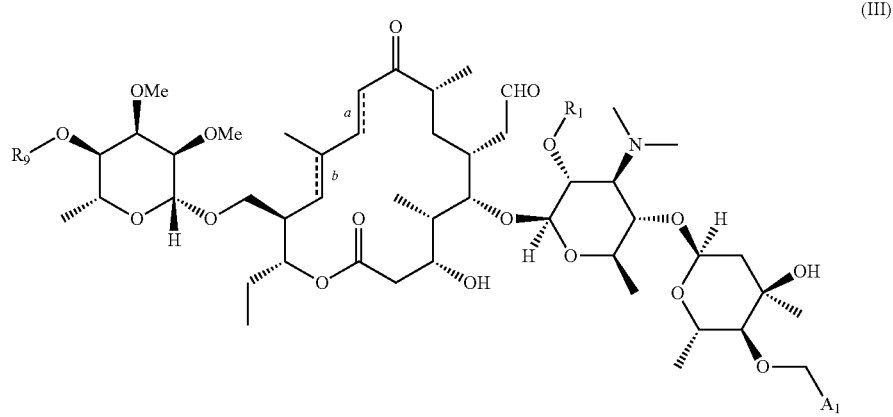

(III)

and salts thereof, wherein:

$R_1$ represents hydrogen or —C(O)$R_3$, where $R_3$ represents an optionally substituted $C_1$-$C_6$-alkyl or $C_1$-$C_6$-haloalkyl;

$A_1$ represents a 6- to 10-membered aryl or a 5- to 10-membered heteroaryl and $A_1$ is unsubstituted or substituted with one or more $R_4$, wherein each $R_4$ is independently selected from the group consisting of halogen, $C_1$-$C_6$-alkyl, and $C_1$-$C_6$-haloalkyl;

$R_9$ represents hydrogen or —C(O)$R_{10}$, wherein $R_{10}$ represents an optionally substituted $C_1$-$C_6$-alkyl or $C_1$-$C_6$-haloalkyl; and at least one of a and b represents a single bond and the other of a and b independently represents either a single bond or a double bond.

In certain embodiments, $R_1$ is hydrogen.

In certain embodiments, $R_1$ is —C(O)$R_3$. In certain embodiments, $R_3$ is $C_1$-$C_6$-alkyl, such as methyl; ethyl; propyl, such as n-propyl or isopropyl; or butyl, such as n-butyl, isobutyl, or tert-butyl. In certain embodiments, $R_3$ is substituted. Substituents of $R_3$ may include, but are not limited to aryl, heteroaryl, cycloalkyl, or heterocycloalkyl.

In certain embodiments, $A_1$ is a 6- to 10-membered aryl or a 5- to 10-membered heteroaryl. In certain embodiments, $A_1$ is phenyl, pyrazinyl, pyridinyl, pyrimidinyl, pyridazinyl, oxazolyl, thiazolyl, thienyl, furanyl, imidazolyl, pyrazolyl, triazolyl, benzoxazolyl, benzothienyl, benzimidazolyl, benzofuranyl, benzothiazolyl, indolyl, indenyl, naphthalenyl, quinolinyl, isoquinolinyl, quinoxalinyl, cinnolinyl, quinazolinyl, or phthalazinyl; each of which is optionally substituted. In certain embodiments, $A_1$ is

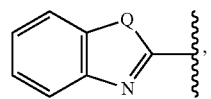

where Q is O, S, or N($R_C$). $R_C$ is selected from hydrogen; $C_1$-$C_6$-alkyl, or $C_1$-$C_6$-haloalkyl.

In certain embodiments, $A_1$ is unsubstituted. In certain embodiments, $A_1$ is substituted with one or more $R_4$. $R_4$ is independently selected at each occurrence from halogen, $C_1$-$C_6$-alkyl, and $C_1$-$C_6$-haloalkyl.

In certain embodiments, $A_1$ is substituted with one or more $R_4$. $R_4$ is independently selected at each occurrence from halogen, $C_1$-$C_6$-alkyl, and $C_1$-$C_6$-haloalkyl. In certain embodiments, $R_4$ is halogen. In certain embodiments, $R_4$ is fluoro. In certain embodiments, $R_4$ is chloro.

In certain embodiments, $A_1$ is a phenyl substituted with one or more $R_4$. In certain embodiments, $R_4$ is haloalkyl. In certain embodiments, $R_4$ is trifluoromethyl. In certain embodiments, $R_4$ is halogen. In certain embodiments, $R_4$ is fluoro. In certain embodiments, $R_4$ is chloro. In certain embodiments, $A_1$ is fluorophenyl. In certain embodiments, $A_1$ is chlorophenyl.

In certain embodiments, $A_1$ is a phenyl substituted with two or more $R_4$. In certain embodiments, each of the two or more $R_4$ is halogen. In certain embodiments, each of the two or more $R_4$ is fluoro. In certain embodiments, each of the two or more $R_4$ is chloro. In certain embodiments, $A_1$ is dihalophenyl. In certain embodiments, $A_1$ is difluorophenyl. In certain embodiments, $A_1$ is dichlorophenyl.

In certain embodiments, $A_1$ is a 7- to 10-membered aryl optionally substituted with one or more $R_4$. Each $R_4$ is independently selected from the group consisting of halogen, $C_1$-$C_6$-alkyl, and $C_1$-$C_6$-haloalkyl.

In certain embodiments, $A_1$ is a 5- to 10-membered heteroaryl optionally substituted with one or more $R_4$. Each $R_4$ is independently selected from the group consisting of halogen, $C_1$-$C_6$-alkyl, and $C_1$-$C_6$-haloalkyl.

In certain embodiments, $R_9$ is —C(O)$R_{10}$. In certain embodiments, $R_{10}$ is $C_1$-$C_6$-alkyl, such as methyl; ethyl; propyl, such as n-propyl or isopropyl; or butyl, such as n-butyl, isobutyl, or tert-butyl. In certain embodiments, $R_9$ is substituted. Substituents of $R_9$ may include, but are not limited to aryl, heteroaryl, cycloalkyl, or heterocycloalkyl.

In certain embodiments, both a and b are a single bond.

In one aspect, the present invention includes compounds of Formula (IV):

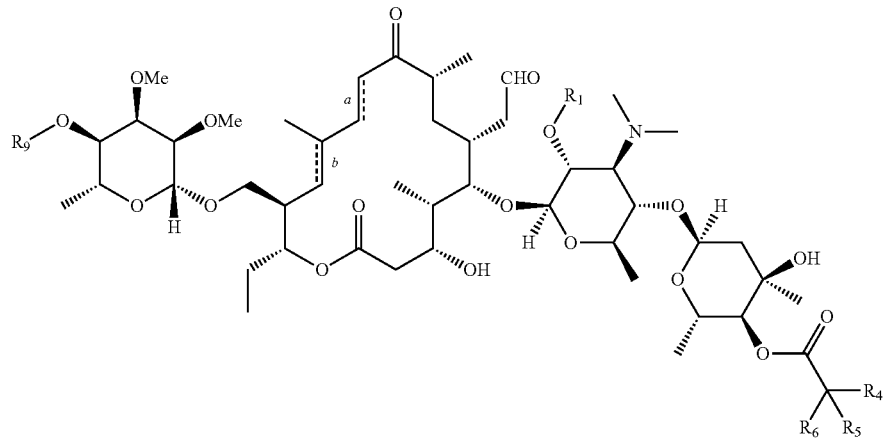

(IV)

and salts thereof, wherein:

$R_1$ represents hydrogen or —$C(O)R_3$, where $R_3$ represents an optionally substituted $C_1$-$C_6$-alkyl or $C_1$-$C_6$-haloalkyl;

each of $R_4$, $R_5$, and $R_6$ are independently selected from the group consisting of $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl;

$R_9$ represents hydrogen or —$C(O)R_{10}$, wherein $R_{10}$ represents an optionally substituted $C_1$-$C_6$-alkyl or $C_1$-$C_6$-haloalkyl; and each of a and b independently represents either a single bond or a double bond.

In certain embodiments, $R_1$ is hydrogen.

In certain embodiments, $R_1$ is —$C(O)R_3$. In certain embodiments, $R_3$ is $C_1$-$C_6$-alkyl, such as methyl; ethyl; propyl, such as n-propyl or isopropyl; or butyl, such as n-butyl, isobutyl, or tert-butyl. In certain embodiments, $R_3$ is substituted. Substituents of $R_3$ may include, but are not limited to aryl, heteroaryl, cycloalkyl, or heterocycloalkyl.

Each of $R_4$, $R_5$, and $R_6$ are independently selected from the group consisting of $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl. In certain embodiments, $R_4$ is $C_1$-$C_6$ alkyl. In certain embodiments, $R_4$ is methyl. In certain embodiments, $R_5$ is $C_1$-$C_6$ alkyl. In certain embodiments, $R_5$ is methyl. In certain embodiments, $R_6$ is $C_1$-$C_6$ alkyl. In certain embodiments, $R_6$ is methyl. In certain embodiments, each of $R_4$, $R_5$, and $R_6$ are $C_1$-$C_6$ alkyl.

In certain embodiments, $R_4$, $R_5$, and $R_6$ are the same. For example, in certain embodiments, each of $R_4$, $R_5$, and $R_6$ are methyl. In certain embodiments, at least two of $R_4$, $R_5$, and $R_6$ are the same. In certain embodiments, $R_4$, $R_5$, and $R_6$ are different.

In certain embodiments, $R_9$ is —$C(O)R_{10}$. In certain embodiments, $R_{10}$ is $C_1$-$C_6$-alkyl, such as methyl; ethyl; propyl, such as n-propyl or isopropyl; or butyl, such as n-butyl, isobutyl, or tert-butyl. In certain embodiments, $R_3$ is substituted. Substituents of $R_3$ may include, but are not limited to aryl, heteroaryl, cycloalkyl, or heterocycloalkyl.

In certain embodiments, both a and b are a double bond. In certain embodiments, at least one of a and b are a single bond. In certain embodiments, both a and b are a single bond.

In one aspect, the present invention includes compounds of Formula (V):

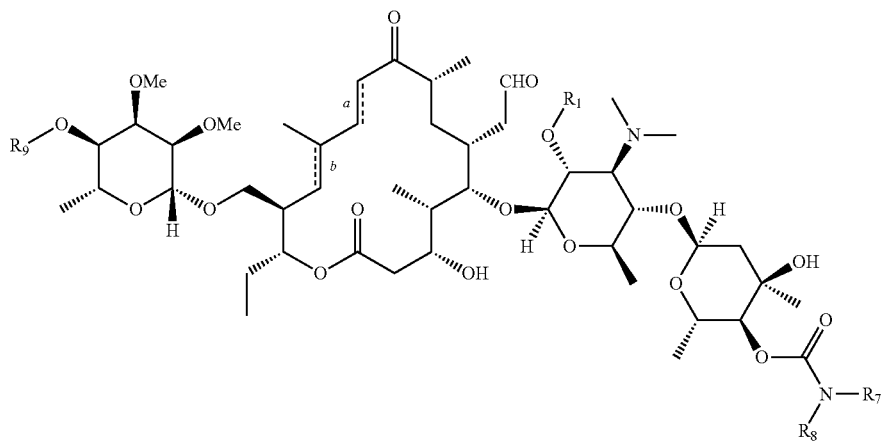

(V)

and salts thereof, wherein:

$R_1$ represents hydrogen or —$C(O)R_3$, where $R_3$ represents an optionally substituted $C_1$-$C_6$-alkyl or $C_1$-$C_6$-haloalkyl;

each of $R_7$ and $R_8$ are independently selected from the group consisting of $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl, or $R_7$ and $R_8$ together with the nitrogen atom to which they are attached form an optionally substituted saturated or partially saturated heterocyclic ring;

$R_9$ represents hydrogen or —C(O)$R_{10}$, wherein $R_{10}$ represents an optionally substituted $C_1$-$C_6$-alkyl or $C_1$-$C_6$-haloalkyl; and each of a and b independently represents either a single bond or a double bond.

In certain embodiments, $R_1$ is hydrogen.

In certain embodiments, $R_1$ is —C(O)$R_3$. In certain embodiments, $R_3$ is $C_1$-$C_6$-alkyl, such as methyl; ethyl; propyl, such as n-propyl or isopropyl; or butyl, such as n-butyl, isobutyl, or tert-butyl. In certain embodiments, $R_3$ is substituted. Substituents of $R_3$ may include, but are not limited to aryl, heteroaryl, cycloalkyl, or heterocycloalkyl.

In certain embodiments, $R_2$ is —C(O)N($R_7$)($R_8$). In certain embodiments, each of $R_7$ and $R_8$ are independently selected from the group consisting of $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl. In certain embodiments, $R_7$ and $R_8$ together with the nitrogen atom to which they are attached form an optionally substituted saturated or partially saturated heterocyclic ring. For instance $R_7$ and $R_8$, taken together with the atoms to which they are attached, can form, without limitation, an optionally substituted saturated heterocyclic ring such as

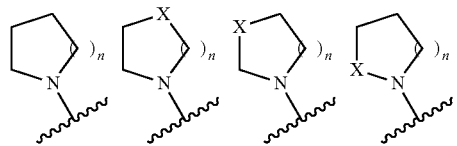

where X is O, S, or N($R_B$). $R_B$ is selected from hydrogen, $C_1$-$C_6$-alkyl, $C_2$-$C_6$-alkenyl, or $C_2$-$C_6$-alkynyl and n is 0, 1, 2, or 3.

In certain embodiments, $R_1$ is —C(O)$R_3$. In certain embodiments, $R_3$ is methyl. In certain embodiments, $R_3$ is propyl. In certain embodiments, $R_3$ is n-propyl. In certain embodiments, $R_3$ is isopropyl. In certain embodiments, $R_3$ is butyl. In certain embodiments, $R_3$ is n-butyl. In certain embodiments, $R_3$ is isobutyl. In certain embodiments, $R_3$ is tert-butyl.

In certain embodiments, one or both of $R_7$ or $R_8$ are $C_1$-$C_6$ alkyl. In certain embodiments, one or both of $R_7$ or $R_8$ are methyl. In certain embodiments, one or both of $R_7$ or $R_8$ are ethyl. In certain embodiments, one or both of $R_7$ or $R_8$ are propyl, such as n-propyl or isopropyl. In certain embodiments, one or both of $R_7$ or $R_8$ are butyl, such as n-butyl, isobutyl, or sec-butyl.

In certain embodiments, both of $R_7$ and $R_8$ are $C_1$-$C_6$ alkyl. In certain embodiments, both of $R_7$ and $R_8$ are methyl. In certain embodiments, both of $R_7$ and $R_8$ are ethyl. In certain embodiments, both of $R_7$ and $R_8$ are propyl, such as n-propyl or isopropyl. In certain embodiments, both of $R_7$ and $R_8$ are butyl, such as n-butyl, isobutyl, or sec-butyl. In certain embodiments, one of $R_7$ or $R_8$ is butyl and the other of $R_7$ or $R_8$ is ethyl.

In certain embodiments, one or both of $R_7$ or $R_8$ are $C_3$-$C_8$-cycloalkyl. In certain embodiments, both of $R_7$ and $R_8$ are $C_3$-$C_8$-cycloalkyl. In certain embodiments, both of $R_7$ and $R_8$ are cyclohexyl.

In certain embodiments, one or both of $R_7$ or $R_8$ are aryl. In certain embodiments, one or both of $R_7$ or $R_8$ are phenyl. In certain embodiments, one or both of $R_7$ or $R_8$ are unsubstituted phenyl.

In certain embodiments, one of $R_7$ or $R_8$ is $C_1$-$C_6$ alkyl and the other of $R_7$ or $R_8$ is aryl. In certain embodiments, one of $R_7$ or $R_8$ is phenyl and the other of $R_7$ or $R_8$ is methyl or ethyl. In certain embodiments, one of $R_7$ or $R_8$ is unsubstituted phenyl and the other of $R_7$ or $R_8$ is methyl.

In certain embodiments, $R_7$ and $R_8$ together with the nitrogen atom to which they are attached form an optionally substituted saturated or partially saturated heterocyclic ring. In certain embodiments, the heterocyclic ring is a non-aromatic ring. In certain embodiments, the heterocyclic ring is a pyrrolidine. In certain embodiments, the heterocyclic ring is a piperidine. In certain embodiments, the heterocyclic ring is a morpholine. In certain embodiments, the heterocyclic ring is an azepane.

In certain embodiments, $R_9$ is —C(O)$R_{10}$. In certain embodiments, $R_{10}$ is $C_1$-$C_6$-alkyl, such as methyl; ethyl; propyl, such as n-propyl or isopropyl; or butyl, such as n-butyl, isobutyl, or tert-butyl. In certain embodiments, $R_9$ is substituted. Substituents of $R_9$ may include, but are not limited to aryl, heteroaryl, cycloalkyl, or heterocycloalkyl.

In certain embodiments, both a and b are a double bond. In certain embodiments, at least one of a and b are a single bond. In certain embodiments, both a and b are a single bond.

In one aspect, the present invention includes compounds of Formula (VI):

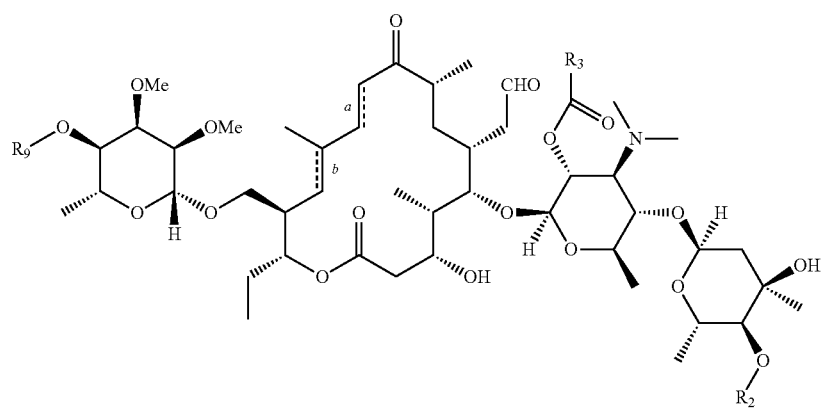

(VI)

and salts thereof, wherein:

$R_3$ represents an optionally substituted $C_1$-$C_6$-alkyl or $C_1$-$C_6$-haloalkyl;

$R_2$ represents —C(O)C($R_4$)($R_5$)($R_6$), wherein each of $R_4$, $R_5$, and $R_6$ are independently selected from the group consisting of $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl; or $R_2$ represents —C(O)N($R_7$)($R_8$), wherein each of $R_7$ and $R_8$ are independently selected from the group consisting of hydrogen, $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl, or $R_7$ and $R_8$ together with the nitrogen atom to which they are attached form an optionally substituted saturated or partially saturated heterocyclic ring; or $R_2$ represents —CH$_2$-$A_1$, wherein $A_1$ represents a 6- to 10-membered aryl or a 5- to 10-membered heteroaryl and $A_1$ is unsubstituted or substituted with one or more $R_4$, where each $R_4$ is independently selected from the group consisting of halogen, $C_1$-$C_6$-alkyl, and $C_1$-$C_6$-haloalkyl;

$R_9$ represents hydrogen or —C(O)$R_{10}$, wherein $R_{10}$ represents an optionally substituted $C_1$-$C_6$-alkyl or $C_1$-$C_6$-haloalkyl; and each of a and b independently represents either a single bond or a double bond.

In certain embodiments, $R_3$ is methyl. In certain embodiments, $R_3$ is ethyl. In certain embodiments, $R_3$ is propyl, such as isopropyl. In certain embodiments, $R_3$ is butyl, such as n-butyl.

In certain embodiments, $R_2$ is —C(O)C($R_4$)($R_5$)($R_6$). Each of $R_4$, $R_5$, and $R_6$ are independently selected from the group consisting of $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl. In certain embodiments, $R_4$ is $C_1$-$C_6$ alkyl. In certain embodiments, $R_5$ is $C_1$-$C_6$ alkyl. In certain embodiments, $R_6$ is $C_1$-$C_6$ alkyl. In certain embodiments, each of $R_4$, $R_5$, and $R_6$ are $C_1$-$C_6$ alkyl.

In certain embodiments, $R_2$ is —C(O)N($R_7$)($R_8$). In certain embodiments, each of $R_7$ and $R_8$ are independently selected from the group consisting of $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl. In certain embodiments, $R_7$ and $R_8$ together with the nitrogen atom to which they are attached form an optionally substituted saturated or partially saturated heterocyclic ring. For instance $R_7$ and $R_8$, taken together with the atoms to which they are attached, can form, without limitation, an optionally substituted saturated heterocyclic ring such as

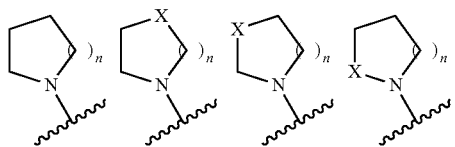

where X is O, S, or N($R_B$). $R_B$ is selected from hydrogen, $C_1$-$C_6$-alkyl, $C_2$-$C_6$-alkenyl, or $C_2$-$C_6$-alkynyl and n is 0, 1, 2, or 3.

In certain embodiments, $R_2$ is —CH$_2$-$A_1$. $A_1$ is a 6- to 10-membered aryl or a 5- to 10-membered heteroaryl. In certain embodiments, $A_1$ is phenyl, pyrazinyl, pyridinyl, pyrimidinyl, pyridazinyl, oxazolyl, thiazolyl, thienyl, furanyl, imidazolyl, pyrazolyl, triazolyl, benzoxazolyl, benzothienyl, benzimidazolyl, benzofuranyl, benzothiazolyl, indolyl, indenyl, naphthalenyl, quinolinyl, isoquinolinyl, quinoxalinyl, cinnolinyl, quinazolinyl, or phthalazinyl; each of which is optionally substituted. In certain embodiments, $A_1$ is

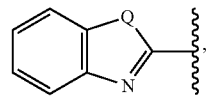

where Q is O, S, or N($R_C$). $R_C$ is selected from hydrogen; $C_1$-$C_6$-alkyl, or $C_1$-$C_6$-haloalkyl.

In certain embodiments, $A_1$ is unsubstituted. In certain embodiments, $A_1$ is substituted with one or more $R_4$. $R_4$ is independently selected at each occurrence from halogen, $C_1$-$C_6$-alkyl, and $C_1$-$C_6$-haloalkyl.

In certain embodiments, $R_2$ is —C(O)C($R_4$)($R_5$)($R_6$) and each of $R_4$, $R_5$, and $R_6$ are $C_1$-$C_6$ alkyl. In certain embodiments, $R_4$ is methyl. In certain embodiments, $R_5$ is methyl. In certain embodiments, $R_6$ is methyl. In certain embodiments, each of $R_4$, $R_5$, and $R_6$ are methyl.

In certain embodiments, $R_2$ is —C(O)N($R_7$)($R_8$) and one or both of $R_7$ or $R_8$ are $C_1$-$C_6$ alkyl. In certain embodiments, one or both of $R_7$ or $R_8$ are methyl. In certain embodiments, one or both of $R_7$ or $R_8$ are ethyl. In certain embodiments, one or both of $R_7$ or $R_8$ are propyl, such as n-propyl or isopropyl. In certain embodiments, one or both of $R_7$ or $R_8$ are butyl, such as n-butyl, isobutyl, or sec-butyl.

In certain embodiments, $R_2$ is —C(O)N($R_7$)($R_8$) and each of $R_7$ and $R_8$ are $C_1$-$C_6$ alkyl. In certain embodiments, both of $R_7$ and $R_8$ are methyl. In certain embodiments, both of $R_7$ and $R_8$ are ethyl. In certain embodiments, both of $R_7$ and $R_8$ are propyl, such as n-propyl or isopropyl. In certain embodiments, both of $R_7$ and $R_8$ are butyl, such as n-butyl, isobutyl, or sec-butyl. In certain embodiments, one of $R_7$ or $R_8$ is butyl and the other of $R_7$ or $R_8$ is ethyl.

In certain embodiments, $R_2$ is —C(O)N($R_7$)($R_8$) and one or both of $R_7$ or $R_8$ are $C_3$-$C_8$-cycloalkyl. In certain embodiments, both of $R_7$ and $R_8$ are $C_3$-$C_8$-cycloalkyl. In certain embodiments, both of $R_7$ and $R_8$ are cyclohexyl.

In certain embodiments, $R_2$ is —C(O)N($R_7$)($R_8$) and one or both of $R_7$ or $R_8$ are aryl. In certain embodiments, one or both of $R_7$ or $R_8$ are optionally substituted phenyl. In certain embodiments, one or both of $R_7$ or $R_8$ are unsubstituted phenyl.

In certain embodiments, $R_2$ is —C(O)N($R_7$)($R_8$) and one of $R_7$ or $R_8$ is $C_1$-$C_6$ alkyl and the other of $R_7$ or $R_8$ is aryl. In certain embodiments, one of $R_7$ or $R_8$ is optionally substituted phenyl and the other of $R_7$ or $R_8$ is methyl or ethyl. In certain embodiments, one of $R_7$ or $R_8$ is unsubstituted phenyl and the other of $R_7$ or $R_8$ is methyl.

In certain embodiments, $R_2$ is dialkyl carbamoyl. In certain embodiments, $R_2$ is dimethyl carbamoyl. In certain embodiments, $R_2$ is diethyl carbamoyl. In certain embodiments, $R_2$ is dipropyl carbamoyl. In certain embodiments, $R_2$ is di(propan-2-yl)carbamoyl. In certain embodiments, $R_2$ is dibutyl carbamoyl. In certain embodiments, $R_2$ is bis(2-methylpropyl)carbamoyl. In certain embodiments, $R_2$ is N-butyl-N-ethylcarbamoyl.

In certain embodiments, $R_2$ is N-methyl-N-phenylcarbamoyl.

In certain embodiments, $R_2$ is dicyclohexylcarbamoyl.

In certain embodiments, $R_2$ is —C(O)N($R_7$)($R_8$) and $R_7$ and $R_8$ together with the nitrogen atom to which they are attached form an optionally substituted saturated or partially saturated heterocyclic ring. In certain embodiments, the heterocyclic ring is a non-aromatic ring. In certain embodiments, the heterocyclic ring is a pyrrolidine. In certain embodiments, the heterocyclic ring is a piperidine. In certain embodiments, the heterocyclic ring is a morpholine. In certain embodiments, the heterocyclic ring is an azepane.

In certain embodiments, $R_2$ is —$CH_2$-$A_1$.

In certain embodiments, $A_1$ is an unsubstituted phenyl. In certain embodiments, $R_2$ is unsubstituted benzyl.

In certain embodiments, $A_1$ is a phenyl substituted with one or more $R_4$. In certain embodiments, $R_4$ is haloalkyl. In certain embodiments, $R_4$ is trifluoromethyl. In certain embodiments, $R_4$ is halogen. In certain embodiments, $R_4$ is fluoro. In certain embodiments, $R_4$ is chloro. In certain embodiments, $R_2$ is substituted benzyl. In certain embodiments, $R_2$ is trifluoromethylbenzyl. In certain embodiments, $R_2$ is trifluorobenzyl. In certain embodiments, $R_2$ is fluorobenzyl. In certain embodiments, $R_2$ is difluorobenzyl. In certain embodiments, $R_2$ is chlorobenzyl.

In certain embodiments, $A_1$ is naphthalene. In certain embodiments, $A_1$ is benzothiazole.

In certain embodiments, $R_9$ is —C(O)$R_{10}$. In certain embodiments, $R_{10}$ is $C_1$-$C_6$-alkyl, such as methyl; ethyl; propyl, such as n-propyl or isopropyl; or butyl, such as n-butyl, isobutyl, or tert-butyl. In certain embodiments, $R_9$ is substituted. Substituents of $R_9$ may include, but are not limited to aryl, heteroaryl, cycloalkyl, or heterocycloalkyl.

In certain embodiments, both a and b are a double bond. In certain embodiments, at least one of a and b are a single bond. In certain embodiments, both a and b are a single bond.

In certain embodiments, $R_3$ is $C_2$-$C_6$-alkyl; $R_2$ is —C(O)N($R_7$)($R_8$), wherein each of $R_7$ and $R_8$ are independently selected from the group consisting of hydrogen, $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl, or $R_7$ and $R_8$ together with the nitrogen atom to which they are attached form an optionally substituted saturated or partially saturated heterocyclic ring; $R_9$ is —C(O)$R_{10}$, wherein $R_{10}$ represents $C_1$-$C_6$-alkyl; and each of a and b independently represents either a single bond or a double bond.

In one aspect, the present invention includes compounds of Formula (VII):

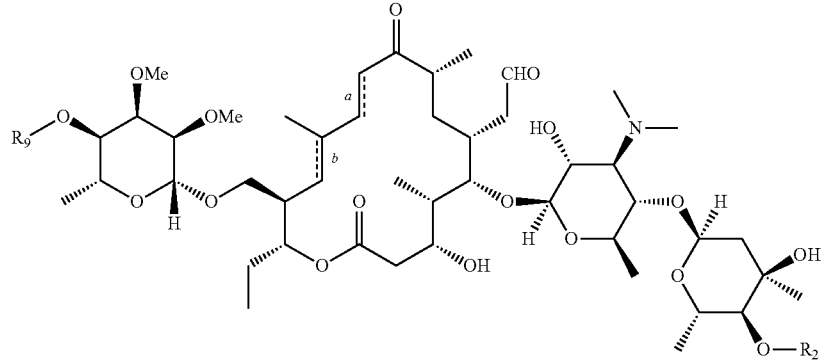

(VII)

and salts thereof, wherein:

$R_2$ represents —C(O)C($R_4$)($R_5$)($R_6$), wherein each of $R_4$, $R_5$, and $R_6$ are independently selected from the group consisting of $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl; or $R_2$ represents —C(O)N($R_7$)($R_8$), wherein each of $R_7$ and $R_8$ are independently selected from the group consisting of hydrogen, $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl, or $R_7$ and $R_8$ together with the nitrogen atom to which they are attached form an optionally substituted saturated or partially saturated heterocyclic ring; or $R_2$ represents —$CH_2$-$A_1$, wherein $A_1$ represents a phenyl substituted with one or more $R_4$, a 7- to 10-membered aryl optionally substituted with one or more $R_4$, or a 5- to 10-membered heteroaryl optionally substituted with one or more $R_4$, where each $R_4$ is independently selected from the group consisting of halogen, $C_1$-$C_6$-alkyl, and $C_1$-$C_6$-haloalkyl;

$R_9$ represents hydrogen or —C(O)$R_{10}$, wherein $R_{10}$ represents an optionally substituted $C_1$-$C_6$-alkyl or $C_1$-$C_6$-haloalkyl; and each of a and b independently represents either a single bond or a double bond.

In certain embodiments, $R_2$ is —C(O)C($R_4$)($R_5$)($R_6$). Each of $R_4$, $R_5$, and $R_6$ are independently selected from the group consisting of $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl. In certain embodiments, $R_4$ is $C_1$-$C_6$ alkyl. In certain embodiments, $R_5$ is $C_1$-$C_6$ alkyl. In certain embodiments, $R_6$ is $C_1$-$C_6$ alkyl. In certain embodiments, each of $R_4$, $R_5$, and $R_6$ are $C_1$-$C_6$ alkyl.

In certain embodiments, $R_2$ is —C(O)N($R_7$)($R_8$). In certain embodiments, each of $R_7$ and $R_8$ are independently selected from the group consisting of $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl. In certain embodiments, $R_7$ and $R_8$ together with the nitrogen atom to which they are attached form an optionally substituted saturated or partially saturated heterocyclic ring. For instance $R_7$ and $R_8$, taken together with the atoms to which they are attached, can form, without limitation, an optionally substituted saturated heterocyclic ring such as

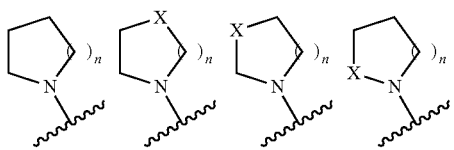

where X is O, S, or N(R$_B$). R$_B$ is selected from hydrogen, C$_1$-C$_6$-alkyl, C$_2$-C$_6$-alkenyl, or C$_2$-C$_6$-alkynyl and n is 0, 1, 2, or 3.

In certain embodiments, R$_2$ is —CH$_2$-A$_1$ and A$_1$ is a phenyl substituted with one or more R$_4$. In certain embodiments, A$_1$ is a halophenyl or a dihalophenyl.

In certain embodiments, R$_2$ is —CH$_2$-A$_1$ and A$_1$ is a 7- to 10-membered aryl optionally substituted with one or more R$_4$.

In certain embodiments, R$_2$ is —CH$_2$-A$_1$ and A$_1$ is a 5- to 10-membered heteroaryl optionally substituted with one or more R$_4$. Each R$_4$ is independently selected from the group consisting of halogen, C$_1$-C$_6$-alkyl, and C$_1$-C$_6$-haloalkyl.

In certain embodiments, R$_2$ is —CH$_2$-A$_1$ and A$_1$ is substituted phenyl or an optionally substituted pyrazinyl, pyridinyl, pyrimidinyl, pyridazinyl, oxazolyl, thiazolyl, thienyl, furanyl, imidazolyl, pyrazolyl, triazolyl, benzoxazolyl, benzothienyl, benzimidazolyl, benzofuranyl, benzothiazolyl, indolyl, indenyl, naphthalenyl, quinolinyl, isoquinolinyl, quinoxalinyl, cinnolinyl, quinazolinyl, or phthalazinyl; each of which is optionally substituted. In certain embodiments, A$_1$ is

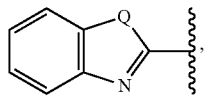

where Q is O, S, or N(R$_C$). R$_C$ is selected from hydrogen; C$_1$-C$_6$-alkyl, or C$_1$-C$_6$-haloalkyl.

In certain embodiments, A$_1$ is substituted with one or more R$_4$. R$_4$ is independently selected at each occurrence from halogen, C$_1$-C$_6$-alkyl, and C$_1$-C$_6$-haloalkyl. In certain embodiments, R$_4$ is halogen. In certain embodiments, R$_4$ is fluoro.

In certain embodiments, R$_2$ is —C(O)C(R$_4$)(R$_5$)(R$_6$) and each of R$_4$, R$_5$, and R$_6$ are C$_1$-C$_6$ alkyl. In certain embodiments, R$_4$ is methyl. In certain embodiments, R$_5$ is methyl. In certain embodiments, R$_6$ is methyl. In certain embodiments, each of R$_4$, R$_5$, and R$_6$ are methyl.

In certain embodiments, R$_2$ is —C(O)N(R$_7$)(R$_8$) and one or both of R$_7$ or R$_8$ are C$_1$-C$_6$ alkyl. In certain embodiments, one or both of R$_7$ or R$_8$ are methyl. In certain embodiments, one or both of R$_7$ or R$_8$ are ethyl. In certain embodiments, one or both of R$_7$ or R$_8$ are propyl, such as n-propyl or isopropyl. In certain embodiments, one or both of R$_7$ or R$_8$ are butyl, such as n-butyl, isobutyl, or sec-butyl.

In certain embodiments, R$_2$ is —C(O)N(R$_7$)(R$_8$) and each of R$_7$ and R$_8$ are C$_1$-C$_6$ alkyl. In certain embodiments, both of R$_7$ and R$_8$ are ethyl. In certain embodiments, both of R$_7$ and R$_8$ are propyl, such as n-propyl or isopropyl. In certain embodiments, both of R$_7$ and R$_8$ are butyl, such as n-butyl, isobutyl, or sec-butyl.

In certain embodiments, R$_2$ is —C(O)N(R$_7$)(R$_8$) and one or both of R$_7$ or R$_8$ are C$_3$-C$_8$-cycloalkyl. In certain embodiments, both of R$_7$ and R$_8$ are C$_3$-C$_8$-cycloalkyl. In certain embodiments, both of R$_7$ and R$_8$ are cyclohexyl.

In certain embodiments, R$_2$ is dialkyl carbamoyl. In certain embodiments, R$_2$ is diethyl carbamoyl. In certain embodiments, R$_2$ is dipropyl carbamoyl. In certain embodiments, R$_2$ is di(propan-2-yl)carbamoyl. In certain embodiments, R$_2$ is dibutyl carbamoyl.

In certain embodiments, R$_2$ is dicycloalkyl carbamoyl. In certain embodiments, R$_2$ is dicyclohexylcarbamoyl.

In certain embodiments, R$_2$ is —C(O)N(R$_7$)(R$_8$) and R$_7$ and R$_8$ together with the nitrogen atom to which they are attached form an optionally substituted saturated or partially saturated heterocyclic ring. In certain embodiments, the heterocyclic ring is a non-aromatic ring. In certain embodiments, the heterocyclic ring is a morpholine.

In certain embodiments, R$_2$ is —CH$_2$-A$_1$.

In certain embodiments, R$_2$ is —CH$_2$-A$_1$ and A$_1$ is a phenyl substituted with one or more R$_4$. In certain embodiments, R$_4$ is halogen. In certain embodiments, R$_4$ is fluoro. In certain embodiments, R$_2$ is substituted benzyl. In certain embodiments, R$_2$ is fluorobenzyl. In certain embodiments, R$_2$ is difluorobenzyl.

In certain embodiments, R$_9$ is —C(O)R$_{10}$. In certain embodiments, R$_{10}$ is C$_1$-C$_6$-alkyl, such as methyl; ethyl; propyl, such as n-propyl or isopropyl; or butyl, such as n-butyl, isobutyl, or tert-butyl. In certain embodiments, R$_9$ is substituted. Substituents of R$_9$ may include, but are not limited to aryl, heteroaryl, cycloalkyl, or heterocycloalkyl.

In certain embodiments, both a and b are a double bond. In certain embodiments, at least one of a and b are a single bond. In certain embodiments, both a and b are a single bond.

In certain embodiments, R$_2$ is —C(O)N(R$_7$)(R$_8$), wherein each of R$_7$ and R$_8$ are independently selected from the group consisting of hydrogen, C$_1$-C$_6$-alkyl, C$_1$-C$_6$-haloalkyl, aryl, heteroaryl, C$_3$-C$_8$-cycloalkyl, heterocycloalkyl, arylalkyl, heteroarylalkyl, and C$_3$-C$_8$-cycloalkyl-C$_1$-C$_4$-alkyl, or R$_7$ and R$_8$ together with the nitrogen atom to which they are attached form an optionally substituted saturated or partially saturated heterocyclic ring; and R$_9$ is —C(O)R$_{10}$, wherein R$_{10}$ represents C$_1$-C$_6$-alkyl; and each of a and b independently represents either a single bond or a double bond.

In one aspect, the present invention includes compounds of Formula (VIII):

(VIII)

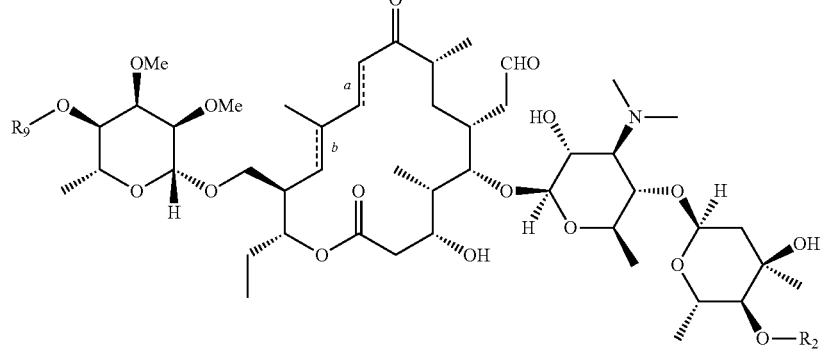

and salts thereof, wherein:

$R_2$ represents —C(O)C($R_4$)($R_5$)($R_6$), wherein each of $R_4$, $R_5$, and $R_6$ are independently selected from the group consisting of $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl; or $R_2$ represents —C(O)N($R_7$)($R_8$), wherein each of $R_7$ and $R_8$ are independently selected from the group consisting of hydrogen, $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl, or $R_7$ and $R_8$ together with the nitrogen atom to which they are attached form an optionally substituted saturated or partially saturated heterocyclic ring; or $R_2$ represents —$CH_2$-$A_1$, wherein $A_1$ represents a 6- to 10-membered aryl or a 5- to 10-membered heteroaryl and $A_1$ is unsubstituted or substituted with one or more $R_A$, wherein each $R_A$ is independently selected from the group consisting of halogen, $C_1$-$C_6$-alkyl, and $C_1$-$C_6$-haloalkyl;

$R_9$ represents hydrogen or —C(O)$R_{10}$, wherein $R_{10}$ represents an optionally substituted $C_1$-$C_6$-alkyl or $C_1$-$C_6$-haloalkyl; and at least one of a and b represents a single bond and the other of a and b independently represents either a single bond or a double bond.

In certain embodiments, $R_2$ is —C(O)C($R_4$)($R_5$)($R_6$). Each of $R_4$, $R_5$, and $R_6$ are independently selected from the group consisting of $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl. In certain embodiments, $R_4$ is $C_1$-$C_6$ alkyl. In certain embodiments, $R_5$ is $C_1$-$C_6$ alkyl. In certain embodiments, $R_6$ is $C_1$-$C_6$ alkyl. In certain embodiments, each of $R_4$, $R_5$, and $R_6$ are $C_1$-$C_6$ alkyl.

In certain embodiments, $R_2$ is —C(O)N($R_7$)($R_8$). In certain embodiments, each of $R_7$ and $R_8$ are independently selected from the group consisting of $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl. In certain embodiments, $R_7$ and $R_8$ together with the nitrogen atom to which they are attached form an optionally substituted saturated or partially saturated heterocyclic ring. For instance $R_7$ and $R_8$, taken together with the atoms to which they are attached, can form, without limitation, an optionally substituted saturated heterocyclic ring such as

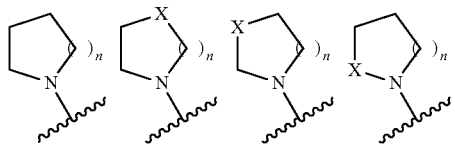

where X is O, S, or N($R_B$). $R_B$ is selected from hydrogen, $C_1$-$C_6$-alkyl, $C_2$-$C_6$-alkenyl, or $C_2$-$C_6$-alkynyl and n is 0, 1, 2, or 3.

In certain embodiments, $R_2$ is —$CH_2$-$A_1$ and $A_1$ is a 6- to 10-membered aryl or a 5- to 10-membered heteroaryl. In certain embodiments, $A_1$ is phenyl, pyrazinyl, pyridinyl, pyrimidinyl, pyridazinyl, oxazolyl, thiazolyl, thienyl, furanyl, imidazolyl, pyrazolyl, triazolyl, benzoxazolyl, benzothienyl, benzimidazolyl, benzofuranyl, benzothiazolyl, indolyl, indenyl, naphthalenyl, quinolinyl, isoquinolinyl, quinoxalinyl, cinnolinyl, quinazolinyl, or phthalazinyl; each of which is optionally substituted. In certain embodiments, $A_1$ is

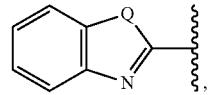

where Q is O, S, or N($R_C$). $R_C$ is selected from hydrogen; $C_1$-$C_6$-alkyl, or $C_1$-$C_6$-haloalkyl.

In certain embodiments, $A_1$ is unsubstituted. In certain embodiments, $A_1$ is substituted with one or more $R_A$. $R_A$ is independently selected at each occurrence from halogen, $C_1$-$C_6$-alkyl, and $C_1$-$C_6$-haloalkyl. In certain embodiments, $R_A$ is halogen. In certain embodiments, $R_A$ is fluoro.

In certain embodiments, $A_1$ is a phenyl substituted with one or more $R_A$. In certain embodiments, $A_1$ is a halophenyl or a dihalophenyl.

In certain embodiments, $R_2$ is —$CH_2$-$A_1$ and $A_1$ is a 7- to 10-membered aryl optionally substituted with one or more $R_A$. Each $R_A$ is independently selected from the group consisting of halogen, $C_1$-$C_6$-alkyl, and $C_1$-$C_6$-haloalkyl.

In certain embodiments, $R_2$ is —$CH_2$-$A_1$ and $A_1$ is a 5- to 10-membered heteroaryl optionally substituted with one or more $R_A$. Each $R_A$ is independently selected from the group consisting of halogen, $C_1$-$C_6$-alkyl, and $C_1$-$C_6$-haloalkyl.

In certain embodiments, $R_2$ is —C(O)C($R_4$)($R_5$)($R_6$) and each of $R_4$, $R_5$, and $R_6$ are $C_1$-$C_6$ alkyl. In certain embodiments, $R_4$ is methyl. In certain embodiments, $R_5$ is methyl. In certain embodiments, $R_6$ is methyl. In certain embodiments, each of $R_4$, $R_5$, and $R_6$ are methyl.

In certain embodiments, $R_2$ is —C(O)N($R_7$)($R_8$) and one or both of $R_7$ or $R_8$ are $C_1$-$C_6$ alkyl. In certain embodiments, one or both of $R_7$ or $R_8$ are methyl. In certain embodiments, one or both of $R_7$ or $R_8$ are ethyl. In certain embodiments, one or both of $R_7$ or $R_8$ are propyl, such as n-propyl or isopropyl. In certain embodiments, one or both of $R_7$ or $R_8$ are butyl, such as n-butyl, isobutyl, or sec-butyl.

In certain embodiments, $R_2$ is —C(O)N($R_7$)($R_8$) and each of $R_7$ and $R_8$ are $C_1$-$C_6$ alkyl. In certain embodiments, both of $R_7$ and $R_8$ are ethyl. In certain embodiments, both of $R_7$ and $R_8$ are propyl, such as n-propyl or isopropyl. In certain embodiments, both of $R_7$ and $R_8$ are butyl, such as n-butyl, isobutyl, or sec-butyl.

In certain embodiments, $R_2$ is —C(O)N($R_7$)($R_8$) and one or both of $R_7$ or $R_8$ are $C_3$-$C_8$-cycloalkyl. In certain embodiments, both of $R_7$ and $R_8$ are $C_3$-$C_8$-cycloalkyl. In certain embodiments, both of $R_7$ and $R_8$ are cyclohexyl.

In certain embodiments, $R_2$ is dialkyl carbamoyl. In certain embodiments, $R_2$ is diethyl carbamoyl. In certain embodiments, $R_2$ is dipropyl carbamoyl. In certain embodiments, $R_2$ is di(propan-2-yl)carbamoyl. In certain embodiments, $R_2$ is dibutyl carbamoyl.

In certain embodiments, $R_2$ is dicycloalkyl carbamoyl. In certain embodiments, $R_2$ is dicyclohexylcarbamoyl.

In certain embodiments, $R_2$ is —C(O)N($R_7$)($R_8$) and $R_7$ and $R_8$ together with the nitrogen atom to which they are attached form an optionally substituted saturated or partially saturated heterocyclic ring. In certain embodiments, the heterocyclic ring is a non-aromatic ring. In certain embodiments, the heterocyclic ring is a morpholine.

In certain embodiments, $R_2$ is substituted benzyl. In certain embodiments, $R_2$ is fluorobenzyl. In certain embodiments, $R_2$ is difluorobenzyl.

In certain embodiments, $R_9$ is —C(O)$R_{10}$. In certain embodiments, $R_{10}$ is $C_1$-$C_6$-alkyl, such as methyl; ethyl; propyl, such as n-propyl or isopropyl; or butyl, such as n-butyl, isobutyl, or tert-butyl. In certain embodiments, $R_9$ is substituted. Substituents of $R_9$ may include, but are not limited to aryl, heteroaryl, cycloalkyl, or heterocycloalkyl.

In certain embodiments, both a and b are a single bond.

In certain embodiments, $R_2$ is —C(O)N($R_7$)($R_8$), wherein each of $R_7$ and $R_8$ are independently selected from the group consisting of hydrogen, $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl, or $R_7$ and $R_8$ together with the nitrogen atom to which they are attached form an optionally substituted saturated or partially saturated heterocyclic ring; and $R_9$ is —C(O)$R_{10}$, wherein $R_{10}$ represents $C_1$-$C_6$-alkyl; and at least one of a and b represents a single bond and the other of a and b independently represents either a single bond or a double bond.

In one aspect, the present invention includes compounds of Formula (IX):

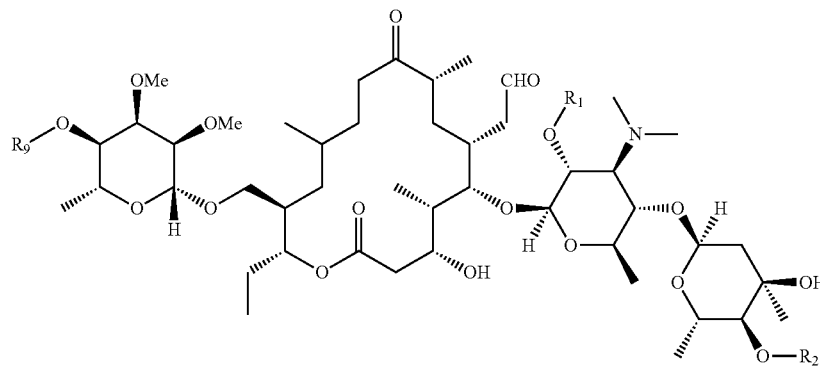

(IX)

and salts thereof, wherein:

$R_1$ represents hydrogen or —C(O)$R_3$, wherein $R_3$ represents an optionally substituted $C_1$-$C_6$-alkyl or $C_1$-$C_6$-haloalkyl;

$R_2$ represents —C(O)C($R_4$)($R_5$)($R_6$), wherein each of $R_4$, $R_5$, and $R_6$ are independently selected from the group consisting of $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl; or $R_2$ represents —C(O)N($R_7$)($R_8$), wherein each of $R_7$ and $R_8$ are independently selected from the group consisting of $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl, or $R_7$ and $R_8$ together with the nitrogen atom to which they are attached form an optionally substituted saturated or partially saturated heterocyclic ring; or $R_2$ represents —CH$_2$-$A_1$, wherein $A_1$ represents a 6- to 10-membered aryl or a 5- to 10-membered heteroaryl and $A_1$ is unsubstituted or substituted with one or more $R_4$, wherein each $R_4$ is independently selected from the group consisting of halogen, $C_1$-$C_6$-alkyl, and $C_1$-$C_6$-haloalkyl;

$R_9$ represents hydrogen or —C(O)$R_{10}$, wherein $R_{10}$ represents an optionally substituted $C_1$-$C_6$-alkyl or $C_1$-$C_6$-haloalkyl.

In certain embodiments, $R_1$ is hydrogen.

In certain embodiments, $R_1$ is —C(O)$R_3$. In certain embodiments, $R_3$ is $C_1$-$C_6$-alkyl, such as methyl; ethyl; propyl, such as n-propyl or isopropyl; or butyl, such as n-butyl, isobutyl, or tert-butyl. In certain embodiments, $R_3$ is substituted. Substituents of $R_3$ may include, but are not limited to aryl, heteroaryl, cycloalkyl, or heterocycloalkyl.

In certain embodiments, $R_2$ is —C(O)C($R_4$)($R_5$)($R_6$). Each of $R_4$, $R_5$, and $R_6$ are independently selected from the group consisting of $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl. In certain embodiments, $R_4$ is $C_1$-$C_6$ alkyl. In certain embodiments, $R_5$ is $C_1$-$C_6$ alkyl. In certain embodiments, $R_6$ is $C_1$-$C_6$ alkyl. In certain embodiments, each of $R_4$, $R_5$, and $R_6$ are $C_1$-$C_6$ alkyl.

In certain embodiments, $R_4$, $R_5$, and $R_6$ are the same. For example, in certain embodiments, each of $R_4$, $R_5$, and $R_6$ are methyl. In certain embodiments, at least two of $R_4$, $R_5$, and $R_6$ are the same. In certain embodiments, $R_4$, $R_5$, and $R_6$ are different.

In certain embodiments, $R_2$ is —C(O)N($R_7$)($R_8$). In certain embodiments, each of $R_7$ and $R_8$ are independently selected from the group consisting of $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl. In certain embodiments, $R_7$ and $R_8$ together with the nitrogen atom to which they are attached form an optionally substituted saturated or partially saturated heterocyclic ring. For instance $R_7$ and $R_8$, taken together with the atoms to which they are attached, can form, without limitation, an optionally substituted saturated heterocyclic ring such as

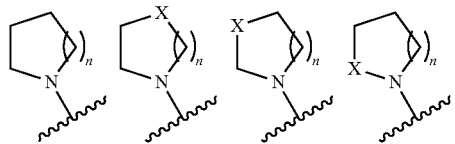

where X is O, S, or N($R_B$). $R_B$ is selected from hydrogen, $C_1$-$C_6$-alkyl, $C_2$-$C_6$-alkenyl, or $C_2$-$C_6$-alkynyl and n is 0, 1, 2, or 3.

In certain embodiments, $R_2$ is —CH$_2$-$A_1$ and $A_1$ is a 6- to 10-membered aryl or a 5- to 10-membered heteroaryl. In certain embodiments, $A_1$ is phenyl, pyrazinyl, pyridinyl, pyrimidinyl, pyridazinyl, oxazolyl, thiazolyl, thienyl, furanyl, imidazolyl, pyrazolyl, triazolyl, benzoxazolyl, benzothienyl, benzimidazolyl, benzofuranyl, benzothiazolyl, indolyl, indenyl, naphthalenyl, quinolinyl, isoquinolinyl, quinoxalinyl, cinnolinyl, quinazolinyl, or phthalazinyl; each of which is optionally substituted. In certain embodiments, $A_1$ is

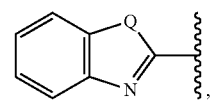

where Q is O, S, or N($R_C$). $R_C$ is selected from hydrogen; $C_1$-$C_6$-alkyl, or $C_1$-$C_6$-haloalkyl.

In certain embodiments, $A_1$ is unsubstituted. In certain embodiments, $A_1$ is substituted with one or more $R_4$. In certain embodiments, $R_4$ is halogen, $C_1$-$C_6$-alkyl, or $C_1$-$C_6$-haloalkyl.

In certain embodiments, $R_1$ is —C(O)$R_3$ and $R_3$ is $C_1$-$C_6$-alkyl. In certain embodiments, $R_3$ is methyl. In certain embodiments, $R_3$ is propyl. In certain embodiments, $R_3$ is n-propyl. In certain embodiments, $R_3$ is isopropyl. In certain embodiments, $R_3$ is butyl. In certain embodiments, $R_3$ is n-butyl. In certain embodiments, $R_3$ is isobutyl. In certain embodiments, $R_3$ is tert-butyl.

In certain embodiments, $R_2$ is —C(O)N($R_7$)($R_8$) and one or both of $R_7$ or $R_8$ are $C_1$-$C_6$ alkyl. In certain embodiments, one or both of $R_7$ or $R_8$ are methyl. In certain embodiments, one or both of $R_7$ or $R_8$ are ethyl. In certain embodiments, one or both of $R_7$ or $R_8$ are propyl, such as n-propyl or isopropyl. In certain embodiments, one or both of $R_7$ or $R_8$ are butyl, such as n-butyl, isobutyl, or sec-butyl.

In certain embodiments, $R_2$ is —C(O)N($R_7$)($R_8$) and each of $R_7$ and $R_8$ are $C_1$-$C_6$ alkyl. In certain embodiments, both of $R_7$ and $R_8$ are methyl. In certain embodiments, both of $R_7$ and $R_8$ are ethyl. In certain embodiments, both of $R_7$ and $R_8$ are propyl, such as n-propyl or isopropyl. In certain embodiments, both of $R_7$ and $R_8$ are butyl, such as n-butyl, isobutyl, or sec-butyl. In certain embodiments, one of $R_7$ or $R_8$ is butyl and the other of $R_7$ or $R_8$ is ethyl.

In certain embodiments, $R_2$ is dialkyl carbamoyl. In certain embodiments, $R_2$ is dimethyl carbamoyl. In certain embodiments, $R_2$ is diethyl carbamoyl. In certain embodiments, $R_2$ is dipropyl carbamoyl. In certain embodiments, $R_2$ is di(propan-2-yl)carbamoyl. In certain embodiments, $R_2$ is dibutyl carbamoyl. In certain embodiments, $R_2$ is bis(2-methylpropyl)carbamoyl. In certain embodiments, $R_2$ is N-butyl-N-ethylcarbamoyl.

In certain embodiments, $R_2$ is —CH$_2$-$A_1$.

In certain embodiments, $A_1$ is a phenyl substituted with one or more $R_4$. In certain embodiments, $R_4$ is haloalkyl. In certain embodiments, $R_4$ is halogen. In certain embodiments, $R_4$ is fluoro.

In certain embodiments, $R_2$ is substituted benzyl. In certain embodiments, $R_2$ is trifluoromethylbenzyl. In certain embodiments, $R_2$ is fluorobenzyl. In certain embodiments, $R_2$ is difluorobenzyl.

In certain embodiments, $R_9$ is —C(O)$R_{10}$. In certain embodiments, $R_{10}$ is $C_1$-$C_6$-alkyl, such as methyl; ethyl; propyl, such as n-propyl or isopropyl; or butyl, such as n-butyl, isobutyl, or tert-butyl. In certain embodiments, $R_9$ is substituted. Substituents of $R_9$ may include, but are not limited to aryl, heteroaryl, cycloalkyl, or heterocycloalkyl.

Without limiting the foregoing, particular combinations of substitutions are further described below.

In certain embodiments, $R_1$ is hydrogen, $R_2$ is —C(O)N(CH$_2$CH$_3$)$_2$, and $R_9$ is hydrogen.

In certain embodiments, $R_1$ is —C(O)CH(CH$_3$)$_2$, $R_2$ is —C(O)N(CH$_2$CH$_3$)$_2$, and $R_9$ is hydrogen.

In certain embodiments, $R_1$ is hydrogen, $R_2$ is fluorobenzyl, and $R_9$ is hydrogen.

In certain embodiments, $R_1$ is hydrogen, $R_2$ is

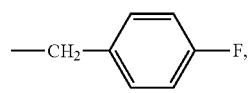

and $R_9$ is hydrogen.

In certain embodiments, $R_1$ is hydrogen, $R_2$ is difluorobenzyl, and $R_9$ is hydrogen.

In certain embodiments, $R_1$ is hydrogen, $R_2$ is

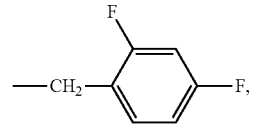

and $R_9$ is hydrogen.

In certain embodiments, $R_1$ is hydrogen, $R_2$ is —C(O)N(CH$_2$CH$_3$)$_2$, and $R_9$ is —C(O)$R_{10}$, wherein $R_{10}$ represents $C_1$-$C_6$-alkyl.

In certain embodiments, $R_1$ is —C(O)CH(CH$_3$)$_2$, $R_2$ is —C(O)N(CH$_2$CH$_3$)$_2$, and $R_9$ is —C(O)$R_{10}$, wherein $R_{10}$ represents $C_1$-$C_6$-alkyl.

In certain embodiments, $R_1$ is hydrogen, $R_2$ is fluorobenzyl, and $R_9$ is —C(O)$R_{10}$, wherein $R_{10}$ represents $C_1$-$C_6$-alkyl.

In certain embodiments, $R_1$ is hydrogen, $R_2$ is

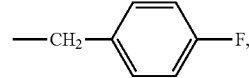

and $R_9$ is —C(O)$R_{10}$, wherein $R_{10}$ represents $C_1$-$C_6$-alkyl.

In certain embodiments, $R_1$ is hydrogen, $R_2$ is difluorobenzyl, and $R_9$ is —C(O)$R_{10}$, wherein $R_{10}$ represents $C_1$-$C_6$-alkyl.

In certain embodiments, $R_1$ is hydrogen, $R_2$ is

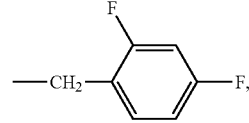

and $R_9$ is —C(O)$R_{10}$, wherein $R_{10}$ represents $C_1$-$C_6$-alkyl.

In certain embodiments, $R_1$ is —C(O)$R_3$, wherein $R_3$ represents $C_1$-$C_6$-alkyl; $R_2$ is —C(O)N($R_7$)($R_8$), wherein each of $R_7$ and $R_8$ are independently selected from the group consisting of hydrogen, $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl, or $R_7$ and $R_8$ together with the nitrogen atom to which they are attached form an optionally substituted saturated or partially saturated heterocyclic ring; and $R_9$ is hydrogen.

In certain embodiments, $R_1$ is hydrogen; $R_2$ is —C(O)N($R_7$)($R_8$), wherein each of $R_7$ and $R_8$ are independently selected from the group consisting of hydrogen, $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl, or $R_7$ and $R_8$ together with the nitrogen atom to which they are attached form an optionally substituted saturated or partially saturated heterocyclic ring; and $R_9$ is —C(O)$R_{10}$, wherein $R_{10}$ represents $C_1$-$C_6$-alkyl.

In one aspect, the present compounds include 4″-substituted tylosin A analogs and derivatives. In certain embodiments, the present compounds include 2′-substituted and 4″-substituted tylosin A analogs and derivatives. In certain embodiments, such analogs retain antibiotic activity, but demonstrate improved absorption and longer in vivo half-lives. Thus, in certain embodiments, the resultant compounds have pharmacokinetic properties consistent with oral dosing, while retaining potent antibiotic activity against gram-positive and some gram-negative organisms.

In certain embodiments, the present compounds include tylosin A analogs and derivatives having a 4"-O-halobenzyl or 4"-O-dihalobenzyl moiety. In certain embodiments, the present compounds include tylosin A analogs and derivatives having a 4"-O-dimethylpropionyl moiety. In certain embodiments, the present compounds include tylosin A analogs and derivatives having a 4"-O-dialkylcarbamoyl, 4"-O-dicycloalkylcarbamoyl, or 4"-morpholine-4-carboxylate moiety.

As noted by Takeuchi et al. (J. Antibiotics 1987, 1358), esters of the 4"-OH group tend to be highly unstable in vivo, a result of hydrolysis due to the action of putative hepatic esterases. This metabolic event creates a challenge for achieving useful circulating levels of active drug.

In one aspect, the present compounds include tylosin A analogs and derivatives having a stable 4"-ester moiety. In certain embodiments, the stable 4"-ester moiety includes three non-hydrogen substituents at the alpha-position of the ester. In other embodiments, the stable 4"-ester moiety includes a nitrogen atom having two non-hydrogen substituents. For example, in certain embodiments, the nitrogen atom is disubstituted to form a disubstituted carbamate.

In certain embodiments, the present compounds include tylosin A analogs and derivatives having a carbamate at the 4" position. In certain embodiments, the 4"-carbamate lacks a hydrogen bond donor. In certain embodiments, the nitrogen atom of the carbamate has two non-hydrogen substituents.

In certain embodiments, the present compounds include tylosin A analogs and derivatives having a disubstituted carbamate at the 4" position. In certain embodiments, a disubstituted carbamoyl chloride, such as a dialkylcarbamoyl chloride, is used to produce a compound having a disubstituted carbamate at the 4" position; the success of such a reaction scheme was not predictable prior to the present disclosure. Appropriate methods and reagents for preparing a tylosin A analog or derivative having a disubstituted carbamate at the 4" position are identified throughout the present disclosure.

In one aspect, the present compounds include 2'-substituted tylosin A analogs and derivatives. In certain embodiments, the present compounds include tylosin A analogs and derivatives having a 2'-O-acyl moiety. In certain embodiments, the present compounds include tylosin A analogs and derivatives having a 2'-O-acetyl moiety. In certain embodiments, the present compounds include tylosin A analogs and derivatives having a 2'-O-propionyl moiety. In certain embodiments, the present compounds include tylosin A analogs and derivatives having a 2'-O-methylpropionyl moiety.

It is to be understood that compounds disclosed herein may exhibit the stereoisomerism, including geometric isomerism, and/or tautomerism.

For example, the present compounds may exist as stereoisomers where asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30.

The present disclosure contemplates various stereoisomers and mixtures thereof and these are specifically included within the scope of the invention. Stereoisomers include enantiomers and diastereomers, and mixtures of enantiomers or diastereomers. Individual stereoisomers of the present compounds may be prepared synthetically from commercially available starting materials which contain asymmetric or chiral centers or by preparation of racemic mixtures followed by resolution.

The present disclosure also contemplates various geometric isomers and mixtures thereof resulting from the disposition of substituents around a carbon-carbon double bond, a carbon-nitrogen double bond, a cycloalkyl group, or a heterocycle group.

The present disclosure also contemplates various tautomers and mixtures thereof resulting from, for example, interconversion between keto and enol forms.

Thus, the formulae drawings within this specification can represent only one of the possible tautomeric or stereoisomeric forms. It is to be understood that the invention encompasses any tautomeric or stereoisomeric form, and mixtures thereof, and is not to be limited merely to any one tautomeric or stereoisomeric form utilized within the naming of the compounds or formulae drawings.

The present disclosure also contemplates isotopically-labeled compounds, which are identical to those recited in Formula (I), Formula (II), Formula (III), Formula (IV), Formula (V), Formula (VI), Formula (VII), Formula (VIII), or Formula (IX) but for the fact that one or more atoms are replaced by an atom having an atomic mass or mass number different from the atomic mass or mass number usually found in nature. Examples of isotopes suitable for inclusion in such isotopically-labeled compounds are hydrogen, carbon, nitrogen, oxygen, phosphorus, fluorine, and chlorine, such as, but not limited to $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Compounds incorporating positron-emitting isotopes are useful in medical imaging and positron-emitting tomography (PET) studies for determining the distribution of receptors. Suitable positron-emitting isotopes that can be incorporated in compounds of Formula (I), Formula (II), Formula (III), Formula (IV), Formula (V), Formula (VI), Formula (VII), Formula (VIII), or Formula (IX) are $^{11}C$, $^{13}N$, $^{15}O$, and $^{18}F$. Isotopically-labeled compounds of Formula (I), Formula (II), Formula (III), Formula (IV), Formula (V), Formula (VI), Formula (VII), Formula (VIII), or Formula (IX) can generally be prepared by conventional techniques known to those skilled in the art or by processes analogous to those described in the accompanying Schemes and Examples using appropriate isotopically-labeled reagent in place of non-isotopically-labeled reagent.

C. Methods for Preparing Compounds

The present compounds can be better understood in connection with the following synthetic schemes and methods which illustrate a means by which the compounds can be prepared.

The present compounds may be prepared from Tylosin A as described below.

As indicated in Scheme 1, Tylosin A (or a salt thereof) is selectively acylated at the 2'-hydroxyl using an acylating agent such as an acid anhydride or the like, in a solvent such as acetone or chloroform or ethanol or the like. Alternatively, the acylating agent may be generated in situ, using a carboxylic acid and an activating agent such as isobutyl chloformate or the like, optionally in the presence of a base such as N-methylmorpholine or the like.

SCHEME 1

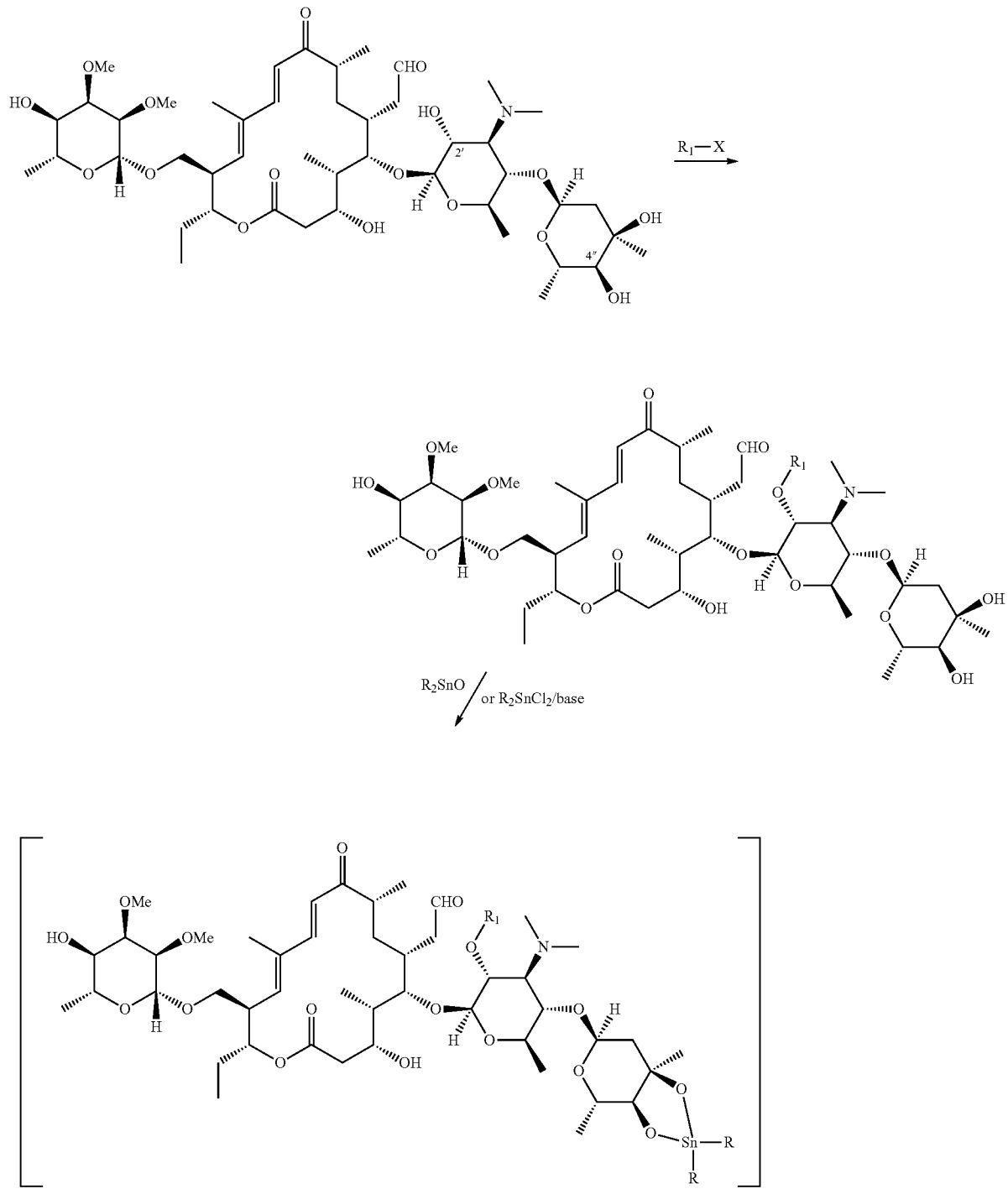

The resultant 2'-ester may be converted to the corresponding 3"/4"-cyclic tin reagent through reaction with dibutyltin oxide, or dibutyltin dichloride, or the like, optionally in the presence of a base such as 1,2,2,6,6,-pentamethylpiperidine or the like, in a solvent such as toluene or THF or the like. As indicated in Scheme 2, the resultant tin reagent is not generally isolated, but is reacted directly a) with an acylating agent, such as an acid chloride or the like, to give the corresponding 4"-acylated analog;

b) with a carbamylating agent, such diethylcarbamyl chloride or ethyl isocyanate or the like, to give the corresponding 4"-carbamate analog; or c) with a benzylating agent, for example 4-fluorobenzyl brominde or the like, optionally in the presence of an iodide source such as tetra-n-butylammonium iodide or the like, to give the corresponding 4"-benzylated analog.

SCHEME 2
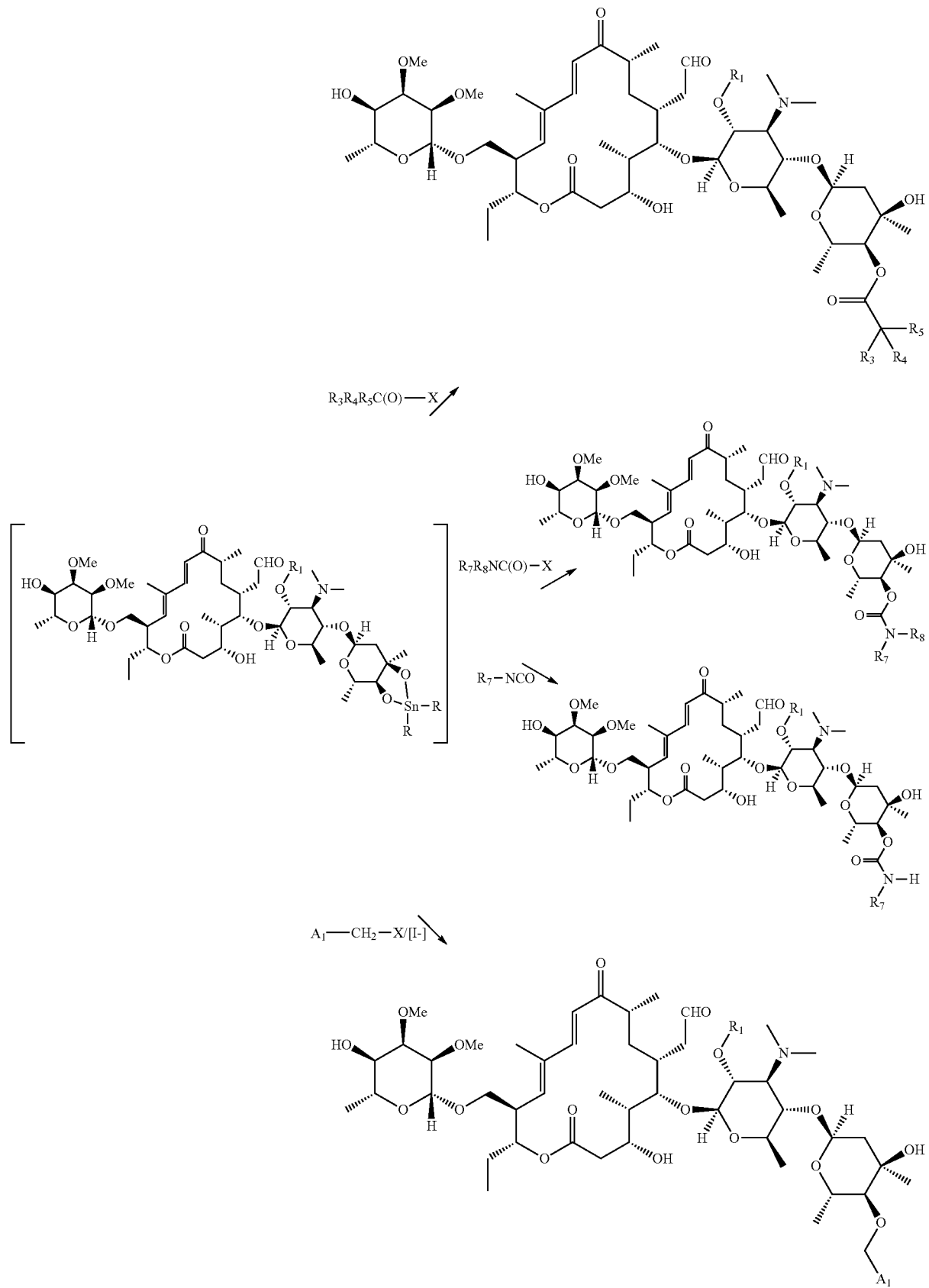

In the specific case where the 2'-substituent is acetyl, the resultant 2'-OAc/4"-substituted analog may (as in Scheme 3) be warmed in an alcohol like methanol or the like, optionally in the presence of a catalyst like solid sodium bicarbonate or the like, to hydrolyze the 2'-ester, resulting in the production of a 2'-unsubstituted, 4"-substituted analog.

SCHEME 3

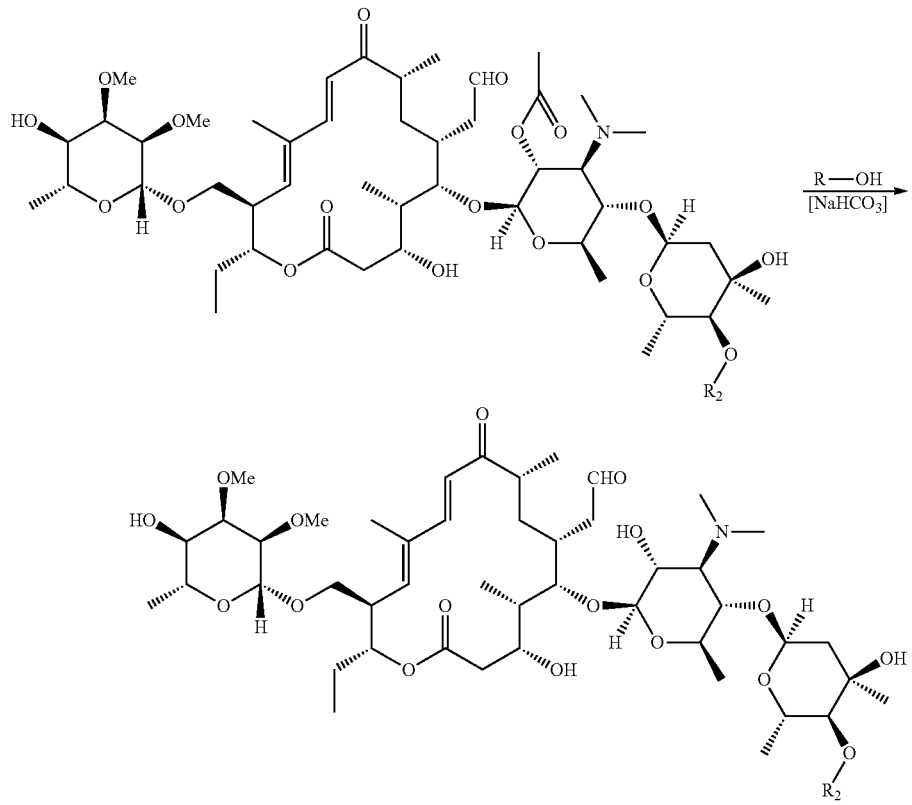

To prepare compounds that are simultaneously modified at the 2', 4", and 4'" positions, a 2'/4"-derivatized intermediate (prepared as described in Scheme 2) is treated with an acylating agent like acetic anhydride, or propionic anhydride, or the like, in a basic solvent like pyridine or lutidine or the like, as shown in Scheme 4. In the specific case where the 2'-substituent is acetyl, the resultant 2'-OAc/4"/4'"-substituted analog may be warmed in an alcohol like methanol or the like, optionally in the presence of a catalyst like solid sodium bicarbonate or the like, to hydrolyze the 2'-ester, resulting in the production of a 2'-unsubstituted, 4"/4'"-disubstituted analog.

SCHEME 4

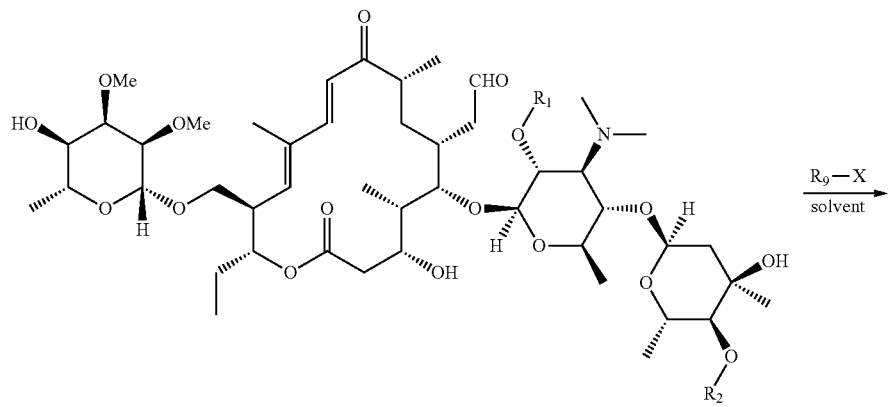

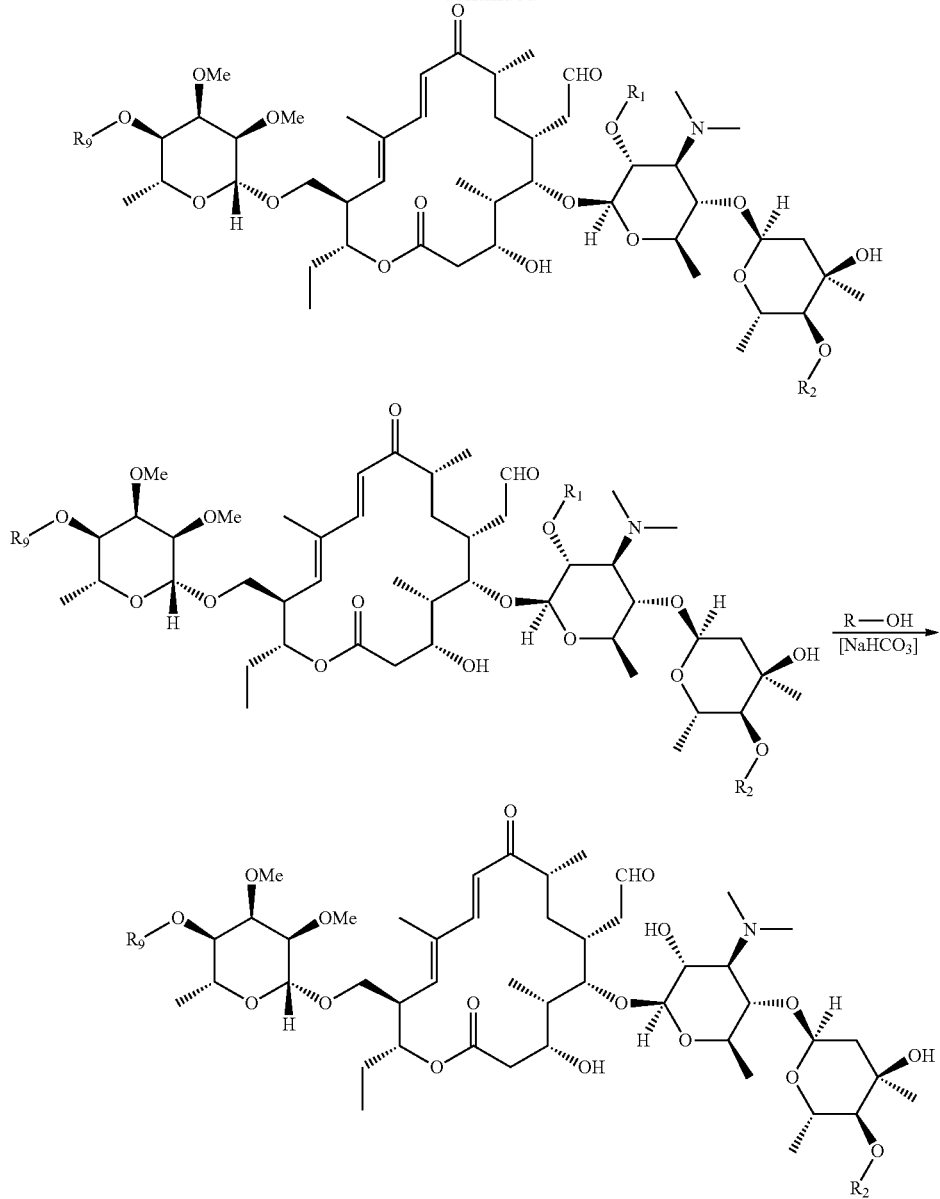

To prepare compounds that are reduced at the 10/11 and/or 12/13 positions, the corresponding unsaturated compound may be treated with hydrogen gas, or a hydrogen source like ammonium formate or the like, in the presence of a hydrogenation catalyst like palladium-on-carbon or platinum-on-carbon or Raney nickel or the like, in a solvent like ethanol or ethyl acetate or the like. By controlling the time, temperature, solvent and concentration of the reaction, one or both of the 10/11 and 12/13 double bonds may be reduced to single bonds.

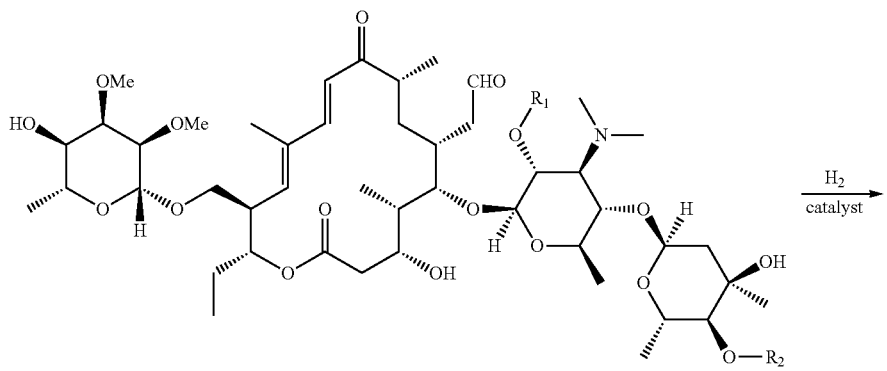

-continued

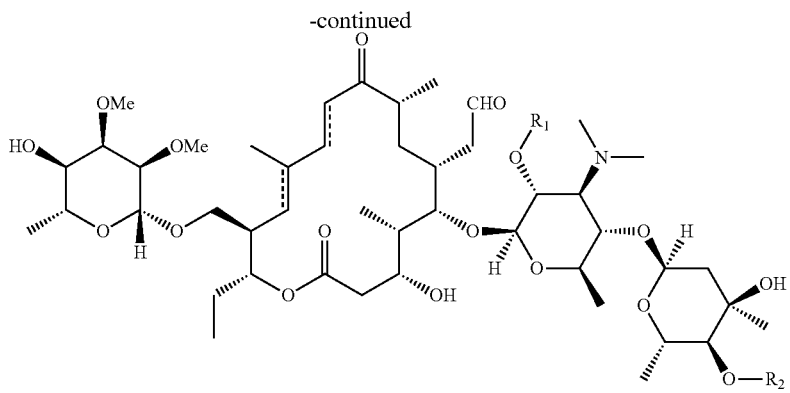

The present compounds and intermediates may be isolated and purified by conventional methods in the field of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub. Longman Scientific & Technical, Essex CM20 2JE, England.

The present compounds have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, benzenesulfonic, carbonic, fumaric, maleic, gluconic, acetic, propionic, salicylic, hydrochloric, hydrobromic, phosphoric, sulfuric, citric, hydroxybutyric, camphorsulfonic, malic, phenylacetic, aspartic, or glutamic acid, and the like. In certain embodiments, a compound may be reacted with a weak acid to provide the desired salt. Examples of suitable weak acids, but are not limited to, tartaric acid, lactic acid, acetic acid, propionic acid, citric acid, malic acid, and the like. In certain embodiments, the acid is tartaric acid.

Optimum reaction conditions and reaction times for each individual step can vary depending on the particular reactants employed and substituents present in the reactants used. Unless otherwise specified, solvents, temperatures and other reaction conditions can be readily selected. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature.

Routine experimentations, including appropriate manipulation of the reaction conditions, reagents and sequence of the synthetic route, protection of any chemical functionality that is not compatible with the reaction conditions, and deprotection at a suitable point in the reaction sequence of the method are included in the scope of the invention. Suitable protecting groups and the methods for protecting and deprotecting different substituents using such suitable protecting groups are well known; examples of which can be found in PGM Wuts and TW Greene, Greene's Protective Groups in Organic Synthesis (4th ed.), John Wiley & Sons, NY (2006), which is incorporated herein by reference in its entirety. Synthesis of the present compounds can be accomplished by methods analogous to those described in the synthetic schemes described hereinabove and in specific examples.

Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be obtained by carrying out one of the above procedures using a pure geometric isomer as a starting material, or by resolution of a mixture of the geometric isomers of the compound or intermediates using a standard procedure such as chromatographic separation.

It can be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

D. Compositions

In at least one aspect, the present invention includes compositions comprising a compound described herein or a salt thereof. In certain embodiments, the composition comprises a compound of Formula (I) or a salt thereof. In certain embodiments, the composition comprises a compound of Formula (II) or a salt thereof. In certain embodiments, the composition comprises a compound of Formula (III) or a salt thereof. In certain embodiments, the composition comprises a compound of Formula (IV) or a salt thereof. In certain embodiments, the composition comprises a compound of Formula (V) or a salt thereof. In certain embodiments, the composition comprises a compound of Formula (VI) or a salt thereof. In certain embodiments, the composition comprises a compound of Formula (VII) or a salt thereof. In certain embodiments, the composition comprises a compound of Formula (VIII) or a salt thereof. In certain embodiments, the composition comprises a compound of Formula (IX) or a salt thereof.

In certain embodiments, the composition comprises one or more conventional pharmaceutically acceptable carriers. Pharmaceutically acceptable carriers include, without limitation, a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations. Formulation of drugs is generally discussed in, for example, Hoover, J., Remington's Pharmaceutical Sciences (Mack Publishing Co., 1975) and Ansel's Pharmaceutical Dosage Forms and Drug Delivery Systems (Lippincott Williams & Wilkins, 2005).

In at least one aspect, the present invention includes pharmaceutical compositions comprising a therapeutically effective amount of a compound described herein in combination with one or more pharmaceutically acceptable carriers. In certain embodiments, the pharmaceutical compositions comprise a compound of formula (I) or a salt thereof formulated together with one or more pharmaceutically acceptable carriers. In certain embodiments, the pharmaceutical compositions comprise a compound of formula (II) or a salt thereof formulated together with one or more pharmaceutically acceptable carriers. In certain embodiments, the pharmaceutical compositions comprise a compound of formula (III) or a salt thereof formulated together with one or more pharmaceutically acceptable carriers. In certain embodiments, the pharmaceutical compositions comprise a compound of formula (IV) or a salt thereof formulated together with one or more pharmaceutically acceptable carriers. In certain embodiments, the pharmaceutical compositions comprise a compound of formula (V) or a salt thereof formulated together with one or more pharmaceutically acceptable carriers. In certain embodiments, the pharmaceutical compositions comprise a compound of formula (VI) or a salt thereof formulated together with one or more pharmaceutically acceptable carriers. In certain embodiments, the pharmaceutical compositions comprise a compound of formula (VII) or a salt thereof formulated together with one or more pharmaceutically acceptable carriers. In certain embodiments, the pharmaceutical compositions comprise a compound of formula (VIII) or a salt thereof formulated together with one or more pharmaceutically acceptable carriers. In certain embodiments, the pharmaceutical compositions comprise a compound of formula (IX) or a salt thereof formulated together with one or more pharmaceutically acceptable carriers.

The pharmaceutical compositions may be formulated for any route of administration. The pharmaceutical compositions can be administered to humans and other animals orally, nasally, rectally, parenterally, intracisternally, intravaginally, intraperitoneally, topically (as by powders, ointments or drops), or bucally. The term "parenterally", as used herein, refers to modes of administration which include intravenous, intramuscular, intraperitoneal, intrasternal, subcutaneous, intraarticular injection and infusion.

In certain embodiments, the pharmaceutical compositions are formulated for oral administration in solid or liquid form.

In certain embodiments, the pharmaceutical composition is a solid dosage form for oral administration. Solid dosage forms for oral administration include capsules, tablets, pills, powders, and granules. In certain embodiments, the pharmaceutical composition includes, for example, lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol. In certain embodiments, the pharmaceutical composition is tableted or encapsulated for convenient administration. In certain embodiments, such capsules or tablets contain a controlled-release formulation, as can be provided in, for example, a dispersion of the compound or salt in hydroxypropylmethyl cellulose. In the case of capsules, tablets, and pills, the dosage forms also can comprise buffering agents, such as sodium citrate, or magnesium or calcium carbonate or bicarbonate. Tablets and pills additionally can be prepared with enteric coatings.

In certain embodiments, the pharmaceutical composition is a liquid dosage form for oral administration. Liquid dosage forms for oral administration include, for example, pharmaceutically acceptable emulsions (including both oil-in-water and water-in-oil emulsions), solutions (including both aqueous and non-aqueous solutions), suspensions (including both aqueous and non-aqueous suspensions), syrups, and elixirs. In certain embodiments, the liquid dosage forms contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof. In addition, in certain embodiments, oral compositions, also include wetting, emulsifying, suspending, flavoring (e.g., sweetening), and/or perfuming agents.

Parenteral administration includes subcutaneous injections, intravenous injections, intramuscular injections, intrasternal injections, and infusion. Injectable preparations (e.g., sterile injectable aqueous or oleaginous suspensions) can be formulated according to the known art using suitable dispersing, wetting agents, and/or suspending agents. Acceptable vehicles and solvents include, for example, water, 1,3-butanediol, Ringer's solution, isotonic sodium chloride solution, bland fixed oils (e.g., synthetic mono- or diglycerides), fatty acids (e.g., oleic acid), dimethyl acetamide, surfactants (e.g., ionic and non-ionic detergents), and/or polyethylene glycols.

In certain embodiments, the pharmaceutical composition is for parenteral administration. In certain embodiments, formulations for parenteral administration are prepared from sterile powders or granules having one or more of the carriers or excipients mentioned for use in the formulations for oral administration. In certain embodiments, a compound or salt thereof is dissolved in water, polyethylene glycol, propylene glycol, ethanol, corn oil, cottonseed oil, peanut oil, sesame oil, benzyl alcohol, sodium chloride, and/or various buffers. In certain embodiments, the pH is adjusted, if necessary, with a suitable acid, base, or buffer.

In certain embodiments, the pharmaceutical composition is for rectal or vaginal administration. Compositions for rectal or vaginal administration are preferably suppositories that can be prepared by, for example, mixing a compound or salt thereof with a suitable nonirritating carrier or excipient that is solid at ordinary room temperatures, but liquid at body temperature. Suitable carriers or excipients include, for example, cocoa butter; synthetic mono-, di-, or triglycerides, fatty acids, and/or polyethylene glycols.

Topical administration includes the use of transdermal administration, such as transdermal patches or iontophoresis devices.

Other carriers and modes of administration known in the pharmaceutical art also may be used.

In at least one aspect, the compounds are used in the form of pharmaceutically acceptable salts or esters, or amides derived from inorganic or organic acids. In certain embodiments, pharmaceutically acceptable salts are those salts that are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the field. The salts can be prepared in situ during the final isolation and purification of the present compounds or separately by, for example, reacting a free base function with a suitable organic acid.

Representative pharmaceutically acceptable salts include, but are not limited to, acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate.

Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

In certain embodiments, pharmaceutically acceptable acid addition salts of the compounds of Formula (I), (II), (III), (IV), (V), (VI), (VII), (VIII), or (IX) are prepared from an inorganic or organic acid. Examples of acids which can be employed to form pharmaceutically acceptable acid addition salts include inorganic acids such as hydrochloric acid, hydrobromic acid, sulphuric acid and phosphoric acid and organic acids such as acetic acid, oxalic acid, maleic acid, succinic acid, tartaric acid, and citric acid. In certain embodiments, a weak acid, including, but not limited to, tartaric acid, lactic acid, acetic acid, propionic acid, citric acid, malic acid, and the like, can be employed to form pharmaceutically acceptable acid addition salt.

In certain embodiments, pharmaceutically acceptable base addition salts of the compounds of Formula (I), (II), (III), (IV), (V), (VI), (VII), (VIII), or (IX) include, for example, metallic salts and organic salts. In certain embodiments, pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylammonium, dimethylammonium, trimethylammonium, triethylammonium, diethylammonium, ethylammonium and the like. Other representative organic amines useful for the formation of base addition salts include ethylenediamine, ethanolamine, diethanolamine, piperidine, and piperazine.

In at least one aspect, the present invention includes a composition comprising one or more macrolide compounds or a salt thereof. In certain embodiments, at least 50% of the macrolide compounds in the composition are a compound of Formula (I), (II), (III), (IV), (V), (VI), (VII), (VIII), (IX), or a salt thereof. In certain embodiments, at least 60% of the macrolide compounds in the composition are a compound of Formula (I), (II), (III), (IV), (V), (VI), (VII), (VIII), (IX), or a salt thereof. In certain embodiments, at least 80% of the macrolide compounds in the composition are a compound of Formula (I), (II), (III), (IV), (V), (VI), (VII), (VIII), (IX), or a salt thereof. In certain embodiments, at least 80% of the macrolide compounds in the composition are a compound of Formula (I), (II), (III), (IV), (V), (VI), (VII), (VIII), (IX), or a salt thereof. In certain embodiments, at least 90% of the macrolide compounds in the composition are a compound of Formula (I), (II), (III), (IV), (V), (VI), (VII), (VIII), (IX), or a salt thereof. In certain embodiments, at least 95% of the macrolide compounds in the composition are a compound of Formula (I), (II), (III), (IV), (V), (VI), (VII), (VIII), (IX), or a salt thereof.

In certain embodiments, a compound, such as a compound of Formula (I), (II), (III), (IV), (V), (VI), (VII), (VIII), (IX), or a salt thereof is included as an additive to animal feed or drinking water for animals. In certain embodiments, the compound is formulated into premixes in various potencies from 1 to 10% by weight.

The compositions for use either as feed additives or as directly administered preparations may contain any convenient proportion of the compound, for example from 1% or less to 90% or more, by weight. Liquid formulations typically contain 50 to 90% by weight, whereas solid formulations typically contain 1 to 25% by weight.

E. Methods of Use

In at least one aspect, the present invention includes a method of treating or preventing a bacterial infection in a subject in need of treatment or prevention of a bacterial infection. In certain embodiments, the subject is a mammal. In certain embodiments, the mammal is a human. In certain embodiments, mammals include ruminant herbivores such as cattle, goats, and sheep. In certain embodiments, the subject includes poultry. In certain embodiments, the methods comprise administering to the subject a therapeutically effective amount of a compound of Formula (I) or a pharmaceutically acceptable salt thereof. In certain embodiments, the methods comprise administering to the subject a therapeutically effective amount of a compound of Formula (II) or a pharmaceutically acceptable salt thereof. In certain embodiments, the methods comprise administering to the subject a therapeutically effective amount of a compound of Formula (III) or a pharmaceutically acceptable salt thereof. In certain embodiments, the methods comprise administering to the subject a therapeutically effective amount of a compound of Formula (IV) or a pharmaceutically acceptable salt thereof. In certain embodiments, the methods comprise administering to the subject a therapeutically effective amount of a compound of Formula (V) or a pharmaceutically acceptable salt thereof. In certain embodiments, the methods comprise administering to the subject a therapeutically effective amount of a compound of Formula (VI) or a pharmaceutically acceptable salt thereof. In certain embodiments, the methods comprise administering to the subject a therapeutically effective amount of a compound of Formula (VII) or a pharmaceutically acceptable salt thereof. In certain embodiments, the methods comprise administering to the subject a therapeutically effective amount of a compound of Formula (VIII) or a pharmaceutically acceptable salt thereof. In certain embodiments, the methods comprise administering to the subject a therapeutically effective amount of a compound of Formula (IX) or a pharmaceutically acceptable salt thereof. Preferably, the methods comprise administering to the subject a therapeutically effective amount of any of the compounds as described herein, or a pharmaceutically acceptable salt thereof.

In at least one aspect, the present invention includes a method of treating a mammal infected with a Gram-positive bacterium such as *Staphylococcus aureus, Staphylococcus epidermidis, Enterococcus faecalis*, or *Streptococcus pneumoniae*. In certain embodiments, the methods comprise administering to the mammal a therapeutically effective amount of a compound of Formula (I) or a pharmaceutically acceptable salt thereof. In certain embodiments, the methods comprise administering to the mammal a therapeutically effective amount of a compound of Formula (II) or a pharmaceutically acceptable salt thereof. In certain embodiments, the methods comprise administering to the mammal a therapeutically effective amount of a compound of Formula (III) or a pharmaceutically acceptable salt thereof. In certain embodiments, the methods comprise administering to the mammal a therapeutically effective amount of a compound of Formula (IV) or a pharmaceutically acceptable salt thereof. In certain embodiments, the methods comprise administering to the mammal a therapeutically effective amount of a compound of Formula (V) or a pharmaceutically acceptable salt thereof. In certain embodiments, the methods comprise administering to the mammal a therapeutically effective amount of a compound of Formula (VI) or a pharmaceutically acceptable salt thereof. In certain embodiments, the methods comprise administering to the mammal a therapeutically effective amount of a compound of Formula (VII) or a pharmaceutically acceptable salt thereof. In certain embodiments, the methods comprise administering to the mammal a therapeutically effective amount of a compound of Formula (VIII) or a pharmaceutically acceptable salt thereof. In certain embodiments, the methods comprise administering to the mammal a therapeutically effective amount of a compound of Formula (IX) or a pharmaceutically acceptable salt thereof. Preferably, the methods comprise administering to the mammal a therapeutically effective amount of any of the compounds as described herein, or a pharmaceutically acceptable salt thereof.

In at least one aspect, the present invention includes a method of treating a mammal infected with a Gram-negative bacterium such as *Haemophilus influenzae*. In certain embodiments, the methods comprise administering to the mammal a therapeutically effective amount of a compound of Formula (I) or a pharmaceutically acceptable salt thereof. In certain embodiments, the methods comprise administering to the mammal a therapeutically effective amount of a compound of Formula (II) or a pharmaceutically acceptable salt thereof. In certain embodiments, the methods comprise administering to the mammal a therapeutically effective amount of a compound of Formula (III) or a pharmaceutically acceptable salt thereof. In certain embodiments, the methods comprise administering to the mammal a therapeutically effective amount of a compound of Formula (IV) or a pharmaceutically acceptable salt thereof. In certain embodiments, the methods comprise administering to the mammal a therapeutically effective amount of a compound of Formula (V) or a pharmaceutically acceptable salt thereof. In certain embodiments, the methods comprise administering to the mammal a therapeutically effective amount of a compound of Formula (VI) or a pharmaceutically acceptable salt thereof. In certain embodiments, the methods comprise administering to the mammal a therapeutically effective amount of a compound of Formula (VII) or a pharmaceutically acceptable salt thereof. In certain embodiments, the methods comprise administering to the mammal a therapeutically effective amount of a compound of Formula (VIII) or a pharmaceutically acceptable salt thereof. In certain embodiments, the methods comprise administering to the mammal a therapeutically effective amount of a compound of Formula (IX) or a pharmaceutically acceptable salt thereof. Preferably, the methods comprise administering to the mammal a therapeutically effective amount of any of the compounds as described herein, or a pharmaceutically acceptable salt thereof.

Another aspect of the present invention pertains to the use of compounds of Formula (I) to treat or prevent a bacterial infection in a mammal. The present compounds are regarded as active against Gram-positive and/or Gram-negative bacterial pathogens. In particular, the present compounds are active against at least one Gram-positive bacterium, preferably against several Gram-positive bacteria, more preferably against one or more Gram-positive bacteria and/or one or more Gram-negative bacteria. For example, compounds of Formula (I) exert antibacterial activity against various mammalian pathogens, including Gram-positive bacteria such as Staphylococi, Enterococci and Streptococi. In particular, compounds of Formula (I) exert antibacterial activity against Gram-positive bacteria such as *Staphylococcus aureus, Staphylococcus epidermidis, Enterococcus faecalis*, and *Streptococcus pneumoniae*. Compounds of Formula (I) exert antibacterial activity against Gram-negative bacteria such as *Haemophilus influenzae*.

Yet another aspect of the present invention includes the use of a compound of Formula (I), (II), (III), (IV), (V), (VI), (VII), (VIII), or (IX), or a salt thereof, for the treatment of an infection with a Gram-positive and/or a gram-negative bacterium. In certain embodiments, the use is for the treatment of an infection with a Gram-positive bacterium. In certain embodiments, the use is for the treatment of an infection with a Gram-negative bacterium.

Still another aspect of the present invention includes a method for inhibiting growth and/or replication of bacteria.

The method comprises exposing the bacteria to a compound of Formula (I), (II), (III), (IV), (V), (VI), (VII), (VIII), or (IX), or a salt thereof. In certain embodiments, growth and/or replication of the bacteria are inhibited in vitro. In other embodiments, growth and/or replication of the bacteria are inhibited in vivo. For example, in certain embodiments, bacteria within a mammalian host are exposed to a compound of Formula (I), (II), (III), (IV), (V), (VI), (VII), (VIII), or (IX), or a salt thereof in an amount effective to inhibit bacterial growth or replication. In certain embodiments, the bacteria are Gram-positive bacteria. In other embodiments, the bacteria are Gram-negative bacteria.

Still another aspect of the present invention includes a method for inhibiting protein synthesis in a bacterium. The method comprises exposing the bacterium to a compound of Formula (I), (II), (III), (IV), (V), (VI), (VII), (VIII), or (IX), or a salt thereof. In certain embodiments, protein synthesis is inhibited in vitro. In other embodiments, protein synthesis is inhibited in vivo. In certain embodiments, the bacterium is a Gram-positive bacterium. In other embodiments, the bacterium is a Gram-negative bacterium.

The preferred total daily dose of the compound or salt (administered in single or divided doses) is typically from about 0.001 to about 100 mg/kg, more preferably from about 0.001 to about 30 mg/kg, and even more preferably from about 0.01 to about 10 mg/kg (i.e., mg of the compound or salt per kg body weight). In certain embodiments, dosage unit compositions contain such amounts or submultiples thereof to make up the daily dose. In many instances, the administration of the compound or salt will be repeated a plurality of times. In certain embodiments, multiple doses per day typically may be used to increase the total daily dose, if desired.

Factors affecting the preferred dosage regimen include the type, age, weight, sex, diet, and condition of the patient; the severity of the pathological condition; the route of administration; pharmacological considerations, such as the activity, efficacy, pharmacokinetic, and toxicology profiles of the particular compound or salt used; whether a drug delivery system is utilized; and whether the compound or salt is administered as part of a drug combination. Thus, the dosage regimen actually employed can vary widely, and therefore, can derive from the preferred dosage regimen set forth above.

The antibacterial activity of a compound can be determined using various known methods, including in vitro and in vivo antibacterial assays. For example, antibacterial activity can be determined using a broth microdilution assay as further described herein.

The compounds, compositions, and methods described herein will be better understood by reference to the following examples, which are included as an illustration of and not a limitation upon the scope of the invention.

F. Examples

Compounds 1-37 having structures as shown in Table 1 were prepared as described below:

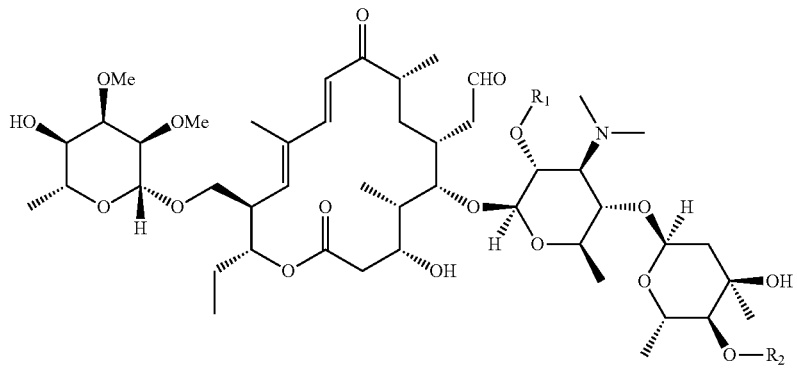

TABLE 1

| Compound | $R_1$ | $R_2$ |
|---|---|---|
| 1 | $C(O)CH_3$ | —CH$_2$—C$_6$H$_5$ |
| 2 | $C(O)CH_3$ | —CH$_2$—C$_6$H$_4$—CF$_3$ |
| 3 | $C(O)CH_3$ | —CH$_2$—C$_6$H$_4$—F |
| 4 | $C(O)CH_3$ | —CH$_2$—C$_6$H$_4$—Cl |
| 5 | $C(O)CH(CH_3)_2$ | —CH$_2$—C$_6$H$_5$ |
| 6 | $C(O)CH(CH_3)_2$ | —CH$_2$—(2,4-F$_2$-C$_6$H$_3$) |
| 7 | $C(O)CH(CH_3)_2$ | —CH$_2$—(benzothiazol-2-yl) |
| 8 | $C(O)CH(CH_3)_2$ | —CH$_2$—C$_6$H$_4$—F |

TABLE 1-continued

| Compound | R₁ | R₂ |
|---|---|---|
| 9 | C(O)CH(CH₃)₂ | —CH₂-(1-naphthyl) |
| 10 | H | —CH₂-(4-F-C₆H₄) |
| 11 | C(O)(CH₂)₃CH₃ | —CH₂-(4-F-C₆H₄) |
| 12 | C(O)CH₃ | C(O)C(CH₃)₃ |
| 13 | C(O)CH(CH₃)₂ | C(O)C(CH₃)₃ |
| 14 | H | C(O)C(CH₃)₃ |
| 15 | C(O)CH₃ | C(O)N(CH₂CH₃)₂ |
| 16 | C(O)CH₃ | C(O)N(CH₃)(C₆H₅) |
| 17 | C(O)CH₃ | C(O)-pyrrolidinyl |
| 18 | C(O)CH(CH₃)₂ | C(O)N(CH₂CH₃)₂ |
| 19 | H | C(O)N(CH₂CH₃)₂ |
| 20 | C(O)CH₃ | C(O)-piperidinyl |
| 21 | C(O)CH₃ | C(O)-morpholinyl |
| 22 | C(O)CH₃ | C(O)N(CH(CH₃)₂)₂ |
| 23 | C(O)CH₃ | C(O)N((CH₂)₃CH₃)₂ |
| 24 | C(O)CH₃ | C(O)N(CH₂CH(CH₃)₂)₂ |
| 25 | C(O)CH₃ | C(O)-azepanyl |
| 26 | C(O)CH₃ | C(O)—N(C₆H₁₁)₂ |
| 27 | C(O)CH(CH₃)₂ | C(O)N(CH₃)₂ |
| 28 | C(O)CH(CH₃)₂ | C(O)N(CH₂CH₃)((CH₂)₃CH₃) |
| 29 | H | C(O)N(CH(CH₃)₂)₂ |
| 30 | H | C(O)N((CH₂)₃CH₃)₂ |
| 31 | H | C(O)—N(C₆H₁₁)₂ |
| 32 | C(O)CH(CH₃)₂ | C(O)-morpholinyl |
| 33 | C(O)CH₃ | —CH₂-(2,4-F₂-C₆H₃) |
| 34 | C(O)(CH₂)₃(CH₃) | C(O)-morpholinyl |
| 35 | C(O)(CH₂)₃(CH₃) | —CH₂-(2,4-F₂-C₆H₃) |
| 36 | H | C(O)-morpholinyl |
| 37 | H | —CH₂-(2,4-F₂-C₆H₃) |

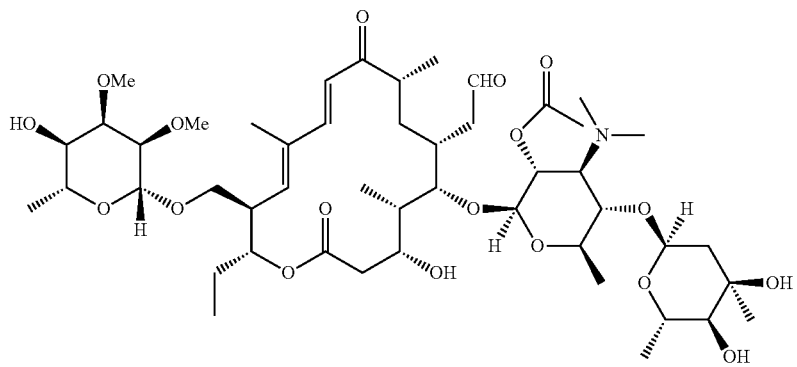 [SMILES: CC[C@H]1OC(=O)C[C@@H](O)[C@H](C)[C@@H](O[C@@H]2O[C@H](C)[C@@H](O[C@H]3C[C@@](C)(O)[C@@H](O)[C@H](C)O3)[C@H](N(C)C)[C@H]2OC(C)=O)[C@@H](CC=O)C[C@@H](C)C(=O)/C=C/C(C)=C/[C@@H]1CO[C@@H]1O[C@H](C)[C@@H](O)[C@@H](OC)[C@H]1OC]

Compound A. Tylosin A 2'-OAc

Using a modification of the procedures described in Tsuchiya et al, J Antibiotics 1982, (35), 661, tylosin A tartrate (5 mmol) was dissolved in 20 mL of ethanol; acetic anhydride (0.66 mL, 1.5 equivalents) was added and the resultant solution was stirred at 40 C for four hours. Reaction was quenched by addition of 20 mL of aqueous sodium bicarbonate; the mixture was stirred for 30 minutes, then poured into a separatory funnel and the organic layer was removed. The aqueous layer was extracted twice with 10 mL of chloroform. The combined organic layers were washed with brine and dried over $Na_2SO_4$. The crude product was carried forward without further purification.

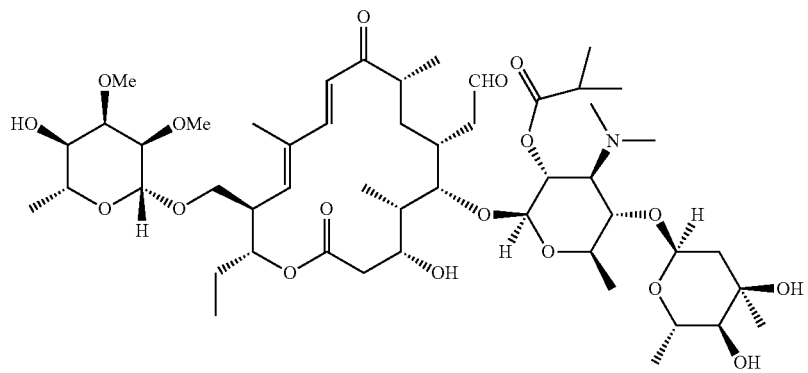 [SMILES: CC[C@H]1OC(=O)C[C@@H](O)[C@H](C)[C@@H](O[C@@H]2O[C@H](C)[C@@H](O[C@H]3C[C@@](C)(O)[C@@H](O)[C@H](C)O3)[C@H](N(C)C)[C@H]2OC(=O)C(C)C)[C@@H](CC=O)C[C@@H](C)C(=O)/C=C/C(C)=C/[C@@H]1CO[C@@H]1O[C@H](C)[C@@H](O)[C@@H](OC)[C@H]1OC]

Compound B Tylosin A 2'-OiBu

Compound B was prepared using procedure for the preparation of Compound A, except for substituting isobutyric anhydride (3.0 equivalents) for acetic anhydride, and using chloroform as solvent.

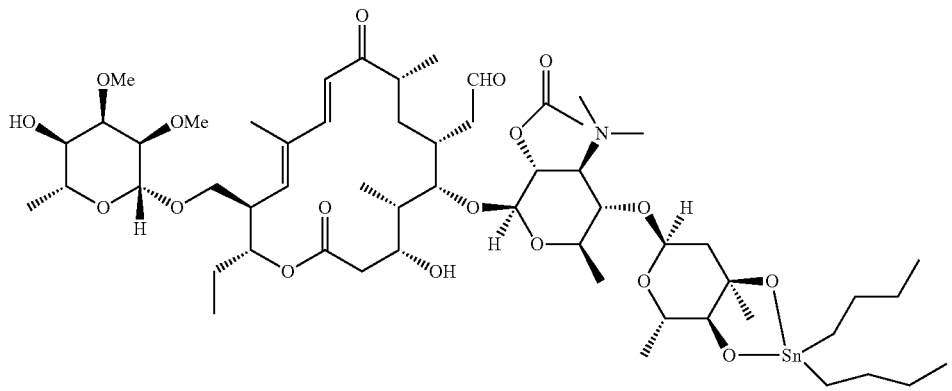

Compound C Tylosin A 2'-OAc, 3"/4" dibutyl tin reagent

Using a modification of the procedures described in Kiyoshima et al., Chem. Pharm. Bull. 1989, 37(4), 861, Compound A (10 mmol) was dissolved in 150 mL of toluene; followed by the addition of 7.5 g (3.0 equivalents) of dibutyltin oxide. The resultant mixture was stirred at reflux (bath temperature 115° C.) for 30 minutes. A still head was added and the bath temperature was raised to 130° C., distilling off solvents to a final volume of about 60 mL. The resultant solution was used for further reactions without additional purification.

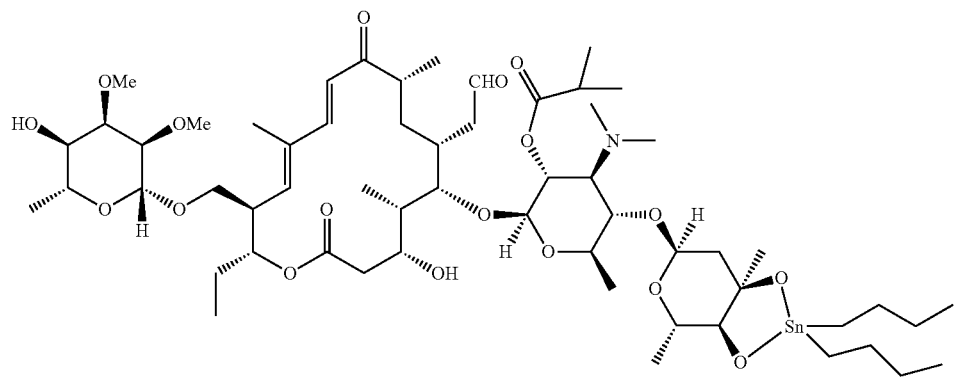 [SMILES: CCC[CH2][Sn]1([CH2]CCC)[O][C@H]2[C@H](C)O[C@@H](O[C@H]3[C@H](N(C)C)[C@@H](OC(=O)C(C)C)[C@H](O[C@H]4[C@@H](CC=O)C[C@@H](C)C(=O)/C=C/C(C)=C/[C@H](CO[C@@H]5O[C@H](C)[C@@H](O)[C@@H](OC)[C@H]5OC)[C@@H](CC)OC(=O)C[C@@H](O)[C@@H]4C)O[C@@H]3C)C[C@@]2(C)[O]1]

Compound D Tylosin A 2'-OiBu, 3"/4" dibutyl tin reagent

Using a modification of the procedures described in Kiyoshima et al., Chem. Pharm. Bull. 1989, 37(4), 861, Compound B (10 mmol) was dissolved in 150 mL of toluene; followed by the addition of 7.5 g (3.0 equivalents) of dibutyltin oxide. The resultant mixture was stirred at reflux (bath temperature 115° C.) for 30 minutes. A still head was added and the bath temperature was raised to 130° C., distilling off solvents to a final volume of about 60 mL. The resultant solution was used for further reactions without additional purification.

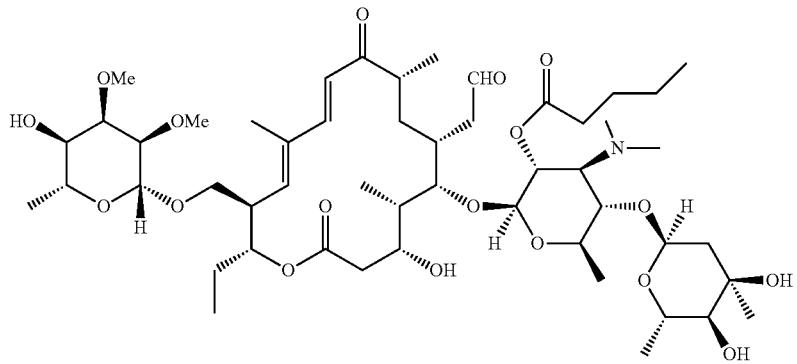 [SMILES: CCCCC(=O)O[C@H]1[C@H](O[C@H]2[C@@H](CC=O)C[C@@H](C)C(=O)/C=C/C(C)=C/[C@H](CO[C@@H]3O[C@H](C)[C@@H](O)[C@@H](OC)[C@H]3OC)[C@@H](CC)OC(=O)C[C@@H](O)[C@@H]2C)O[C@H](C)[C@@H](O[C@H]2C[C@@](C)(O)[C@@H](O)[C@H](C)O2)[C@@H]1N(C)C]

Compound E. Tylosin A 2'-OVal

Using a modification of the procedures described in Tsuchiya et al, J Antibiotics 1982, (35), 661, tylosin A tartrate (3 mmol) was dissolved in 15 mL of chloroform; valeric anhydride (0.89 mL, 1.5 equivalents) was added and the resultant solution was stirred at ambient temperature for 41 hours. Reaction was quenched by addition of 5 mL of aqueous sodium bicarbonate; the mixture was stirred for 30 minutes, then poured into a separatory funnel and the organic layer was removed. The aqueous layer was extracted with 5 mL of chloroform. The combined organic layers were washed with brine and dried over $Na_2SO_4$. The crude product was carried forward without further purification.

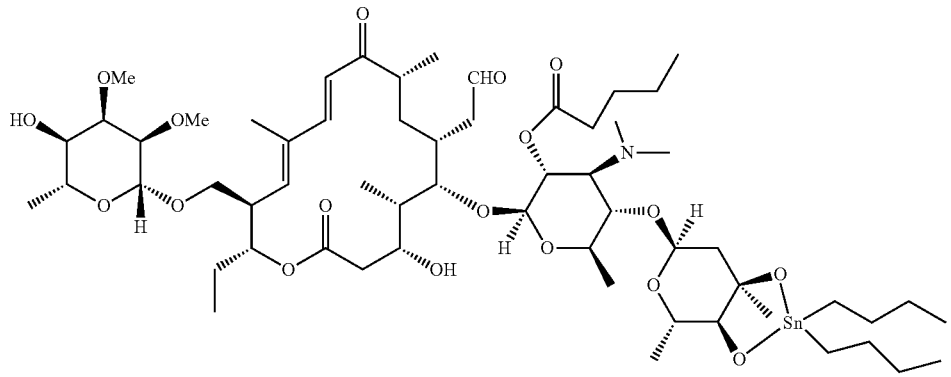

Compound F Tylosin A 2'-OVal, 3"/4" dibutyl tin reagent

Using a modification of the procedures described in Kiyoshima et al., Chem. Pharm. Bull. 1989, 37(4), 861, Compound E (3 mmol) was dissolved in 50 mL of toluene; followed by the addition of 2.24 g (3.0 equivalents) of dibutyltin oxide. The resultant mixture was stirred at reflux (bath temperature 115° C.) for 30 minutes. A still head was added and the bath temperature was raised to 130° C., distilling off solvents to a final volume of about 20 mL. The resultant solution was used for further reactions without additional purification.

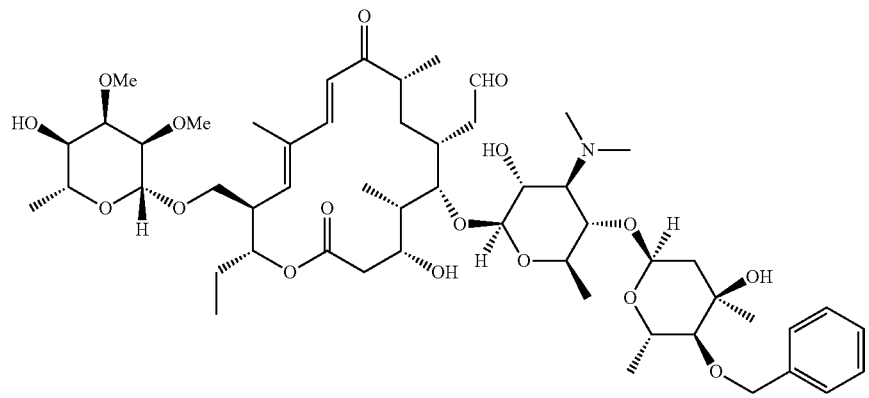 [SMILES: CC[C@H]1OC(=O)C[C@@H](O)[C@H](C)[C@@H](O[C@@H]2O[C@H](C)[C@@H](O[C@H]3C[C@@](C)(O)[C@@H](OCc4ccccc4)[C@H](C)O3)[C@H](N(C)C)[C@H]2O)[C@@H](CC=O)C[C@@H](C)C(=O)/C=C/C(C)=C/[C@@H]1CO[C@@H]1O[C@H](C)[C@@H](O)[C@@H](OC)[C@H]1OC]

Compound G Tylosin A 4" O-benzyl

Compound 1 (1.05 g, 1 mmol) was dissolved in methanol (20 mL) and heated at 65° C. for 40 hours. Solvents were removed in vacuo to provide the title compound.

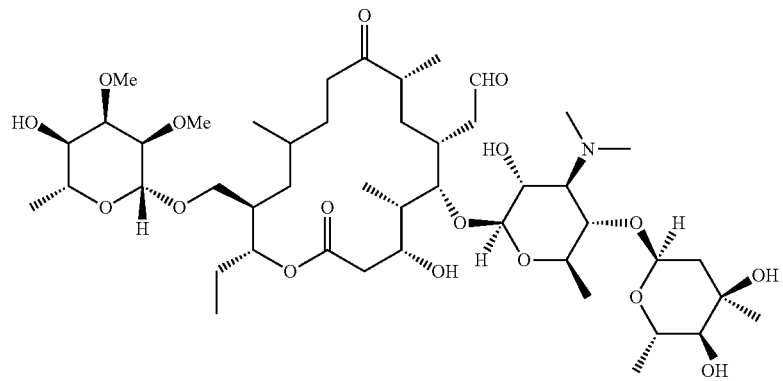 [SMILES: CC[C@H]1OC(=O)C[C@@H](O)[C@H](C)[C@@H](O[C@@H]2O[C@H](C)[C@@H](O[C@H]3C[C@@](C)(O)[C@@H](O)[C@H](C)O3)[C@H](N(C)C)[C@H]2O)[C@@H](CC=O)C[C@@H](C)C(=O)CCC(C)C[C@@H]1CO[C@@H]1O[C@H](C)[C@@H](O)[C@@H](OC)[C@H]1OC]

Compound H 10,11,12,13-tetrahydro-Tylosin A

The title compound was prepared according to the procedure of Narandja et al., J. Antibiotics 1995, 48930, 248.

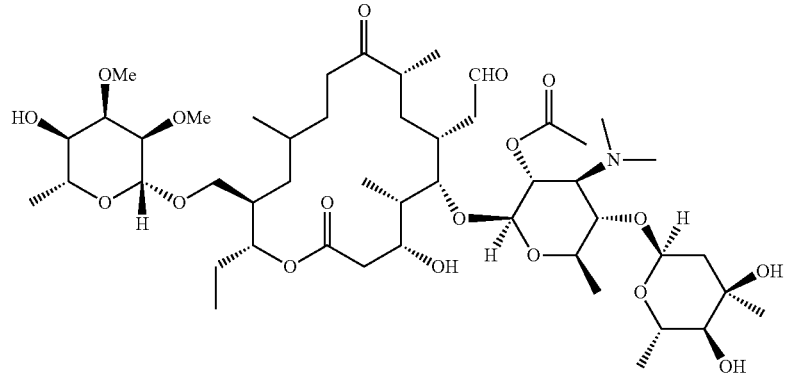 [SMILES: CC[C@H]1OC(=O)C[C@@H](O)[C@H](C)[C@@H](O[C@@H]2O[C@H](C)[C@@H](O[C@H]3C[C@@](C)(O)[C@@H](O)[C@H](C)O3)[C@H](N(C)C)[C@H]2OC(C)=O)[C@@H](CC=O)C[C@@H](C)C(=O)CCC(C)C[C@@H]1CO[C@@H]1O[C@H](C)[C@@H](O)[C@@H](OC)[C@H]1OC]

Compound J 2'-OAc, 10,11,12,13-tetrahydro-Tylosin A

Compound H (1.53 g) was dissolved in 10 mL of ethanol; 0.25 mL of acetic anhydride was added, and the resultant solution was stirred at 40° C. for 2 hours. The solution was concentrated in vacuo; the residue was taken up in chloroform and stirred with aqueous sodium bicarbonate solution for ten minutes. The mixture was poured into a separatory funnel; the organic layer was removed and the aqueous layer was extracted with chloroform. The combined organic layers were dried over solid sodium sulfate, filtered and concentrated in vacuo to give the title compound.

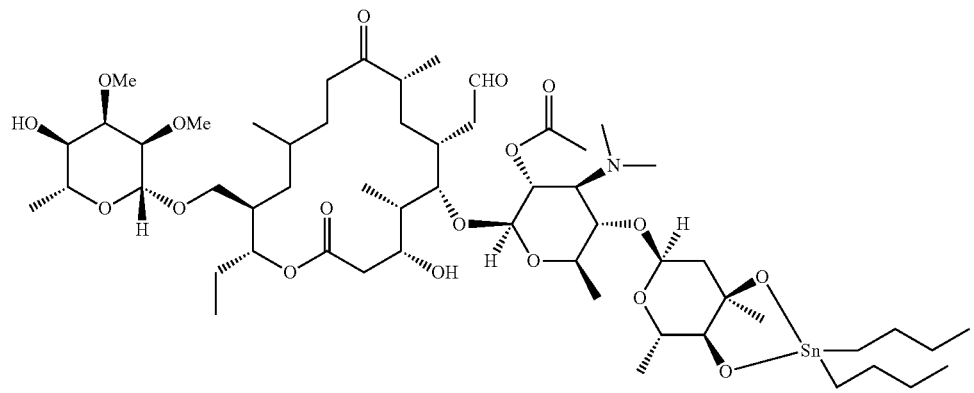

Compound K 2'-OAc, 10,11,12,13-tetrahydro-Tylosin A, tin reagent

Using a modification of the procedures described in Kiyoshima et al., Chem. Pharm. Bull. 1989, 37(4), 861, Compound J (1.60 g) was dissolved in 25 mL of toluene; followed by the addition of 0.62 g (1.5 equivalents) of dibutyltin oxide. The resultant mixture was stirred at reflux (bath temperature 115° C.) for 30 minutes. A still head was added and the bath temperature was raised to 140° C., distilling off solvents to a final volume of about 10 mL. The resultant solution was used for further reactions without additional purification.

Compound 1

Compound C (1 mmol) in 6 mL toluene solution, was combined with benzyl bromide (1.5 equivalents) and 20 mg of tetra-n-butylammonium iodide. The resultant mixture was heated at 90° C. for 2 days. Reaction was quenched with aqueous sodium bicarbonate and stirred for ten minutes. The layers were separated and the organic layer was washed with brine. Combined aqueous layer was extracted with chloroform. Combined organic layers were dried over Na$_2$SO$_4$, filtered, and concentrated. The residue was chromatographed on a 50 g silica gel column, eluting with a gradient from 1:1 ethyl acetate/hexanes to 100% ethyl acetate. The title compound was collected as a white solid.

Compound 2

Compound 2 was prepared using the procedure for the preparation of Compound 1, except for substituting 4-trifluoromethylbenzyl bromide for benzyl bromide. The crude product was purified by HPLC on a Waters Sunfire C8 column, eluting with a gradient of 35%/50%/87%/100% methanol in 0.1% ammonium acetate.

Compound 3

Compound C (1.25 mmol) in 20 mL toluene solution, was combined with 4-fluorobenzyl bromide (2.0 equivalents) and 200 mg of tetra-n-butylammonium iodide. The resultant mixture was heated at 90° C. for 2 days. The reaction mixture was concentrated in vacuo; the residue was chromatographed on a 50 g silica gel column, eluting with a gradient from 20% ethyl acetate/hexanes to 100% ethyl acetate, producing the title compound.

Compound 4

Compound 4 was prepared using the procedure for the preparation of Compound 1, except for substituting 4-chlorobenzyl bromide for benzyl bromide. The crude product was purified by HPLC on a Waters Sunfire C8 column, eluting with a gradient of 35%/50%/87%/100% methanol in 0.1% ammonium acetate.

Compound 5

Compound 5 was prepared using the procedure for the preparation of Compound 1, except for substituting Compound D for Compound C. The crude product was purified by chromatography on a silica gel column, eluting with a gradient from 20% ethyl acetate/hexanes to 100% ethyl acetate.

Compound 6

Compound D (1.5 mmol) in 10 mL toluene solution, was combined with 2,4-difluorobenzyl bromide (2.5 equivalents) and 20 mg of tetra-n-butylammonium iodide. The resultant mixture was heated at 90° C. for 3 days. The solvents were removed in vacuo; the residue was chromatographed on a 50 g silica gel column, eluting with a gradient from 1:1 ethyl acetate/hexanes to 100% ethyl acetate, to produce the title compound.

Compound 7

Compound 7 was prepared using the procedure for the preparation of Compound 1, except for substituting Compound D for Compound C, and substituting 2-bromomethyl benzothiazole for benzyl bromide. The crude product was purified by HPLC on a Waters Sunfire C8 column, eluting with a gradient of 20%/60%/100% methanol in 0.1% ammonium acetate.

Compound 8

Compound D (4.7 mmol) in 20 m L of toluene, was combined with 4-fluorobenzyl bromide (2.0 eq) and 200 mg of tetra-n-butylammonium iodide. The resultant mixture was warmed at 90° C. for 60 hours. Solvents were removed in vacuo; the residue was chromatographed on a 100 g silica gel column, eluting with a gradient from 20% ethyl acetate/hexanes to 100% ethyl acetate, giving the title compound.

Compound 9

Compound 9 was prepared using the procedure for the preparation of Compound 1, except for substituting Compound D for Compound C, and substituting 1-naphthylmethyl bromide for benzyl bromide. The crude product was chromatographed on a 10 g silica column, eluting with a gradient from 20% ethyl acetate/hexanes to 100% ethyl acetate.

Compound 10

Compound 3 (5.0 mmol) was dissolved in 80 mL of methanol; 50 mg of solid sodium bicarbonate was added, and the resultant mixture was stirred at ambient temperature for 5 days. Solvents were removed in vacuo; the residue was chromatographed on a 50 g silica gel column, eluting with a gradient from 1:1 ethyl acetate/hexanes to ethyl acetate, providing the title compound.

Compound 11

Compound 10 (58 mg, 0.06 mmol) was dissolved in 0.5 mL of chloroform; three drops of valeric anhydride was added, and the solution was stirred at ambient temperature for 3 hours. Reaction was quenched with aqueous sodium bicarbonate; the resultant mixture was stirred for 10 minutes. The organic phase was removed and concentrated in vacuo. The crude product was purified by HPLC on a Waters Sunfire C8 column, eluting with a gradient of 60% to 100% acetonitrile in 0.1% ammonium acetate.

Compound 12

A solution of Compound C (1 mmol) in 20 mL of toluene was combined with pivaloyl chloride (0.18 g, 1.5 equivalents) and heated at 90° C. for 6 hours. Reaction was quenched by addition of aqueous sodium bicarbonate, the resultant mixture was stirred for ten minutes. The organic layer was separated and washed with brine. The combined aqueous layers was extracted with $CHCl_3$. The combined organic extracts were dried over $Na_2SO_4$, filtered, and concentrated. The residue was chromatographed on a 50 g silica column, eluting with a gradient of 1:1 ethyl acetate/hexane to 100% ethyl acetate to provide the title compound as a white solid.

Compound 13

Compound D (1 mmol) in 20 mL of toluene was combined with pivaloyl chloride (0.24 g, 2.0 equivalents) and heated at 90° C. for 4 hours. Reaction was quenched by the addition of aqueous sodium bicarbonate, the resultant mixture was stirred for ten minutes. The organic layer was separated and washed with brine. The combined aqueous layers was extracted with $CHCl_3$. The combined organic extracts were dried over $Na_2SO_4$, filtered, and concentrated. The residue was chromatographed on a 50 g silica column, eluting with a gradient of 1:1 ethyl acetate/hexane to 100% ethyl acetate to provide the title compound as a white solid.

Compound 14

Compound 12 (1.04 g, 1 mmol) was dissolved in methanol (20 mL). The mixture was heated at 65° C. for 40 hours and concentrated in vacuo to provide the title compound as a white solid.

Compound 15

Compound C (2 mmol in 20 mL of toluene) was combined with 0.5 mL of diethylcarbamoyl chloride. The resultant solution was warmed at 80° C. for 40 hours. Solvents were removed in vacuo to reduce the volume by about half. The remaining material was loaded onto a 50 g silica gel column and eluted with a gradient from 1:1 ethyl acetate/hexanes to 100% ethyl acetate, to produce the title compound.

Compound 16

Compound 16 was prepared using the procedure for the preparation of Compound 15, except for substituting N-methyl-N-phenylcarbamoyl chloride for diethylcarbamoyl chloride. The resulting mixture was heated at 90° C. for 5 days. The crude material was purified by HPLC on a Waters Sunfire C8 column, eluting with a gradient of 35%/50%/87%/100% methanol in 0.1% ammonium acetate.

Compound 17

Compound 17 was prepared using the procedure for the preparation of Compound 15, except for substituting pyrrolidinecarbamoyl chloride for diethylcarbamoyl chloride. The resulting mixture was heated at 90° C. for 5 hours. The crude material was purified by HPLC on a Waters Sunfire C8 column, eluting with a gradient of 35%/50%/87%/100% methanol in 0.1% ammonium acetate.

Compound 18

Compound D (10 mmol) in 50 mL of toluene) was combined with 4.44 mL (3.5 eq) of diethylcarbamoyl chloride. The resultant solution was warmed at 80° C. for 40 hours. The reaction mixture was poured onto a pad of 40 g of silica gel and eluted with 2×80 mL washes of ethyl acetate. The combined washes were concentrated in vacuo; the residue was loaded onto a 50 g silica gel column and eluted with a gradient from 1:1 ethyl acetate/hexanes to 100% ethyl acetate, to produce the title compound.

Compound 19

Compound 15 (2.12 g, 2 mmol) was dissolved in 40 mL of methanol and the mixture was warmed at 60° C. for three days. Solvents were removed in vacuo to isolate the title compound.

Compound 20

Compound 20 was prepared using the procedure for the preparation of Compound 15, except for substituting piperidinecarbamoyl chloride for diethylcarbamoyl chloride, and the mixture was heated at 60° C. for 65 hours. The crude product was purified by HPLC on a Waters Sunfire C8 column, eluting with a gradient of 5%/50%/87%/100% methanol in 0.1% ammonium acetate.

Compound 21

Compound 21 was prepared using the procedure for the preparation of Compound 15, except for substituting morpholinecarbamoyl chloride for diethylcarbamoyl chloride, and the mixture was heated at 80° C. for 40 hours. The crude product was purified by HPLC on a Waters Sunfire C8 column, eluting with a gradient of 5%/50%/87%/100% methanol in 0.1% ammonium acetate.

Compound 22

Triphosgene (30 mg, 0.1 mmol) was dissolved in 0.5 mL of toluene; 0.1 mL of diisopropylamine was added with stirring. The solution warmed, and a precipitate formed rapidly. After ten minutes, the resultant mixture was pushed through a syringe filter into a 4-ml vial. Compound C (0.2 mmol in 2 mL of toluene) was added, and the resultant mixture was warmed at 90° C. for 40 hours. Solvents were removed in vacuo to reduce the volume by about half; the remaining material was loaded onto a 10 g silica gel column and eluted with a gradient from 1:1 ethyl acetate/hexanes to 100% ethyl acetate.

Compound 23

Compound 23 was prepared using the procedure for preparation of Compound 22, except for substituting di-n-butylamine for diisopropylamine.

Compound 24

Compound 24 was prepared using the procedure for the preparation of Compound 22, except for substituting diisobutylamine for diisopropylamine.

Compound 25

Compound 25 was prepared using the procedure for the preparation of Compound 22, except for substituting hexamethyleneimine for diisopropylamine.

Compound 26

Compound 26 was prepared using the procedure for the preparation of Compound 22, except for substituting dicyclohexylamine for diisopropylamine.

Compound 27

Compound 27 was prepared using the procedure for the preparation of Compound 15, except for substituting dimethylcarbamoyl chloride for diethylcarbamoyl chloride, and substituting Compound D for Compound C.

Compound 28

Compound 28 was prepared using the procedure for the preparation of Compound 22, except for substituting N-ethyl-N-butylamine for diisopropylamine, and substituting Compound D for Compound C. The resultant mixture was heated at 80° C. for 40 hours.

Compound 29

Compound 22 (30 mg) was dissolved in 1.5 mL of methanol and the mixture was warmed at 90° C. for 4 hours. The crude product was purified by HPLC on a Waters Sunfire C8 column, eluting with a gradient of 35% to 65% acetonitrile in 0.1% ammonium acetate.

Compound 30

Compound 23 (30 mg) was dissolved in 2 mL of methanol and the mixture was warmed at 70° C. for 65 hours. The crude product was purified by HPLC on a Waters Sunfire C8 column, eluting with a gradient of 35% to 65% acetonitrile in 0.1% aqueous ammonium acetate.

Compound 31

Compound 26 (54 mg) was dissolved in 1.5 mL of methanol and the mixture was warmed at 90° C. for 4 hours. Solvents were removed in vacuo to give the title compound as a white solid.

Compound 32

Compound D (1.5 mmol) in 10 mL toluene solution, was combined with morpholine-carbonyl chloride (0.6 mL, 3.5 equivalents); the resultant mixture was heated overnight at 80° C. Solvents were removed in vacuo: the residue was chromatographed on a 50 g silica gel column, eluting with a gradient from 1:1 ethyl acetate/hexanes to 100% ethyl acetate, to produce the title compound.

Compound 33

Compound C (1.5 mmol) in 10 mL toluene solution, was combined with 2,4-difluorobenzyl bromide (2.0 equivalents) and 30 mg of tetra-n-butylammonium iodide. The resultant mixture was heated at 90° C. for 3 days. Solvents were removed in vacuo; the residue was chromatographed on a 50 g silica gel column, eluting with a gradient from 1:1 ethyl acetate/hexanes to 100% ethyl acetate. The title compound was collected as a white solid.

Compound 34

Compound F (1.5 mmol) in 10 mL toluene solution, was combined with morpholine-carbonyl chloride (0.6 mL, 3.5 equivalents); the resultant mixture was heated at 90° C. for 8 hours. Solvents were removed in vacuo; the residue was chromatographed on a 100 g silica gel column, eluting with a gradient from 1:1 ethyl acetate/hexanes to 100% ethyl acetate, to produce the title compound.

Compound 35

Compound F (1.5 mmol) in 10 mL toluene solution, was combined with 2,4-difluorobenzyl bromide (2.0 equivalents) and 100 mg of tetra-n-butylammonium iodide. The resultant mixture was heated at 90° C. for 3 days. Solvents were removed in vacuo: the residue was chromatographed on a 50 g silica gel column, eluting with a gradient from 1:1 ethyl acetate/hexanes to 100% ethyl acetate. The title compound was collected as a white solid.

Compound 36

Compound 21 (0.92 g) was dissolved in 20 mL of methanol; 20 mg of solid sodium bicarbonate was added, and the resultant mixture was warmed at 50° C. for 40 hours. Solvents were removed in vacuo; the residue was taken up in ethyl acetate and filtered through a syringe filter. The solution was concentrated in vacuo to give the title compound.

Compound 37

Compound 33 (0.54 g) was dissolved in 20 mL of methanol; 20 mg of solid sodium bicarbonate was added, and the resultant mixture was warmed at 70° C. for 40 hours. Solvents were removed in vacuo; the residue was taken up in ethyl acetate and filtered through a syringe filter. The solution was concentrated in vacuo to give the title compound.

Compounds 38-41 having structures as shown in Table 2 were prepared as described below:

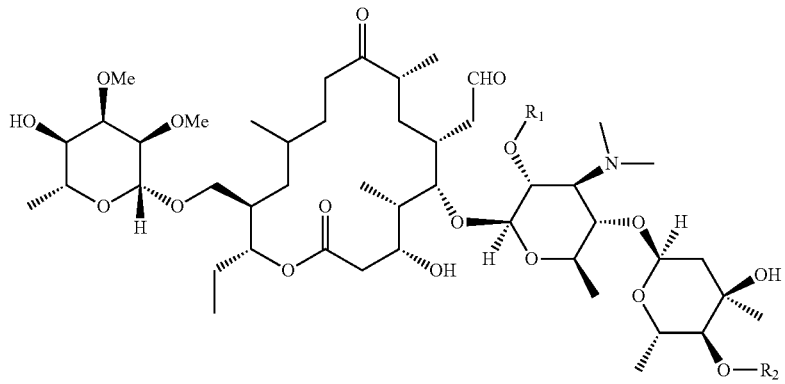

TABLE 2

| Compound | R$_1$ | R$_2$ |
|---|---|---|
| 38 | H | C(O)N(CH$_2$CH$_3$)$_2$ |
| 39 | C(O)CH(CH$_3$)$_2$ | C(O)N(CH$_2$CH$_3$)$_2$ |
| 40 | H | —CH$_2$—C$_6$H$_4$—F |
| 41 | H | —CH$_2$—C$_6$H$_3$F—F |

Compound 38

Compound 19 (200 mg) was combined with 20 mg of 10% palladium-on-carbon in 12 mL of methanol; the resultant mixture was first purged under nitrogen, then exchanged for a balloon of hydrogen gas. After stirring at ambient temperature for 4 hours, the balloon was removed, the mixture was purged with nitrogen and concentrated in vacuo. The residue was taken up in ethyl acetate and passed through a 0.45 micron filter to remove the catalyst. The resultant clear solution was concentrated in vacuo to give the title compound.

Compound 39

Compound 18 (200 mg) was combined with 20 mg of 10% palladium-on-carbon in 12 mL of methanol; the resultant mixture was first purged under nitrogen, then exchanged for a balloon of hydrogen gas. After stirring at ambient temperature for 4 hours, the balloon was removed, the mixture was purged with nitrogen and concentrated in vacuo. The residue was taken up in ethyl acetate and passed through a 0.45 micron filter to remove the catalyst. The resultant clear solution was concentrated in vacuo to give the title compound.

Compound 40

Compound K (0.83 mmol) was combined with 4-fluorobenzyl bromide (1.5 eq) and 0.1 eq of tetra-n-butylammonium iodide. The resultant mixture was heated at 90° C. for two days. The mixture was concentrated in vacuo; the residue was chromatographed on silica gel, eluting with a gradient of 20-100% ethyl acetate/hexanes. Fractions containing the target compound (as its 2'-acetate) were combined and concentrated in vacuo. The residue was dissolved in 15 mL of methanol; 20 mg of solid sodium bicarbonate was added, and the resultant solution was stirred overnight at 40° C. The mixture was concentrated in vacuo; the residue was chromatographed on silica gel, eluting with a gradient of 50-100% ethyl acetate/hexanes. The title compound (112 mg) was isolated as a white foam.

Compound 41

Compound K (0.83 mmol) was combined with 2,4-difluorobenzyl bromide (1.5 eq) and 0.1 eq of tetra-n-butylammonium iodide. The resultant mixture was heated at 90° C. for two days. The mixture was concentrated in vacuo; the residue was chromatographed on silica gel, eluting with a gradient of 20-100% ethyl acetate/hexanes. Fractions containing the target compound (as its 2'-acetate) were combined and concentrated in vacuo. The residue was dissolved in 15 mL of methanol; 20 mg of solid sodium bicarbonate was added, and the resultant solution was stirred overnight at 40° C. The mixture was concentrated in vacuo; the residue was chromatographed on silica gel, eluting with a gradient of 50-100% ethyl acetate/hexanes. The title compound (50 mg) was isolated as a white foam.

Compounds 42-46 having structures as shown in Table 1C were prepared as described below:

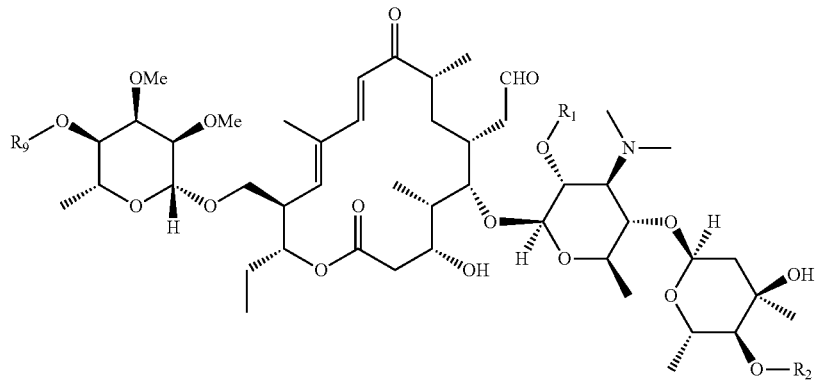

TABLE 1C

| Compound | R$_1$ | R$_2$ | R$_9$ |
|---|---|---|---|
| 42 | C(O)CH$_3$ | C(O)N(CH$_2$CH$_3$)$_2$ | C(O)CH$_2$CH$_3$ |
| 43 | H | C(O)N(CH$_2$CH$_3$)$_2$ | C(O)CH$_2$CH$_3$ |
| 44 | C(O)CH$_2$CH$_3$ | C(O)N(CH$_2$CH$_3$)$_2$ | C(O)CH$_2$CH$_3$ |
| 45 | C(O)CH$_3$ | —CH$_2$—C$_6$H$_4$—F | C(O)CH$_2$CH$_3$ |
| 46 | H | —CH$_2$—C$_6$H$_4$—F | C(O)CH$_2$CH$_3$ |

Compound 42

Compound 15 (200 mg) was dissolved in 1 mL of dry pyridine; 0.2 mL of propionic anhydride was added, and the resulting solution was stirred at ambient temperature for 2 hrs. Reaction was quenched by the addition of 0.5 mL of methanol; the mixture was stirred for 10 minutes, then concentrated in vacuo. The residue was chromatographed on a 10 g silica gel column, eluting with a solvent gradient from 20% EtOAc/hexanes to EtOAc. A pure sample (20 mg) selected from a middle cut of the major peak was confirmed to be the title compound.

Compound 43

Compound 43 (60 mg) was dissolved in 5 mL of methanol and heated at reflux for 12 hrs. Solvents were removed in vacuo; the residue was purified by HPLC on a Waters Sunfire C8 column, eluting with a gradient of 50% to 100% acetonitrile in 0.1% ammonium acetate. The title compound was isolated as a white solid (23 mg).

Compound 44

The title compound was isolated as a minor fraction (5 mg) from HPLC purification of the mixture generated during the reaction to produce Compound 43.

Compound 45

Compound 3 (435 mg) was dissolved in 2 mL of dry pyridine; 0.4 mL of propionic anhydride was added, and the resulting solution was stirred at ambient temperature for 2 hrs. Reaction was quenched by the addition of 0.5 mL of methanol; the mixture was stirred for 10 minutes, then concentrated in vacuo. The residue was chromatographed on a 40 g silica gel column, eluting with a solvent gradient from 20% EtOAc/hexanes to EtOAc. A pure sample (13 mg) selected from a middle cut of the major peak was confirmed to be the title compound.

Compound 46

Compound 45 (77 mg) was dissolved in 2 mL of methanol and warmed at 60 C for 5 days. Solvents were removed in vacuo; the residue was purified by HPLC on a Waters Sunfire C8 column, eluting with a gradient of 50% to 100% acetonitrile in 0.1% ammonium acetate. The title compound was isolated as a white solid (11 mg).

Compounds were characterized by liquid chromatography/mass spectrometry (LC-MS) analysis:

Analytical LC-MS was performed on a Finnigan Navigator mass spectrometer and Agilent 1100 HPLC system running Xcalibur 1.2, Open-Access 1.3, and custom login software. The mass spectrometer was operated under positive APCI ionization conditions. The HPLC system comprised an Agilent Quaternary pump, degasser, column compartment, autosampler and diode-array detector, with a Polymer Labs ELS-2100 evaporative light-scattering detector. The column used was a Phenomenex Luna Combi-HTS C8(2) 5 µm 100 Å (2.1 mm×50 mm), at a temperature of 55° C. A gradient of 5-100% acetonitrile (A) and 0.1% trifluoroacetic acid in water (B) was used, at a flow rate of 2.0 mL/min (0-0.1 min 5% A, 0.1-2.6 min 5-100% A, 2.6-2.9 min 100% A, 2.9-3.0 min 100-5% A. 0.5 min post-run delay). Retention times (RT) and mass ion (m/z) signals are reported.

| Compound | RT (minutes) | MS (m/z) |
|---|---|---|
| 1 | 1.67 | 1049 |
| 2 | 1.72 | 1117 |
| 3 | 1.68 | 1067 |
| 4 | 1.72 | 1083 |
| 5 | 1.79 | 1077 |
| 6 | 1.70 | 1113 |
| 7 | 1.67 | 1134 |
| 8 | 1.70 | 1095 |
| 9 | 1.75 | 1127 |
| 10 | 1.56 | 1025 |
| 11 | 1.75 | 1109 |
| 12 | 1.67 | 1043 |
| 13 | 1.79 | 1071 |
| 14 | 1.59 | 1001 |

-continued

| Compound | RT (minutes) | MS (m/z) |
|---|---|---|
| 15 | 1.61 | 1058 |
| 16 | 1.60 | 1092 |
| 17 | 1.58 | 1056 |
| 18 | 1.65 | 1086 |
| 19 | 1.52 | 1016 |
| 20 | 1.59 | 1070 |
| 21 | 1.42 | 1072 |
| 22 | 1.61 | 1086 |
| 23 | 1.72 | 1114 |
| 24 | 1.72 | 1114 |
| 25 | 1.61 | 1084 |
| 26 | 1.87 | 1166 |
| 27 | 1.56 | 1058 |
| 28 | 1.68 | 1114 |
| 29 | 1.56 | 1044 |
| 30 | 1.72 | 1072 |
| 31 | 1.74 | 1124 |
| 32 | 1.50 | 1100 |
| 33 | 1.60 | 1085 |
| 34 | 1.59 | 1114 |
| 35 | 1.70 | 1127 |
| 36 | 1.33 | 1030 |
| 37 | 1.51 | 1043 |
| 38 | 1.69 | 1019 |
| 39 | 1.73 | 1089 |
| 40 | 1.81 | 1028 |
| 41 | 1.77 | 1046 |
| 42 | 1.81 | 1113 |
| 43 | 1.78 | 1071 |
| 44 | 1.81 | 1127 |
| 45 | 1.86 | 1123 |
| 46 | 1.82 | 1081 |

Pharmacokinetic Studies

Exemplary compounds were evaluated for their pharmacokinetic profiles as follows.

Compounds were dosed orally to Sprague-Dawley rats, using appropriate formulations and doses. Serial blood samples were collected at selected time points post-dosing. Plasma was separated from the blood by centrifugation. 25 µL of plasma (sample, standard or QC) was combined with 25 µL of internal standard and 250 µL acetonitrile. Following vortexing to mix, the plates were centrifuged to separate the precipitated proteins. A 50 µL aliquot of the supernatant was transferred to a clean 96-well plate and diluted with 100 µL 0.1% formic acid. Stock standards were prepared in DMSO, with intermediate dilutions in acetonitrile:water (50:50, by volume). Samples were analyzed by LC-MS. The drug level curves were used to calculate dose-normalized area under the curve (AUC/D) data, which are reported as µg-hr/mL per mg/kg.

TABLE 3

Pharmacokinetic Properties of Example compounds (AUC/D, µg-hr/mL per mg/kg)

| Compound | AUC/D |
|---|---|
| Tylosin A | 0.0097 |
| Compound G | 0.05 |
| Compound 5 | 0.227 |
| Compound 8 | 0.51 |
| Compound 10 | 0.0165 |
| Compound 13 | 0.183 |
| Compound 14 | 0.057 |
| Compound 18 | 0.42 |
| Compound 19 | 0.04 |
| Compound 38 | 0.065 |

Pharmacokinetic properties of compounds having three non-hydrogen substituents at the alpha-position of the ester (i.e., a tri-substituted ester) were further examined. A compound having a 4"-tri-substituted ester moiety (Compound 14) was compared to a di-substituted control compound. The compounds were dosed orally, 20 mg/kg, in rats.

Table 4 shows percentages of parent and metabolite (here, "metabolite" refers specifically to the 4"-deacylated metabolite) compound following oral dosing. Parent-vs-Metabolite percentages are determined based on AUC(0-∞), which is calculated from 10 plasma samples collected over 12 hours.

TABLE 4

Comparison of parent vs. metabolite levels

| Compound | $R_1$ | $R_4$ | $R_5$ | $R_6$ | Parent % | Metabolite % |
|---|---|---|---|---|---|---|
| Control | H | H | Me | Me | <1% | >99% |
| Compound 14 | H | Me | Me | Me | >99% | <1% |

As indicated in Table 4, dosing of the control compound produces no circulating parent drug, but only the 4"-deacylated metabolite. In contrast, when the tri-substituted variant is dosed, the primary circulating material is the parent. Thus, the tri-substituted 4"-esters are pharmacokinetically distinct from and superior to di-substituted analogs. Table 4 demonstrates the beneficial effect of three non-hydrogen substituents at the alpha-position of the ester (i.e., a tri-substituted ester) on metabolic stability.

Pharmacokinetic properties of compounds having a 4"-benzyl moiety were further examined. A compound having a 4"-halobenzyl moiety (Compound 10) was compared to a compound having an unsubstituted 4"-benzyl moiety. The compounds were dosed orally, 20 mg/kg, in rats.

Table 5 shows percentages of parent and metabolite (here, "metabolite" refers specifically to the 4"-debenzylated metabolite) compound following oral dosing. Parent-vs-Metabolite percentages are determined based on AUC(0-∞), which is calculated from 10 plasma samples collected over 12 hours.

TABLE 5

Comparison of parent vs. metabolite levels

| Compound | $R_1$ | $A_1$ | Parent % | Metabolite % |
|---|---|---|---|---|
| Compound G | H | unsubstituted phenyl | 95% | 4.4% |
| Compound 10 | H | 4-fluorophenyl | >99.5% | <0.5% |

Table 5 shows that an unsubstituted 4"-benzyl group is metabolically labile; without wishing to be bound by theory, the action of cytochrome-P450-mediated oxidative metabolism may contribute to the metabolism of an unsubstituted 4"-benzyl group. In particular, as indicated in Table 5, a 4"-debenzylated metabolite was observed in pharmacokinetic studies of compounds having an unsubstituted 4"-benzyl moiety. In contrast, a compound having a 4"-halogenated benzyl moiety yields negligible amounts of the 4"-debenzylated metabolite.

Placement of certain substituents, such as halogen groups, on the aromatic ring of the 4"-benzyl group, suppresses the production of a de-benzylated metabolite. Thus, the substituted 4"-benzyl ethers disclosed herein, and, in particular, the 4"-halobenzyl ethers, are pharmacokinetically distinct from and superior to previously reported analogs. Table 5 demonstrates the beneficial effect of the 4"-halobenzyl ethers and, in particular, the 4"-fluorobenzyl ethers, on stability.

Testing for Antibiotic Activity—Agar Disc Diffusion Method

Antibacterial tests were performed on a series of tylosin A derivatives via the 'agar disc diffusion' assay. This assay is employed to determine the sensitivity of pathogens to chemical entities under investigation and is a standardized procedure outlined in 1961 by the World Health Organization.

Bacteria tested were a standard gram positive organism; *Staphylococcus aureus* ATCC 25923 (available from the American Type Culture Collection).

Colonies of bacteria are dispensed into liquid Mueller-Hinton II broth (available from Becton, Dickinson and Company), agitated and then streaked onto prepared Mueller-Hinton agar plates. Bacteria were allowed to grow for 16 hours at 37 degrees C. A sterile loupe was used to select 4-5 isolates from the cultures thus grown, and dispensed into Mueller-Hinton broth. Inoculated broth was then diluted further with fresh Mueller-Hinton II broth until a McFarland Standard (test kit available from Scientific Device Laboratory) concentration of 0.5 on the McFarland scale was achieved.

Once a McFarland standard inoculum was achieved, this stock was plated via sterile swabs onto a Mueller-Hinton II agar plate (available from Teknova), which has been stored at 4° C. and is first allowed to achieve room temperature, streaking the entire plate 3 times, and rotated 120 degrees around between inoculations.

Each tylosin A derivative was obtained as 1 mM stock solution in DMSO. For each compound, 10 µL, (10 nanomoles) was dispensed onto a 7 mm blank paper disc (available from BBL, Le Pont du Claire, France), replicates of each was thus prepared, and allowed to dry for 16 hours.

Gentamicin was used as the antibacterial standard, as it demonstrates activity against both gram positive and gram negative bacteria. Pre-dispensed 7 mm paper discs containing 10 µg of gentamicin are used (available from Becton, Dickinson and Company) and one disc was placed on each test plate of tylosin A derivatives.

To obtain a dose response curve against *Staphylococcus aureus*, 20 µL (20 nanomoles) of each tylosin A derivative to be tested as obtained from the company compound repository at 1 mM stock solution in DMSO was dispensed onto a 7 mm blank paper disc. After drying overnight, the 7 mm compound infused paper discs were placed at ~30 cm intervals upon agar plates freshly streaked with *Staphylococcus aureus* ATCC 25923. Inoculated and disc dispensed plates so prepared were allowed to grow for 16 hours at 37° C. At this time, the 'zone of inhibition' around each 7 mm paper disc (inclusive of the disc itself) was measured and recorded in Table 6 below.

TABLE 6

Antibiotic activity of Example compounds (Zone of inhibition, mm)

| Compound | Aliquot | *Staphylococcus aureus* ATCC25923 Zone of inhibition (mm) |
|---|---|---|
| Gentamicin | 20 µg | 23 |
| Compound 1 | 10 nanomoles | 12 |
| Compound 2 | 10 nanomoles | 8 |

TABLE 6-continued

Antibiotic activity of Example compounds (Zone of inhibition, mm)

| Compound | Aliquot | Staphylococcus aureus ATCC25923 Zone of inhibition (mm) |
|---|---|---|
| Compound 3 | 10 nanomoles | 18 |
| Compound 4 | 10 nanomoles | 9 |
| Compound 5 | 10 nanomoles | 19 |
| Compound 6 | 10 nanomoles | 7.5 |
| Compound 7 | 10 nanomoles | 8 |
| Compound 8 | 10 nanomoles | 11 |
| Compound 10 | 10 nanomoles | 16 |
| Compound 12 | 10 nanomoles | 15 |
| Compound 13 | 10 nanomoles | 15 |
| Compound 14 | 10 nanomoles | 14 |
| Compound 15 | 10 nanomoles | 8 |
| Compound 16 | 10 nanomoles | 17 |
| Compound 17 | 10 nanomoles | 8 |
| Compound 18 | 10 nanomoles | 15 |
| Compound 19 | 10 nanomoles | 17 |
| Compound 20 | 10 nanomoles | 8 |
| Compound 21 | 10 nanomoles | 9 |
| Compound 22 | 10 nanomoles | 13 |
| Compound 24 | 10 nanomoles | 7.5 |
| Compound 26 | 10 nanomoles | 8 |
| Compound 27 | 10 nanomoles | 18 |
| Compound 29 | 10 nanomoles | 9 |
| Compound 30 | 10 nanomoles | 7.5 |
| Compound 31 | 10 nanomoles | 8 |
| Compound 32 | 10 nanomoles | 11 |
| Compound 33 | 10 nanomoles | 14 |
| Compound 34 | 10 nanomoles | 7.5 |
| Compound 35 | 10 nanomoles | 14 |
| Compound 36 | 10 nanomoles | 7.5 |
| Compound 37 | 10 nanomoles | 17 |

Testing for Antibiotic Activity—Microdilution Method

Exemplary compounds were evaluated for their antibiotic activity profiles as follows.

Minimum inhibitory concentration ("MIC") values for the isolates were determined using a broth microdilution method. The wells of a standard 96-well microdilution plate (Costar 3795, Corning Inc., Corning, N.Y.) were filled with 150 μL, of an appropriate diluent. For test compounds supplied as powders, Column 1 was filled with 300 μL, of either the investigational or comparator agents at the appropriate stock concentration (40× the highest test concentration). A Biomek 200 was used to make eleven 2-fold serial dilutions to create a "mother plate". For compounds supplied as DMSO stocks, compounds were diluted to 50× the highest test concentrations and 2-fold serial dilutions were made manually.

For compounds supplied as solids, "daughter plates" were loaded with 185 μL using the Multidrop 384. These daughter plates were prepared on the Biomek F/X instrument which transferred 5 μL of drug solution from each well of the mother plate to each corresponding well of each daughter plate in a single step. For compounds supplied as DMSO stock, daughter plates were filled with 90 μL of media and 2 μL of drug solution from each well of the mother plate was added to each corresponding well manually.

A suspension of standardized inoculum for each organism, equivalent to a 0.5 McFarland standard, was diluted 1:10 in Mueller Hinton II broth resulting in a final concentration of approximately $5 \times 10^5$ CFU/mL during testing. Inocula were transferred to compartments of sterile reservoirs divided by length. The Biomek 2000 was used to inoculate all plates. Daughter plates were placed on the Biomek 2000 in reverse orientation so that plates were inoculated from low to high drug concentration. The Biomek 2000 delivered 10 μL of standardized inoculum into each well of the appropriate daughter plate. The final concentration of DMSO (if used as a solvent) in the test wells was 2.5%.

Plates were stacked 3 high, covered with a lid on the top plate, placed into plastic bags, and incubated at 35° C. for approximately 20 hours. An un-inoculated solubility control plate was observed for evidence of drug precipitation. MIC values were read where visible growth of the organism was inhibited.

TABLE 7

Antibiotic activity of Example compounds (MIC, μg/mL)

| Compound | S. aureus ATCC29213 | S. epidermis ATCC49134 | E. faecalis ATCC29212 | S. pneumonia ATCC49619 | H. influenza ATCC49247 |
|---|---|---|---|---|---|
| Tylosin A | 2 | 1 | 1 | 0.25 | 16 |
| Compound G | 4 | 2 | 2 | 0.25 | 16 |
| Compound 5 | 4 | 2 | 2 | 0.5 | 16 |
| Compound 8 | 8 | 2 | 2 | 0.5 | 16 |
| Compound 10 | >8 | 8 | >8 | 4 | ND |
| Compound 13 | 16 | 4 | 4 | 2 | 16 |
| Compound 14 | 4 | 1 | 2 | 0.25 | 16 |
| Compound 18 | 16 | 2 | 4 | 1 | 32 |
| Compound 19 | 8 | 2 | 1 | 4 | 32 |

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations, or methods, or any combination of such changes and modifications of use of the invention, may be made without departing from the spirit and scope thereof.

All references (patent and non-patent) cited above are incorporated by reference into this patent application. The discussion of those references is intended merely to summarize the assertions made by their authors. No admission is made that any reference (or a portion of any reference) is relevant prior art (or prior art at all). Applicant reserves the right to challenge the accuracy and pertinence of the cited references.

What is claimed is:

1. A compound of Formula (I):

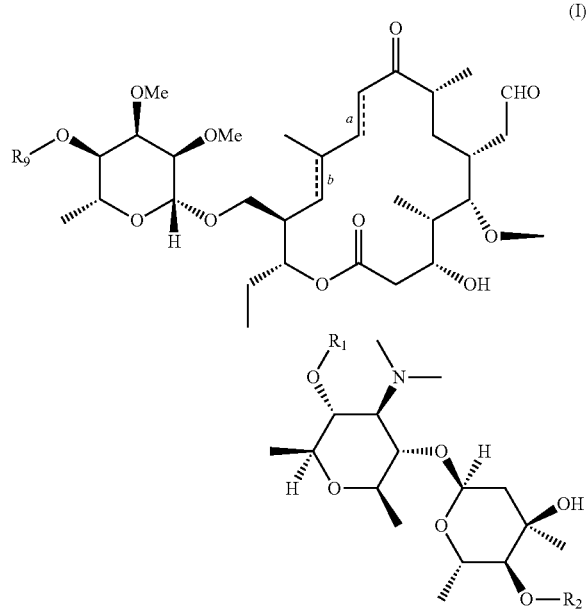

or a salt thereof, wherein:

$R_1$ represents hydrogen or —C(O)$R_3$, wherein $R_3$ represents an optionally substituted $C_1$-$C_6$-alkyl or $C_1$-$C_6$-haloalkyl;

$R_2$ represents —C(O)C($R_4$)($R_5$)($R_6$), wherein each of $R_4$, $R_5$, and $R_6$ are independently selected from the group consisting of $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl; or $R_2$ represents —C(O)N($R_7$)($R_8$), wherein each of $R_7$ and $R_8$ are independently selected from the group consisting of $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl, or $R_7$ and $R_8$ together with the nitrogen atom to which they are attached form an optionally substituted saturated or partially saturated heterocyclic ring; or $R_2$ represents —CH$_2$-A$_1$, wherein A$_1$ represents a 6- to 10-membered aryl substituted with one or more $R_A$ or a 5- to 10-membered heteroaryl, wherein the heteroaryl is unsubstituted or substituted with one or more $R_A$, wherein each $R_A$ is independently selected from the group consisting of halogen, $C_1$-$C_6$-alkyl, $C_1$-$C_6$-haloalkyl;

$R_9$ represents hydrogen or —C(O)$R_{10}$, wherein $R_{10}$ represents an optionally substituted $C_1$-$C_6$-alkyl or $C_1$-$C_6$-haloalkyl; and each of a and b independently represents either a single bond or a double bond.

2. The compound of claim 1 or a salt thereof, wherein $R_1$ is hydrogen.

3. The compound of claim 1 or a salt thereof, wherein $R_1$ is —C(O)$R_3$.

4. The compound of claim 3 or a salt thereof, wherein $R_3$ is methyl, isopropyl, or n-butyl.

5. The compound of claim 1 or a salt thereof, wherein $R_2$ is —C(O)C($R_4$)($R_5$)($R_6$).

6. The compound of claim 5 or a salt thereof, wherein each of $R_4$, $R_5$, and $R_6$ are $C_1$-$C_6$-alkyl.

7. The compound of claim 1 or a salt thereof, wherein $R_2$ is —C(O)N($R_7$)($R_8$).

8. The compound of claim 7 or a salt thereof, wherein each of $R_7$ and $R_8$ are independently $C_1$-$C_6$-alkyl, aryl, or $C_3$-$C_8$-cycloalkyl.

9. The compound of claim 7 or a salt thereof, wherein $R_7$ and $R_8$ together with the nitrogen atom to which they are attached form an optionally substituted saturated or partially saturated heterocyclic ring.

10. The compound of claim 9 or a salt thereof, wherein the heterocyclic ring is a pyrrolidine, a piperidine, an azepane, or a morpholine.

11. The compound of claim 1 or a salt thereof, wherein $R_2$ is —CH$_2$-A$_1$.

12. The compound of claim 11 or a salt thereof, wherein A$_1$ is phenyl substituted with one or more $R_A$.

13. The compound of claim 12 or a salt thereof, wherein $R_A$ is halogen.

14. The compound of claim 11 or a salt thereof, wherein A$_1$ is a 5- to 10-membered heteroaryl optionally substituted with one or more $R_A$.

15. The compound of claim 1 or a salt thereof, wherein $R_9$ is hydrogen.

16. The compound of claim 1 or a salt thereof, wherein $R_9$ is —C(O)$R_{10}$.

17. The compound of claim 16 or a salt thereof, wherein $R_{10}$ is methyl, isopropyl, or n-butyl.

18. A compound of Formula (I):

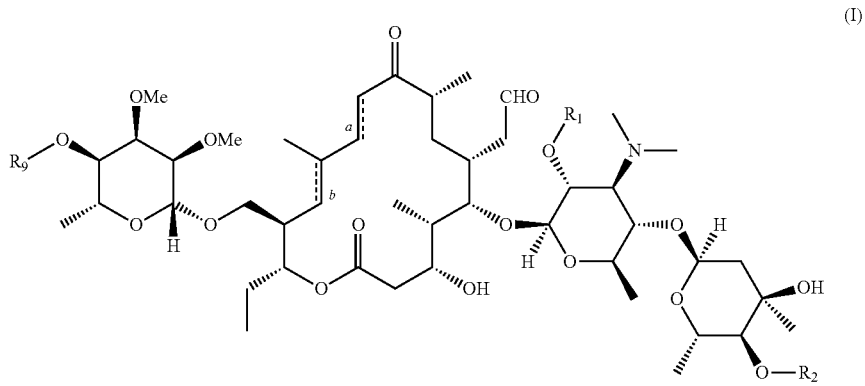

or a salt thereof, wherein:
R₁ is —C(O)CH₃ and R₂ is

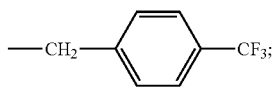

R₁ is —C(O)CH₃ and R₂ is

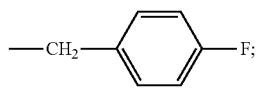

R₁ is —C(O)CH₃ ₂ is

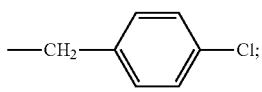

R₁ is —C(O)CH(CH₃)₂ and R₂ is

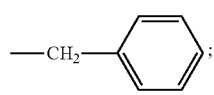

R₁ is —C(O)CH(CH₃)₂ and R₂ is

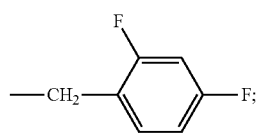

R₁ is —C(O)CH(CH₃)₂ and R₂ is

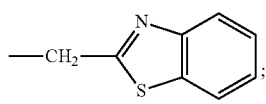

R₁ is —C(O)CH(CH₃)₂ and R₂ is

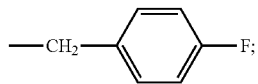

R₁ is —C(O)CH(CH₃)₂ and R₂ is

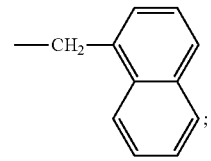

R₁ is hydrogen and R₂ is

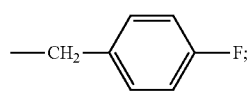

R₁ is —C(O)(CH₂)₃CH₃ and R₂ is

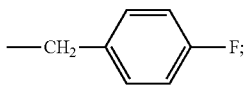

R₁ is —C(O)CH₃ and R₂ is —C(O)C(CH₃)₃; R₁ is —C(O)CH(CH₃)₂ and R₂ is —C(O)C(CH₃)₃; R₁ is hydrogen and R₂ is —C(O)C(CH₃)₃; R₁ is —C(O)CH₃ and R₂ is —C(O)N(CH₂CH₃)₂; R₁ is —C(O)CH₃ and R₂ is —C(O)N(CH₃)(C₆H₅); R₁ is —C(O)CH₃ and R₂ is

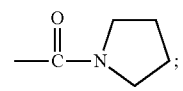

R₁ is —C(O)CH(CH₃)₂ and R₂ is —C(O)N(CH₂CH₃)₂; R₁ is hydrogen and R₂ is —C(O)N(CH₂CH₃)₂; R₁ is —C(O)CH₃ and R₂ is

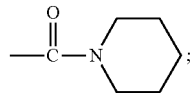

R₁ is —C(O)CH₃ and R₂ is

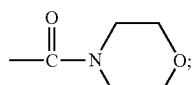

R₁ is —C(O)CH₃ and R₂ is —C(O)N(CH(CH₃)₂)₂; R₁ is —C(O)CH₃ and R₂ is —C(O)N((CH₂)₃CH₃)₂; R₁ is —C(O)CH₃ and R₂ is —C(O)N(CH₂CH(CH₃)₂)₂; R₁ is —C(O)CH₃ and R₂ is

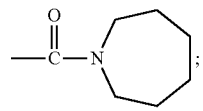

R₁ is —C(O)CH₃ and R₂ is

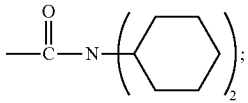

R₁ is —C(O)CH(CH₃)₂ and R₂ is —C(O)N(CH₃)₂; R₁ is —C(O)CH(CH₃)₂ and R₂ is —C(O)N(CH₂CH₃)((CH₂)₃CH₃); R₁ is hydrogen and R₂ is —C(O)N(CH(CH₃)₂)₂; R₁ is hydrogen and R₂ is —C(O)N((CH₂)₃CH₃)₂; R₁ is H and R₂ is

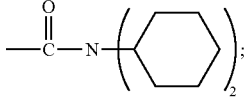

R₁ is —C(O)CH(CH₃)₂ and R₂ is

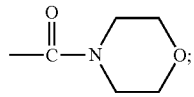

$R_1$ is —C(O)CH$_3$ and $R_2$ is

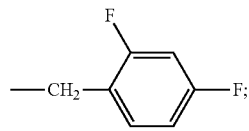

$R_1$ is —C(O)(CH$_2$)$_3$(CH$_3$) and $R_2$ is

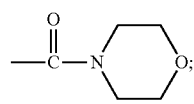

$R_1$ is —C(O)(CH$_2$)$_3$(CH$_3$) and $R_2$ is

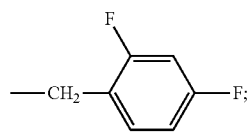

$R_1$ is hydrogen and $R_2$ is

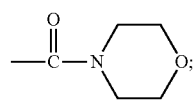

or $R_1$ is hydrogen and $R_2$ is

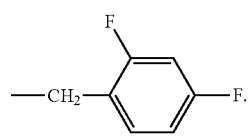

$R_9$ is hydrogen; and
wherein both a and b represent a double bond.

19. A pharmaceutical composition comprising a therapeutically effective amount of a compound of claim 1 or a salt thereof in combination with a pharmaceutically acceptable carrier.

20. A method of treating a bacterial infection in a subject in need of treatment of a bacterial infection comprising administering to the subject a therapeutically effective amount of a compound of claim 1 or a salt thereof.

21. The method of claim 20 wherein the subject is infected with Gram-positive bacteria.

22. A method of inhibiting bacterial growth or replication comprising exposing bacteria to an amount of a compound of claim 1 or a salt thereof effective to inhibit bacterial growth or replication.

23. The method of claim 22, wherein the bacteria are Gram-positive bacteria.

24. A compound of Formula (III):

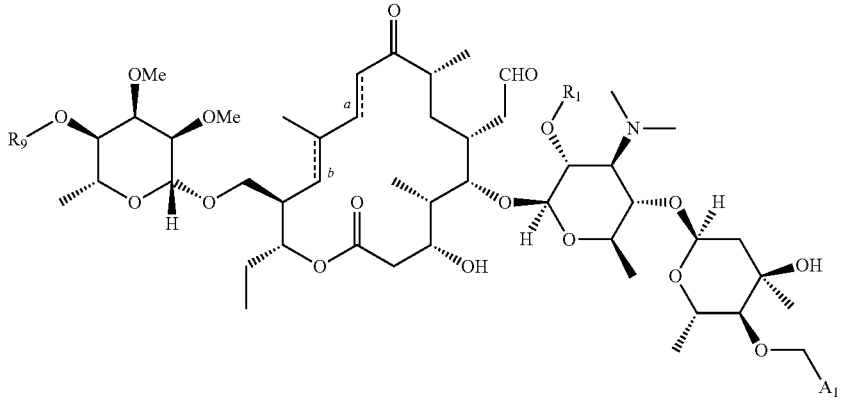

(III)

or a salt thereof, wherein:

$R_1$ represents hydrogen or —C(O)R$_3$ wherein R$_3$ represents an optionally substituted C$_1$-C$_6$alkyl or C$_1$-C$_6$-haloalkyl;

$A_1$ represents a 6- to 10-membered aryl substituted with one or more R$_4$ or a 5- to 10-membered heteroaryl, wherein the heteroaryl is unsubstituted or substituted with one or more R$_4$, wherein each R$_4$ is independently selected from the group consisting of halogen, C$_1$-C$_6$-alkyl, and C$_1$-C$_6$-haloalkyl;

$R_9$ represents hydrogen or —C(O)R$_{10}$ wherein R$_{10}$ represents an opt1onally substituted C$_1$-C$_6$alkyl or C$_1$-C$_6$-haloalkyl; and each of a and b independently represents a double bond.

25. The compound of claim 24 or a salt thereof, wherein $R_1$ is hydrogen.

26. The compound of claim 24 or a salt thereof, wherein $A_1$ is phenyl substituted with one R$_4$.

27. The compound of claim 26 or a salt thereof, wherein $R_4$ is halogen.

28. A compound of Formula (I) or a salt thereof, wherein the compound is

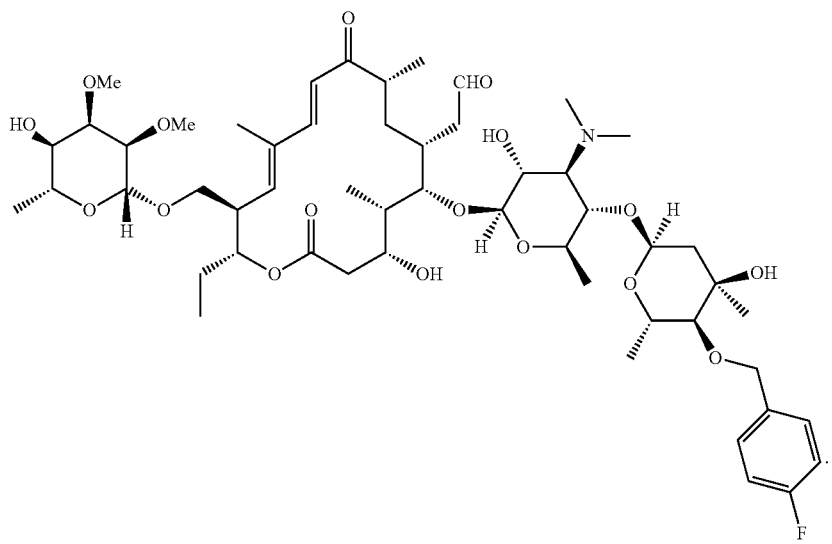

29. A pharmaceutical composition comprising a therapeutically effective amount of a compound of claim 28 or a salt thereof in combination with a pharmaceutically acceptable earlier.

30. A compound of Formula (V):

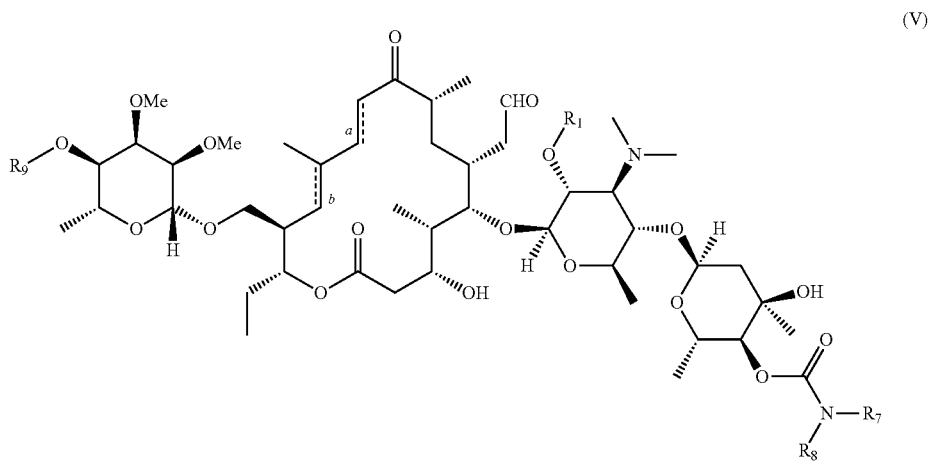

(V)

or a salt thereof, wherein:

$R_1$ represents hydrogen or —C(O)$R_3$, wherein $R_3$ represents an optionally substituted $C_1$-$C_6$-alkyl or $C_1$-$C_6$-haloalkyl, each of $R_7$ and $R_8$ are independently selected from the group consisting of $C_1$-$C_6$-alkyl, $C_1$-$C_6$-haloalkyl, aryl, heteroaryl, $C_3$-$C_8$-cycloalkyl, heterocycloalkyl, arylalkyl, heteroarylalkyl, and $C_3$-$C_8$-cycloalkyl-$C_1$-$C_4$-alkyl, or $R_7$ and $R_8$ together with the nitrogen atom to which they are attached form an optionally substituted saturated or partially saturated heterocyclic ring;

$R_9$ represents hydrogen or —C(O)$R_{10}$, wherein $R_{10}$ represents an optionally substituted $C_1$-$C_6$-alkyl or $C_1$-$C_6$-haloalkyl; and each of a and b independently represents a double bond.

31. The compound of claim 30 or a salt thereof, wherein both of $R_7$ and $R_8$ are $C_1$-$C_6$-alkyl.

32. The compound of claim 30 or a salt thereof, wherein $R_1$ is hydrogen, both of $R_7$ and $R_8$ are —CH$_2$CH$_3$, and $R_9$ is hydrogen.

33. A pharmaceutical composition comprising a therapeutically effective amount of a compound of claim 32 or a salt thereof in combination with a pharmaceutically acceptable carrier.

* * * * *